(12) United States Patent
Oberhuber et al.

(10) Patent No.: US 9,040,539 B2
(45) Date of Patent: May 26, 2015

(54) PROCESS FOR THE PREPARATION OF CHIRAL TRIAZOLONES

(75) Inventors: Michael Oberhuber, Bozen (IT); Joerg Salchenegger, Kundl/Tyrol (AT); Dominic De Souza, Holzkirchen (DE); Martin Albert, Kundl/Tyrol (AT); Thorsten Wilhelm, Kundl/Tyrol (AT); Martin Langner, Kundl/Tyrol (AT); Hubert Sturm, Kundl/Tyrol (AT); Hans-Peter Spitzenstaetter, Kundl/Tyrol (AT)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 13/697,806

(22) PCT Filed: May 18, 2011

(86) PCT No.: PCT/EP2011/058033
§ 371 (c)(1),
(2), (4) Date: Dec. 7, 2012

(87) PCT Pub. No.: WO2011/144653
PCT Pub. Date: Nov. 24, 2011

(65) Prior Publication Data
US 2013/0210833 A1   Aug. 15, 2013

(30) Foreign Application Priority Data
May 19, 2010   (EP) .................................... 10163213

(51) Int. Cl.
*A61K 31/496* (2006.01)
*C07D 405/14* (2006.01)
*C07D 295/155* (2006.01)
*C07D 405/06* (2006.01)

(52) U.S. Cl.
CPC .......... *C07D 295/155* (2013.01); *C07D 405/06* (2013.01); *C07D 405/14* (2013.01)

(58) Field of Classification Search
CPC ............................ A61K 31/496; C07D 405/14
USPC ........ 544/358, 359, 366; 514/252.12, 252.13, 514/254.05
See application file for complete search history.

(56) References Cited

U.S. PATENT DOCUMENTS

| 4,957,730 | A | | 9/1990 | Bohn et al. |
| 5,403,937 | A | | 4/1995 | Saksena et al. |
| 5,486,625 | A | | 1/1996 | Leong et al. |
| 5,693,626 | A | * | 12/1997 | Saksena et al. ................. 514/85 |
| 5,710,154 | A | * | 1/1998 | Saksena et al. .......... 514/254.07 |
| 5,714,490 | A | * | 2/1998 | Saksena et al. .......... 514/254.07 |
| 5,834,472 | A | | 11/1998 | Sangekar et al. |
| 5,972,381 | A | | 10/1999 | Sangekar et al. |
| 6,355,801 | B1 | | 3/2002 | Giesinger et al. |
| 6,958,337 | B2 | | 10/2005 | Andrews et al. |
| 2010/0197621 | A1 | | 8/2010 | Henry et al. |

FOREIGN PATENT DOCUMENTS

| EP | 0736030 A1 | 10/1996 |
| EP | 1230231 B1 | 8/2002 |
| WO | 9309114 | 5/1993 |

(Continued)

OTHER PUBLICATIONS

Blundell et al., Synlett 1994, pp. 263-265.

(Continued)

*Primary Examiner* — Golam M M Shameem
(74) *Attorney, Agent, or Firm* — Jeffrey S. Melcher; Manelli Selter PLLC

(57) ABSTRACT

A process for the preparation of a chiral compound, in particular posaconazole, wherein the process comprises mixing and reacting the compounds of formula (I) $Y_3$—$NH_2$; of formula (IIa) $O\!=\!C\!=\!N$—$Y_0$ and/or of formula (IIb) and of formula (III) in a solvent in any order to obtain a reaction mixture containing a chiral compound of formula (IV) and/or formula (V).

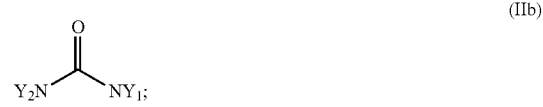

(IIb)

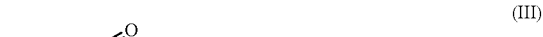

(III)

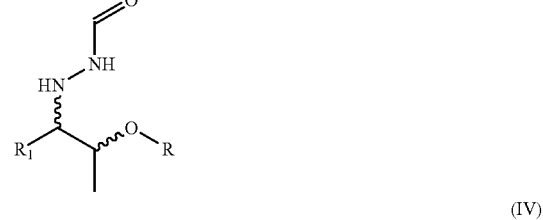

(IV)

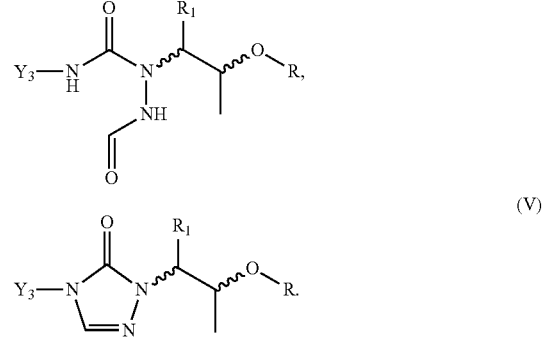

(V)

59 Claims, 5 Drawing Sheets

(56) References Cited

FOREIGN PATENT DOCUMENTS

Figure 1:
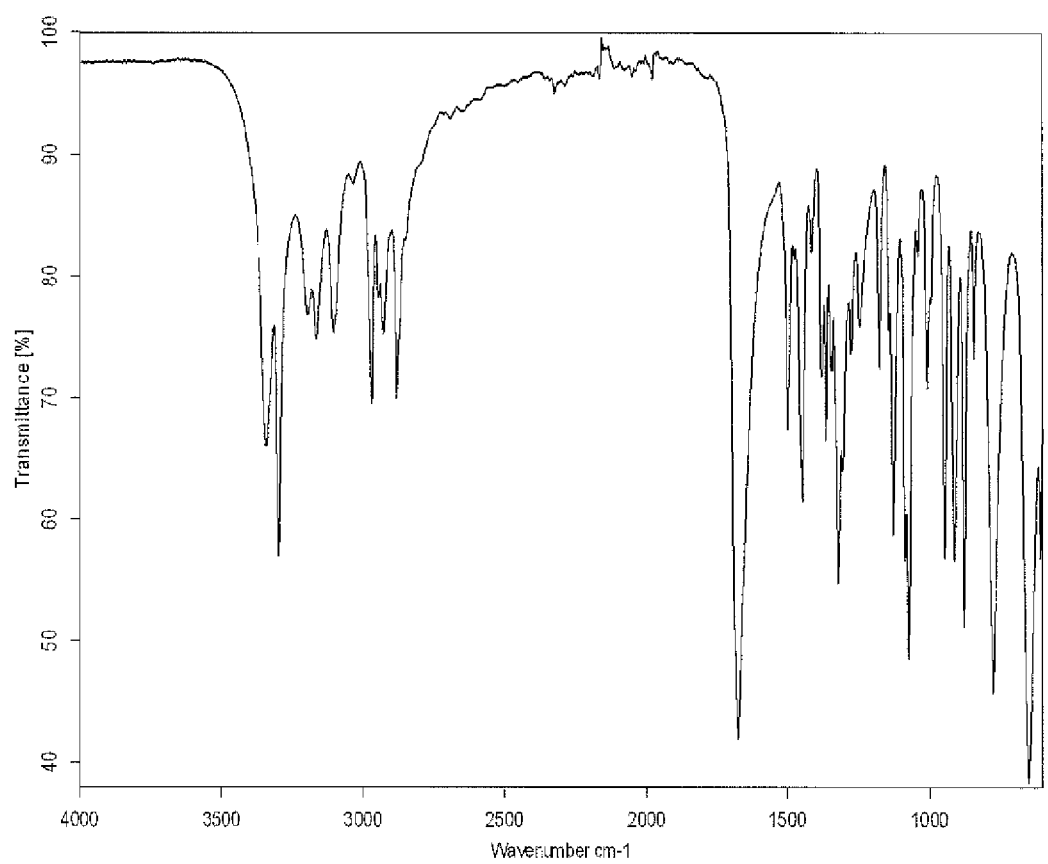

| WO | 9425452 A1 | 11/1994 |
|---|---|---|
| WO | 9516658 A1 | 6/1995 |
| WO | 9517407 A1 | 6/1995 |
| WO | 9633163 | 10/1996 |
| WO | 9633178 | 10/1996 |
| WO | 9638443 | 12/1996 |
| WO | 9700255 A1 | 1/1997 |
| WO | 9722579 | 6/1997 |
| WO | 9722710 A1 | 6/1997 |
| WO | 9733178 | 9/1997 |
| WO | 9918097 | 4/1999 |
| WO | 0280678 | 10/2002 |
| WO | 2005117831 | 12/2005 |
| WO | 2006007540 | 1/2006 |
| WO | 2007/143390 | 12/2007 |
| WO | 2009/129297 | 10/2009 |
| WO | 2010000668 | 1/2010 |
| WO | 2011/144655 | 11/2011 |
| WO | 2011/144656 | 11/2011 |
| WO | 2011/144657 | 11/2011 |
| WO | 2013/186320 | 12/2013 |

OTHER PUBLICATIONS

Brown et al., J. Chem. Soc. 2003, 125 (36), 10808-10809.
Cordova et al., Chem. Eur. J. 2004, 10 (15), 3673-3684.
Di Santo et al., "antifungal estrogen-like imidazoles. Synthesis and antifungal activities of thienyl and 1H-pyrrolyl derivatives of 1-aryl-2-(1H-imidazol-1-yl)ethane", European Journal of Medicinal Chemistry, Editions Scientifique Elsevier, Paris, FR, vol. 32, No. 2, Jan. 1, 1997, pp. 143-149.
Greene et al., Protective Groups in Organic Synthesis:, 2nd ed., John Wiley & Sons, New York 1991 10-142.
Greene et al., Protective Groups in Organic Synthesis:, 3rd ed., Wiley-Interscience (1999).
Hayashi et al., J. Org. Chem. 2005, 69 (18), 5966-5973.
Hepperle et al., Tetrahedron Lett. 2002, 43, 3359-3363.
Huang et al., Organic Letters 2004, 6 (25) 4795-4798.
Kurome et al., "Total Synthesis of an Antifungal Cyclic Depsipeptide Aureobasidin A", Tetrahedron, Elsevier Science Publishers. Amsterdam, NL, vol. 52, No. 12. Mar. 18, 1996, pp. 4327-4346.
Na Y-M et al., "Synthesis and antifungal activity of new 1-halogenbenzyl-3-imidazoly 1methylindole derivatives", European Journal of Medicinal Chemistry, Editions Scientifique Elsevier, Paris, FR, vol. 38, No. 1, Jan. 1, 2003, pp. 75-87.
Peterson, "Carbonyl olefination reaction using silyl-substituted organometallic compounds", J. Org. Chem (1968) 33 (2) pp. 780-784.
Remington's Pharmaceutical Sciences, 15th Ed., Mack Publishing Co., New Jersey (1991).
Saksena et al., Tetrahedron Lett. 2004, 45 (44), 8249-8251.
Tetrahedron Letters 32 (1991). pp. 7545-7548.
Xianhai Huang et al., "Manipulation of N,O-Nucleophilicity: Efficient Formation of 4-N-Substituted 2,4-Dihydro-3H-1,2,4-Triazolin-3-ones", Organic Letters, American Chemical Society, US, vol. 6, No. 25, Nov. 10, 2004, pp. 4795-4798.
International Search Report and Written Opinion Mailed Sep. 9, 2011 in PCT/EP2011/058035.
International Search Report and Written Opinion Mailed Aug. 4, 2011 in PCT/EP2011/058036.
International Search Report and Written Opinion Mailed Aug. 5, 2011 in PCT/EP2011/058039.
International Search Report and Written Opinion Mailed Jul. 13, 2011 in PCT/EP2011/058033.
Weichung Thou et al., Survey of Syntheses of Azole Antifungals. Chinese Journal of Pharmaceuticals, vol. 37, No. 2, pp. 125-133, Dec. 31, 2006.
Sixi, Wang, Synthesis of SIPI-4678 and Voriconazole, The Master Degree Theses of the Shanghai Institute of Parmaceutical Industry, pp. 10-13, Mar. 2007.
Sixi, Wang, Synthesis of SIPI-4678 and Voriconazole, The Master Degree Theses of the Shanghai Institute of Pharmaceutical Industry, pp. 9-17, Jan. 24, 2007.
Chinese Office Action issued in Application No. 201180024340.2, Mar. 24, 2014, pp. 1-13. and translation.
Chinese Office Action issued in Application No. 201180024363.3, Jan. 17, 2014. pp. 1-7, and translation.
Chinese Office Action issued in Application No. 201180024632.6, May 20, 2014. pp. 1-10, and translation.
Robert V. Hoffman, Organic Chemistry: An Intermediate Text, Second Edition, John Wiley & Sons, Inc., 2004, p. 128.
Serajuddin, Abu. Advanced Drug Delivery Reviews 59 (2007) pp. 603-616.
Reichardt, Chr. Solvents and Solvent Effects in Organic Chemistry. 3rd ed. Wiley-VCH. (2004) pp. 418-421.
Parmee, "Human beta3 adreneergic receptor containing cyclic ureidobenzenesulonafides," Bioorganic & Medicinal Chemistry Letters, vol. 9, 1999, pp. 749-745, XP002648199.
International Preliminary Report on Patentability issued in PCT/EP2012/061346, WO2012/172015, Oct. 9, 2013, pp. 1-8.
International Search Report issued in PCT/EP2012/061346, WO2012/172015, Aug. 1, 2012, pp. 1-9.
Written Opinion issued in PCT/EP2012/061346, WO2012/172015, Jun. 20, 2013, pp. 1-5.
International Preliminary Report on Patentability issued in PCT/EP2012/061346, WO2012/172015, Jun. 3, 1014, pp. 1-29.
International Search Report issued in PCT/EP2013/062298, WO2013/186320, Feb. 8, 2013, pp. 1-4.
Written Opinion issued in PCT/EP2013/062298,WO2013/186320, Feb. 8, 2013, pp. 1-13.
Hacker, "Aromatic 2-(Thio)ureidocarboxylic Acids as New Family of Modulators of Multidrug Resistance-Associated Protein 1: Synthesis, Biological Evaluation, and Structure-Activity Relationships," Journal of Medicinal Chemistry, 2009, vol. 52, No. 15, pp. 4587-4593.
Office Action issued in Chinese Patent Application Serial No. 2011800243402, Dec. 8, 2014, pp. 1-13, translation included.

* cited by examiner

PROCESS FOR THE PREPARATION OF CHIRAL TRIAZOLONES

The present invention relates to a process for the preparation of a chiral compound, preferably the preparation of chiral triazolones, more preferably the preparation of disubstituted triazolone antifungals, in particular posaconazole. According to the inventive process, a particularly preferred compound used for said preparation is carbonyldiimidazole (CDI), and thus, the present invention also relates to the use of CDI for the preparation of a chiral compound, in particular posaconazole.

BACKGROUND PRIOR ART

Posaconazole (CAS Registry Number 171228-49-2; CAS Name: 2,5-anhydro-1,3,4-trideoxy-2-C-(2,4-difluorophenyl)-4-[[4-[4-[4-[(1S,2 S)-1-ethyl-2-hydroxypropyl]-1,5-dihydro-5-oxo-4H-1,2,4-triazol-4-yl]phenyl]-1-piperazinyl]phenoxy]methyl]-1-(1H-1,2,4-triazol-1-yl)-D-threo-pentitol) is a triazole antifungal drug represented by the structure:

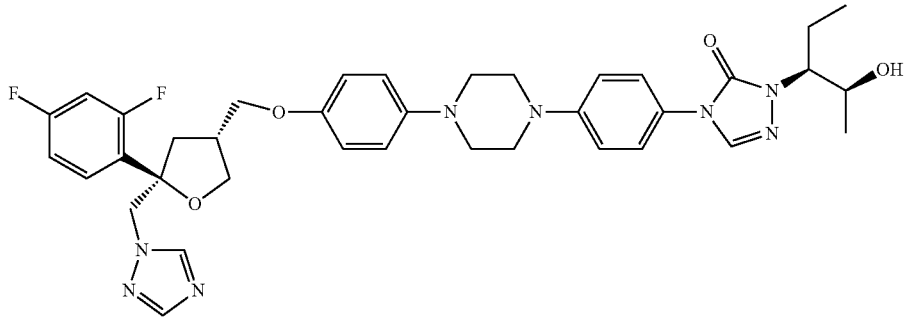 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

Posaconazole is used, for example, to prevent and/or treat invasive fungal infections caused by *Candida* species, *Mucor* species, *Aspergillus* species, *Fusarium* species, or *Coccidioides* species in immunocompromised patients and/or in patients where the disease is refractory to other antifungal agents such as amphothericin B, fluconazole, or itraconazole, and/or in patients who do not tolerate these antifungal agents.

Currently known processes for the preparation involve a two-step procedure with harsh reaction conditions which necessitate very stable protecting groups, reducing the yield and quality of the triazolone product.

A process of the prior art for the preparation of a triazolone compound is disclosed in WO 96/33178. In this reaction, the triazolone ring in posaconazole is formed by heating of an aromatic carbamate, prepared from the corresponding amine and phenyl chloroformate, and an O-protected hydrazide for 24-48 hours at more than 100° C. Such harsh reaction conditions during condensation of the triazolone ring are believed to cause significant degradation, becoming evident by the darkening of the product which is obtained in a yield of 80% after deprotection. When applied to the synthesis of tetrahydrofuran azole antifungal agents, cleavage of the O-protecting group, typically benzyl, is believed not to be quantitative. Therefore, traces of the protected compound may be found in the respective pharmaceutical composition containing the product. Further, the activation of the aromatic amine as phenyl carbamate involves the mutagenic compound phenyl chloroformate

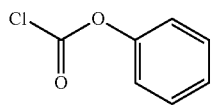

and substantial amounts of toxic phenol are produced. The prolonged heating of 24 to 48 hours further reduces yield and quality of the product and obviously requires a significant and undue amount of energy.

Another process for the preparation of disubstituted triazolone compounds in general is disclosed in WO 93/09114. Document WO 95/17407 specifically relates to the preparation of posaconazole. Both documents teach the reaction of an aromatic carbamate, prepared as described above, with hydrazine followed by heating with formamide acetate to give an N-substituted triazolone. Said triazolone is alkylated satisfactorily with aliphatic hydrocarbon chains, but not with O-substituted alkyl groups as required for the preparation of posaconazole. As to the use of O-alkylating agents, the process taught by these documents involves a large excess of alkylating agent and thus gives rise to a mixture of N-alkylated and O-alkylated isomers. Consequently, tedious purification is necessary which is costly, time-consuming and reducing the yield for this step to 50% or less, thus rendering the process highly disadvantageous, in particular for industrial-scale processes for the preparation of these triazolone compounds such as posaconazole.

Yet another process is described in WO 2006/007540. A similar reaction is published by Huang et al., Organic Letters 2004, 6 (25) 4795-4798. This reaction involves the activation of an aliphatic amine with phosgene and the addition of unsubstituted formyl hydrazine followed by heating in hexamethyldisilazane at 140° C. for up to 30 hours to give N-unsubstituted triazolone compounds in low to moderate yields. This process has not been described for the synthesis of triazolone-containing antifungal compounds such as posaconazole which would require the reaction with aromatic amines. In this respect, the N-alkylation step following the formation of the triazolone would obviously face the same difficulties and restrictions as described in the context of the prior art documents above.

Summarized, it is noted that all known processes for the synthesis of triazolone compounds, in particular posaconazole, from aromatic amines, such as $Y_3$—$NH_2$ wherein $Y_3$ is an optionally substituted aryl residue, in particular from aromatic amines of formula

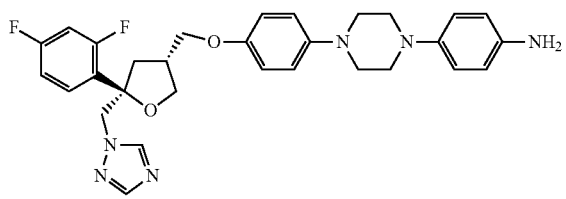 [SMILES: Nc1ccc(N2CCN(c3ccc(OC[C@@H]4CO[C@@](Cn5cncn5)(c5ccc(F)cc5F)C4)cc3)CC2)cc1]

require and produce a large amount of toxic and/or polluting reagents, involve prolonged reaction times at high temperatures and, concerning the preparation of posaconazole, are only specifically taught for the benzyl-protected hydrazide

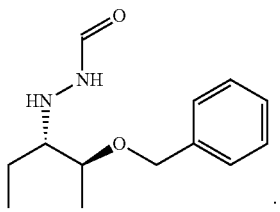 [SMILES: CC[C@H](NNC=O)[C@H](C)OCc1ccccc1]

Unprotected or, for example, silyl-protected hydrazides result in complex mixtures with minor contents of posaconazole. For the synthesis of antifungal triazolone compounds, these process constraints cause considerable pollution and waste of materials and/or energy, decrease the quality of the product and leave traces of protected triazolone compounds, in particular benzyl-protected triazolone compounds, especially

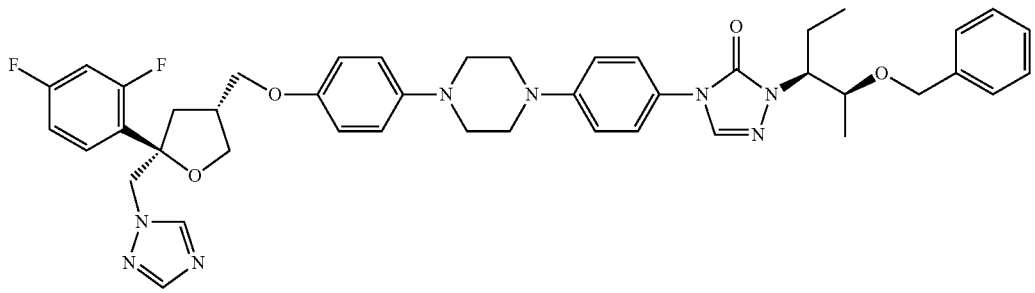 [SMILES: CC[C@@H]([C@H](C)OCc1ccccc1)n1ncn(-c2ccc(N3CCN(c4ccc(OC[C@@H]5CO[C@@](Cn6cncn6)(c6ccc(F)cc6F)C5)cc4)CC3)cc2)c1=O]

in the antifungal agent products and the respective pharmaceutical composition.

Therefore, it was an object of the present invention to provide a novel process which overcomes at least one of the problems of the prior art processes.

SUMMARY OF THE INVENTION

Surprisingly, it was found that it is possible to prepare such triazolone compounds under much milder conditions than suggested and taught in the art. Such novel and inventive process further allows for the preparation of disubstituted triazolone compounds in excellent yield and quality with a wide choice of protecting groups, even including the possibility of working without protecting group. According to a preferred embodiment, the new process of the present invention allows the use of unprotected hydrazides for the synthesis of antifungal agents.

In particular, according to the present invention, it was surprisingly found that carbonyldiimidazole can be used to mildly activate aromatic amines, in particular amines such as $Y_3$—$NH_2$ wherein $Y_3$ is an optionally substituted aryl residue, especially aromatic amines of formula

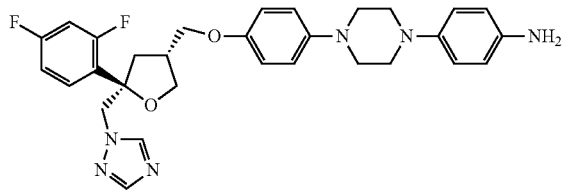 [SMILES: Nc1ccc(N2CCN(c3ccc(OC[C@@H]4CO[C@@](Cn5cncn5)(c5ccc(F)cc5F)C4)cc3)CC2)cc1]

for, surprisingly, the chemoselective acylation of hydrazides. Due to this excellent chemoselectivity, it was surprisingly found that—compared to the prior art—at extremely mild conditions with considerably decreased reaction time and temperature, unprotected hydrazides or O-silyl-protected hydrazides can be employed. A consequence of the new process of the present invention is that the only by-product produced in significant amounts is the non-toxic imidazole. Previously unknown intermediate compounds could be isolated and/or converted to triazolone compounds by heating in suitable solvents allowing for an unexpectedly efficient and clean synthesis. An optional added suitable silylation agent was surprisingly found to further improve the triazolone ring formation in terms of rate and selectivity.

A major advantage of the new process is the fact that the process is not dependent on specific protecting groups and, thus, free of associated by-products.

Therefore, the present invention relates to process for the preparation of a chiral compound, comprising (1.1) providing a compound of formula (I)

$$Y_3\text{—}NH_2 \qquad (I)$$

or a salt thereof, wherein $Y_3$ is an optionally substituted aryl residue;

(1.2) providing a compound of formula (IIa)

$$O\text{=}C\text{=}N\text{—}Y_0 \qquad (IIa)$$

or phosgene or a phosgene derivative of formula (IIb)

$$Y_2N-\underset{\underset{O}{\|}}{C}-NY_1 \qquad (IIb)$$

wherein $Y_0$ is an optionally substituted alkyl or aryl residue, and wherein $Y_1N$— and $Y_2N$— are the same or different optionally substituted nitrogen heterocycle moieties, preferably selected from the group consisting of imidazolyl and benzimidazolyl;

(1.3) providing a compound of formula (III)

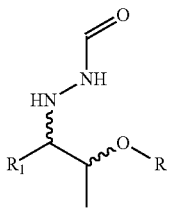
(III)

or a salt thereof, wherein $R_1$ is an alkyl residue preferably having from 1 to 6 carbon atoms, and wherein —R is —H or a suitable hydroxyl protecting group preferably selected from the group consisting of —$SiR_aR_bR_c$ and optionally substituted alkyl, aryl, alkaryl or aralkyl residues, where $R_a$, $R_b$ and $R_c$ are the same or different and selected from the group consisting of optionally suitably substituted alkyl and aryl residues;

(2) mixing and reacting the compounds of formulae (I), (IIa) and/or (IIb)), and (III) in a solvent in any order to obtain a reaction mixture containing a chiral compound of formula (IV) and/or formula (V)

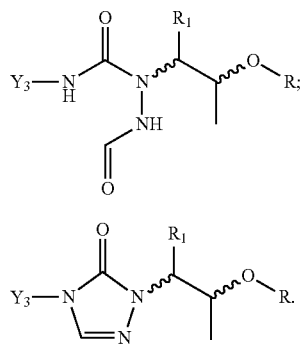
(IV)

(V)

According to a preferred embodiment, the present invention relates to a process for the preparation of a chiral compound, comprising (1.1) providing a compound of formula (I)

(I)

or a salt thereof, wherein $Y_3$ is an optionally substituted aryl residue;

(1.2) providing a compound of formula (IIa)

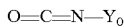
(IIa)

or phosgene or a phosgene derivative of formula (IIb)

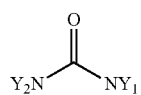
(IIb)

wherein $Y_0$ is an optionally substituted alkyl or aryl residue, and wherein $Y_1N$— and $Y_2N$— are the same or different optionally substituted nitrogen heterocycle moieties, preferably selected from the group consisting of imidazolyl and benzimidazolyl;

(1.3) providing a compound of formula (III)

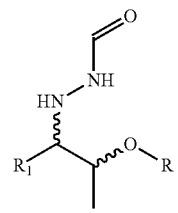
(III)

or a salt thereof, wherein $R_1$ is an alkyl residue preferably having from 1 to 6 carbon atoms, and wherein —R is —H or a suitable hydroxyl protecting group preferably selected from the group consisting of —$SiR_aR_bR_c$ and optionally substituted alkyl, aryl, alkaryl or aralkyl residues, where $R_a$, $R_b$ and $R_c$ are the same or different and selected from the group consisting of optionally suitably substituted alkyl and aryl residues;

(2) mixing and reacting the compounds of formulae (I), (IIa) and/or (IIb)), and (III) in a solvent in any order to obtain a reaction mixture containing a chiral compound of formula (IV) and/or formula (V)

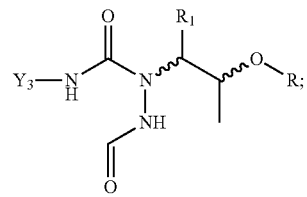
(IV)

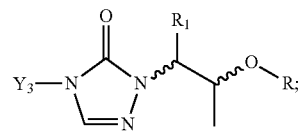
(V)

wherein in (2), (2.1) the compounds of formulae (I) and (IIa) and/or (IIb) are mixed and at least partially reacted in a solvent to obtain a reaction mixture;

(2.2) and the compound of formula (III) is added to the reaction mixture obtained from (2.1);

(3) either heating the mixture obtained from (2), optionally during and/or after solvent exchange, or heating a mixture obtained from mixing the isolated chiral compound of formula (IV) with a solvent, to a temperature in the range of from 40 to 150° C. to obtain a compound according to formula (V)

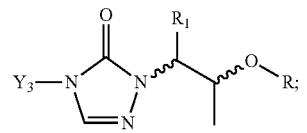
(V)

(4) extracting the compound of formula (V), preferably using a suitable aqueous acid, more preferably an aqueous inorganic acid and more preferably aqueous hydrochloric acid, as extracting agent;

(5) crystallizing the compound of formula (V) in a solvent;
(6) optionally separating the crystallized compound of formula (V) from the solvent.

According to a further preferred embodiment, the present invention relates to a process for the preparation of posaconazole, comprising
(1.1) providing a compound of formula (Ia)

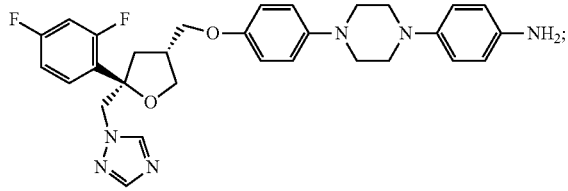

(1.2) providing a compound of formula (IIc)

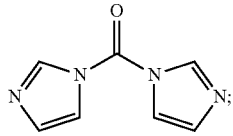

(1.3) providing a compound of formula (IIIa)

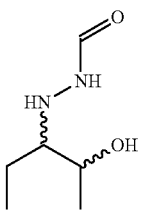

wherein at least 99% of the molecules of said compound are present as compound of formula (IIIb)

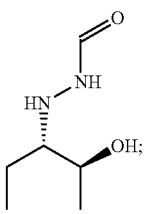

(2) mixing and reacting the compounds of formulae (Ia), (IIc), and (IIIa) in a solvent in any order to obtain a reaction mixture containing a chiral compound of formula (IVb)

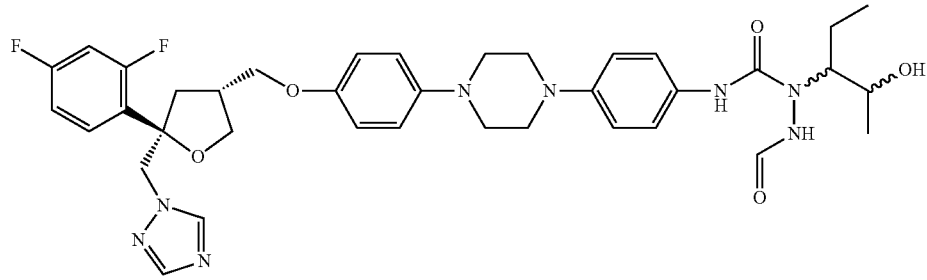

wherein at least 99% of the molecules of said compound are present as compound of formula (IVd)

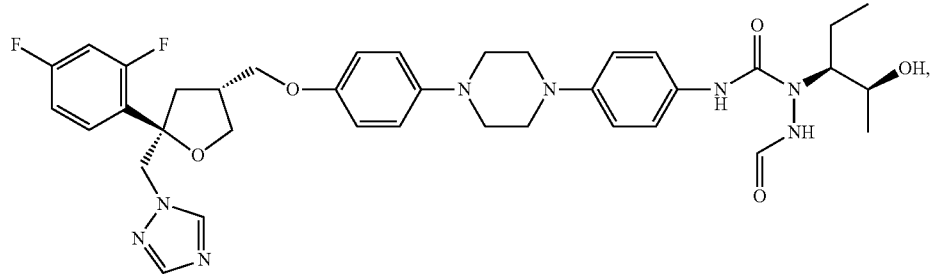

and/or of formula (Vb)

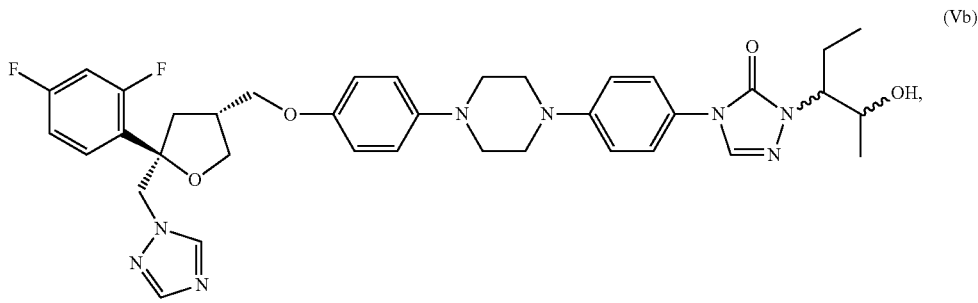 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

wherein at least 99% of the molecules of said compound are present as compound of formula (Vd)

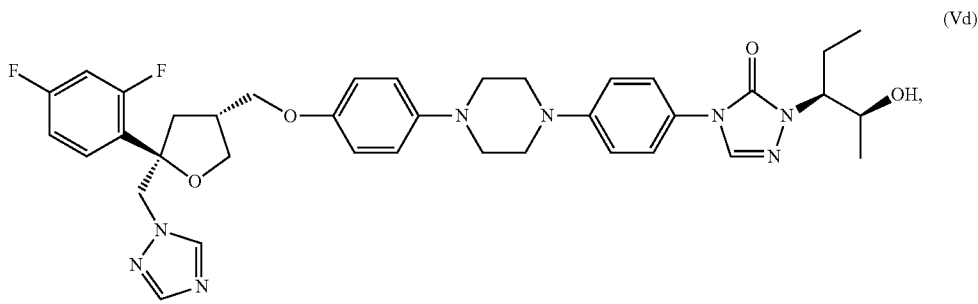

wherein in (2),
(2.1) the compounds of formulae (Ia) and (IIc) are mixed and at least partially reacted in a solvent to obtain a reaction mixture;
(2.2) and the compound of formula (IIIa) is added to the reaction mixture obtained from (2.1);
(3) either heating the mixture obtained from (2), optionally during and/or after solvent exchange, or heating a mixture obtained from mixing the isolated chiral compound of formula (IVb) with a solvent, to a temperature in the range of from 40 to 150° C. to obtain a compound according to formula (Vb);
(4) extracting the compound of formula (Vb), using aqueous hydrochloric acid, as extracting agent;
(5) crystallizing the compound of formula (Vb) in a solvent;
(6) optionally separating the crystallized compound of formula (Vb) from the solvent.

Moreover, the present invention relates to an optionally crystalline chiral compound of formula (IVa)

or a salt thereof, wherein $R_1$ is an alkyl residue preferably having from 1 to 6 carbon atoms, more preferably from 1 to 4 carbon atoms, more preferably 1 or 2 carbon atoms, most preferably 2 carbon atoms, $R_1$ in particular being ethyl, and wherein —R is —H or a suitable hydroxyl protecting group preferably selected from the group consisting of —$SiR_aR_bR_c$ and optionally substituted alkyl, aryl, alkaryl or aralkyl residues, where $R_a$, $R_b$ and $R_c$ are the same or different and selected from the group consisting of optionally suitably substituted alkyl and aryl residues, with —R preferably being —H or a hydroxyl protecting group selected from the group consisting of —$Si(CH_3)_3$ and benzyl, —R in particular being —H, and wherein said compound is most preferably a compound of formula (IVb)

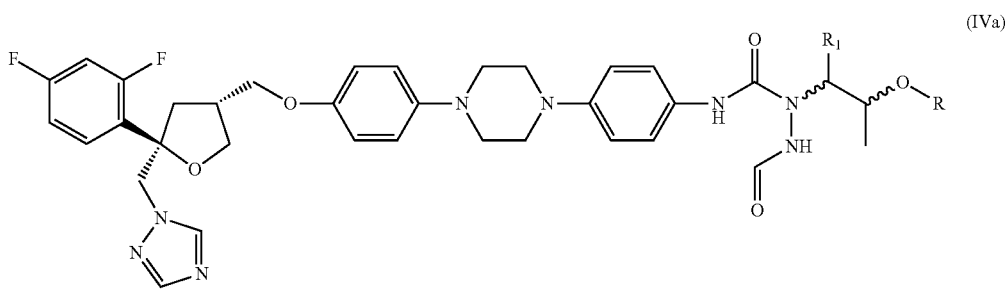

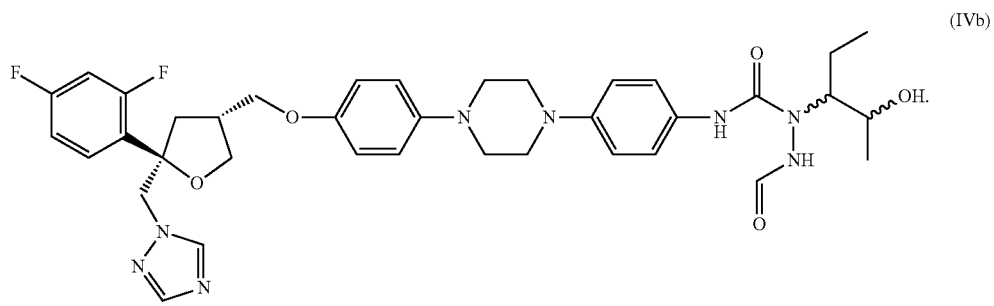 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

(IVb)

Also, the present invention relates to a composition comprising a preferably crystalline chiral compound of formula (Va)

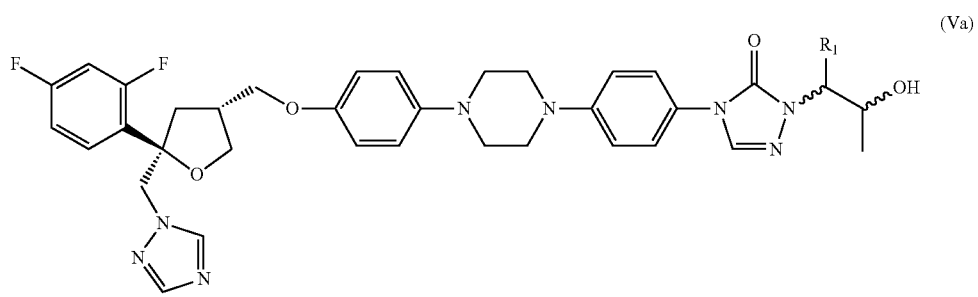

(Va)

or a salt thereof, wherein $R_1$ is an alkyl residue preferably having from 1 to 6 carbon atoms, more preferably from 1 to 4 carbon atoms, more preferably 1 or 2 carbon atoms, most preferably 2 carbon atoms,
said composition preferably comprising a compound of formula (Vb)

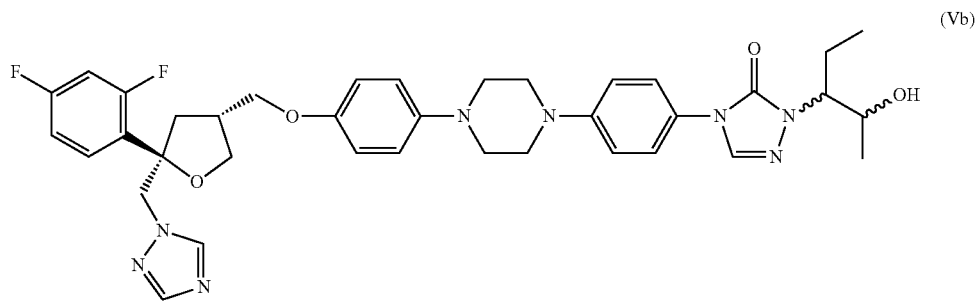 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vb)

wherein preferably at least 95%, more preferably at least 97%, more preferably at least 99% of the molecules of said preferably crystalline compound are present as isomer of formula (VC)

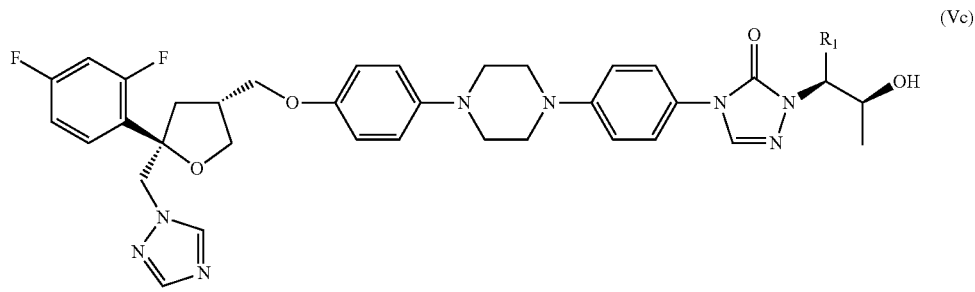
(Vc)
preferably as isomer of formula (Vd)
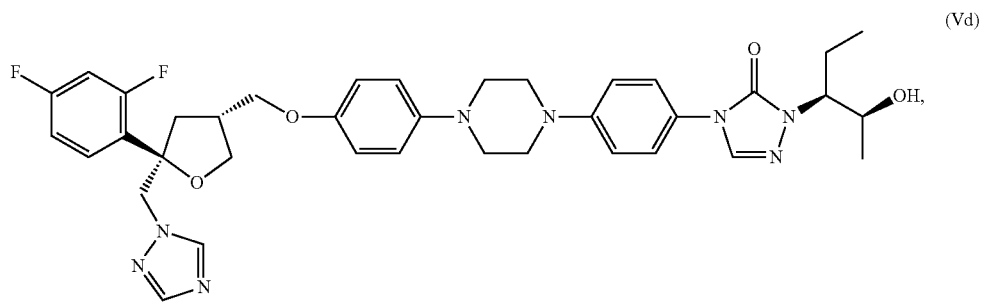 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vd)
said composition containing at most 70 weight-ppm, preferably at most 50 weight-ppm, more preferably at most 30 weight-ppm, more preferably at most 10 weight-ppm, said composition in particular being free of a compound of formula (Ve)
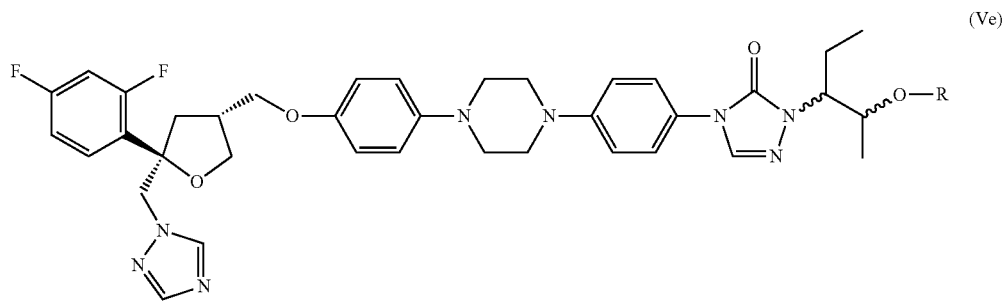
(Ve)
preferably free of a compound of formula (Vf)
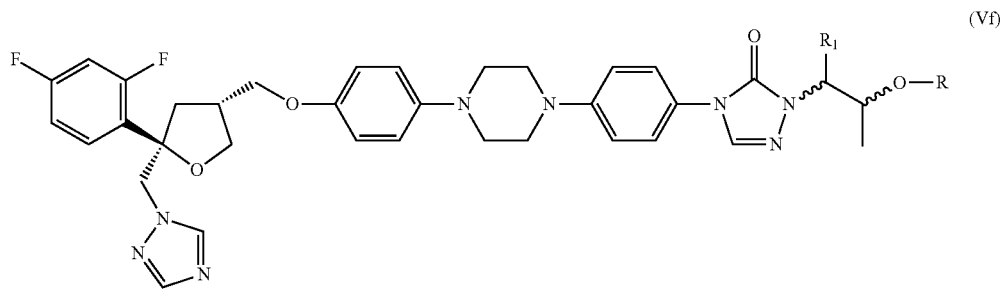
(Vf)

wherein —R is —CH₂—C₆H₅, —R preferably being selected from the group consisting of —SiR$_a$R$_b$R$_c$ and optionally substituted alkyl, aryl, alkaryl or aralkyl residues, where R$_a$, R$_b$ and R$_c$ are the same or different and selected from the group consisting of optionally suitably substituted alkyl and aryl residues, —R more preferably being a hydroxyl protecting group.

Yet further, the present invention relates to the use of a compound of formula (IIc)

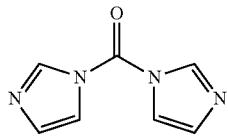

(IIc)

for the preparation of an antifungal agent, preferably for the preparation of a preferably crystalline chiral compound of formula (Vb)

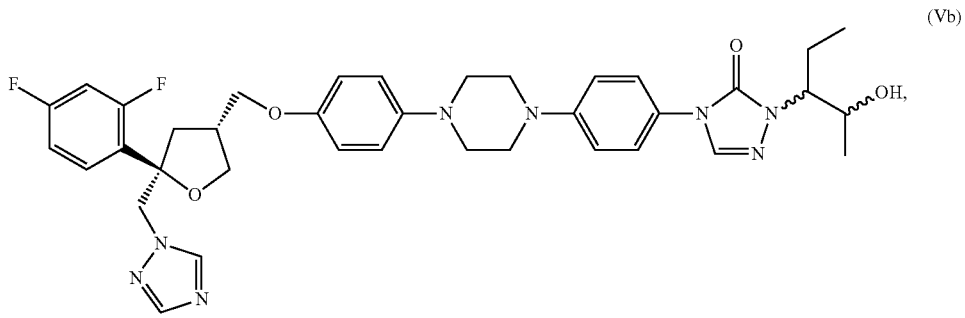 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vb)

most preferably for the preparation of a preferably crystalline compound of formula (Vd)

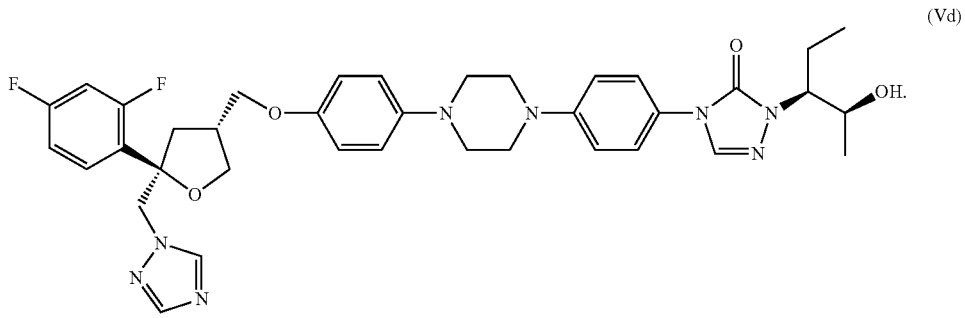 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vd)

SHORT DESCRIPTION OF THE FIGURES

FIG. 1 shows the infrared spectrum (IR) of the compound of formula (IIIa) as obtained according to Example 3 of the present invention. In FIG. 1, transmittance in % is presented on the y-axis, while wavenumber cm$^{-1}$ is presented on the x-axis. The following IR peaks can be seen in particular: 3341, 3298, 2970, 2881, 1674, 1497, 1447, 1319, 1125, 1071, 945, 910, 876, 775 and 650+/−2 cm$^{-1}$.

Figure 2:
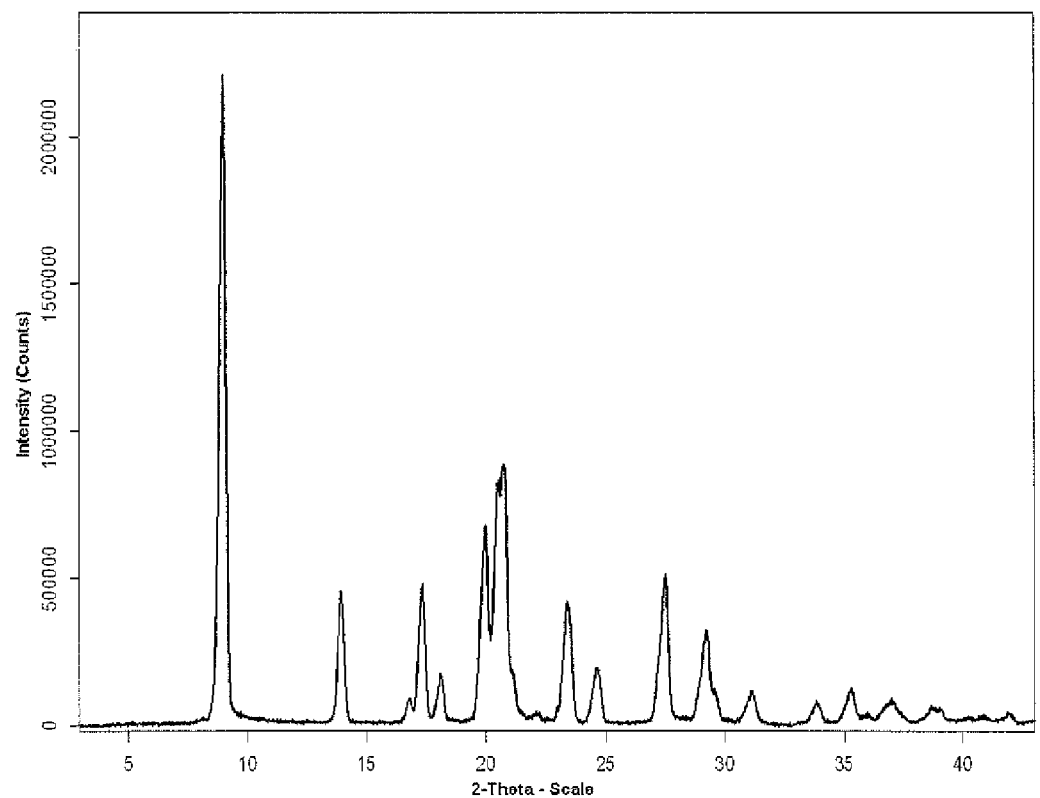

FIG. 2 shows the X-ray diffraction pattern of the compound of formula (IIIa) as obtained according to Example 3 of the present invention. In FIG. 2, intensity—measured as counts per 300 seconds (linear scale)—is presented on the y-axis, while the position—expressed as 2 theta values in degrees— is presented on the x-axis. The following XRD peaks can be seen in particular: 9.0, 13.9, 17.4, 18.1, 20.0, 20.7, 23.4, 24.6, 27.5 and 29.2+/−0.2° 2-Theta.

Figure 3:
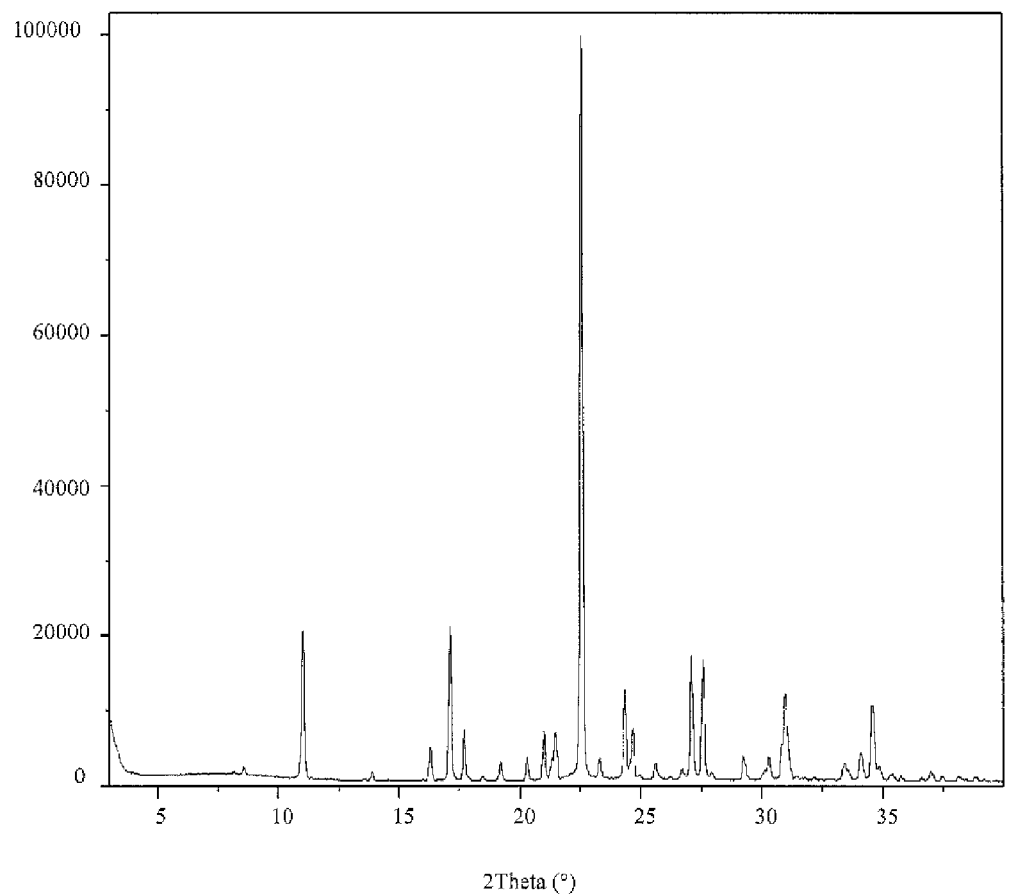

FIG. 3 shows the X-ray powder diffraction pattern (XRD) of the HCl salt of the compound of formula (GG) as obtained according to Example 1 (Ex1.h) of the present invention. The cis:trans ratio, i.e. the ratio compound of formula (GGa): compound of formula (GGb) is 99.2:0.8. In FIG. 3, on the x-axis, the position expressed as 2 theta values in degrees—is shown, on the y-axis, the intensity—measured as counts per second (linear scale)—is shown.

Figure 4:
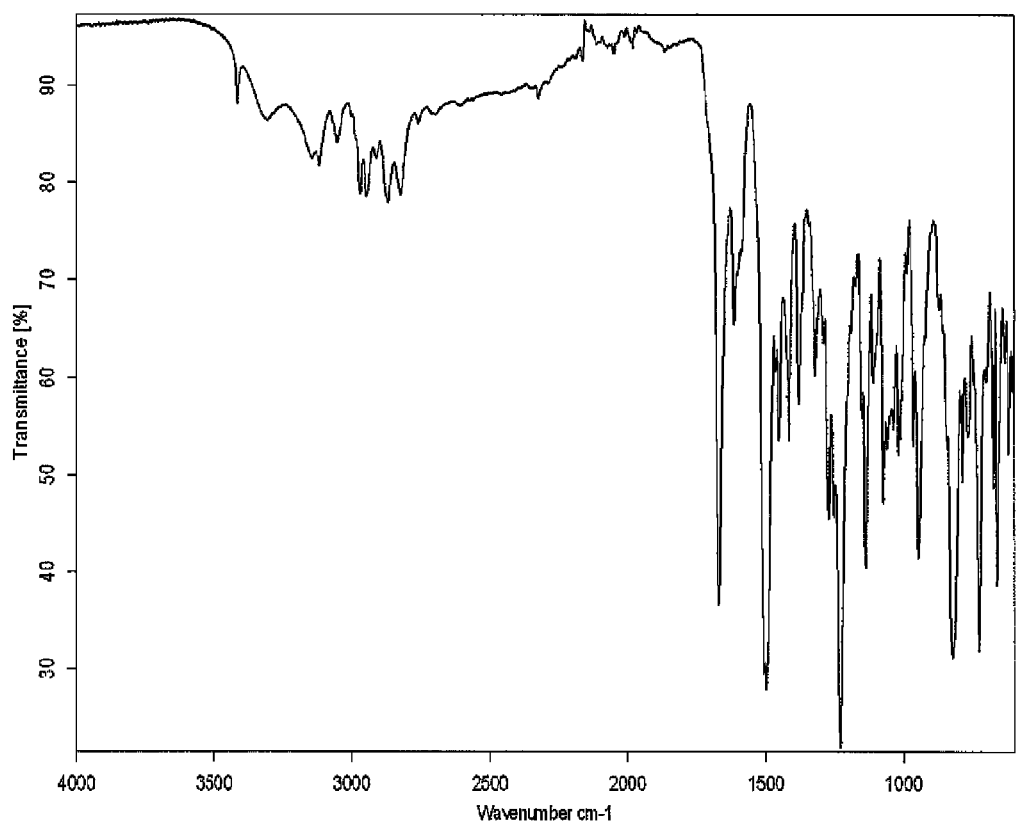

FIG. 4 shows the infrared spectrum (IR) of the compound of formula (IVb) as obtained according to Example 4 of the present invention. In FIG. 4, transmittance in % is presented on the y-axis, while wavenumber cm$^{-1}$ is presented on the x-axis. The following IR peaks can be seen in particular: 3416, 3118, 2870, 1671, 1618, 1498, 1415, 1380, 1227, 1135, 1072, 947, 823, 728 and 663+/−2 cm$^{-1}$.

Figure 5:
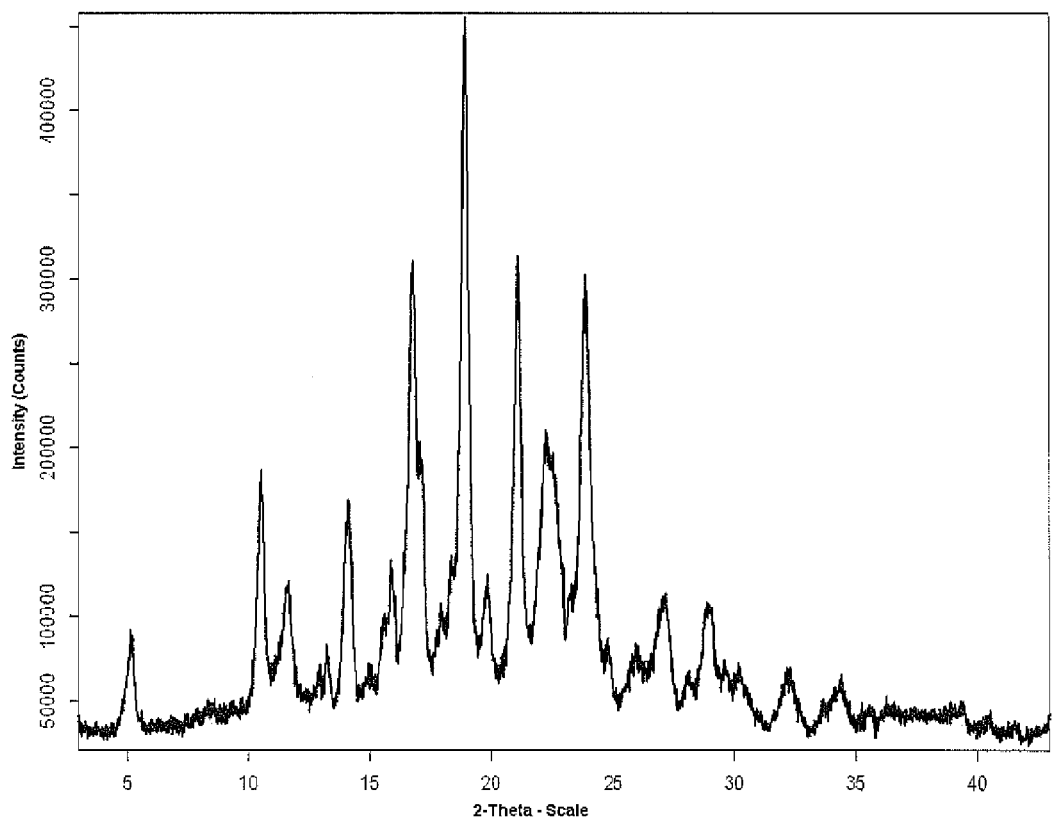

FIG. 5 shows the X-ray diffraction pattern of the compound of formula (IVb) as obtained according to Example 4 of the present invention. In FIG. 5, intensity—measured as counts per 300 seconds (linear scale)—is presented on the y-axis, while the position—expressed as 2 theta values in degrees— is presented on the x-axis. The following XRD peaks can be seen in particular: 5.1, 10.5, 11.6, 14.1, 16.8, 18.9, 19.8, 21.1, 22.2 and 23.8+/−0.2 0 2-Theta.

DETAILED DESCRIPTION

As mentioned above, the present invention relates to a process for the preparation of a chiral compound wherein said process comprises the steps of (1.1) providing a compound of formula (I)

Y₃—NH₂    (I)

or a salt thereof, wherein $Y_3$ is an optionally substituted aryl residue;
(1.2) providing a compound of formula (IIa)

$$O=C=N-Y_0 \qquad (IIa)$$

or phosgene or a phosgene derivative of formula (IIb)

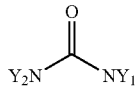

(IIb)

wherein $Y_0$ is an optionally substituted alkyl or aryl residue, and
wherein $Y_1N$— and $Y_2N$— are the same or different optionally substituted nitrogen heterocycle moieties, preferably selected from the group consisting of imidazolyl and benzimidazolyl;
(1.3) providing a compound of formula (III)

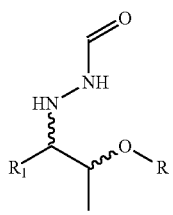

(III)

or a salt thereof,
wherein $R_1$ is an alkyl residue preferably having from 1 to 6 carbon atoms, and
wherein —R is —H or a suitable hydroxyl protecting group preferably selected from the group consisting of —$SiR_aR_bR_c$ and optionally substituted alkyl, aryl, alkaryl or aralkyl residues, where $R_a$, $R_b$ and $R_c$ are the same or different and selected from the group consisting of optionally suitably substituted alkyl and aryl residues;
(2) mixing and reacting the compounds of formulae (I), (IIa) and/or (IIb), and (III) in a solvent in any order to obtain a reaction mixture containing a chiral compound of formula (IV) and/or formula (V)

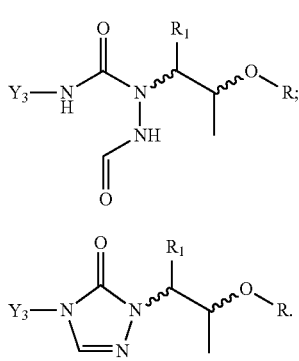

Step (1.1)—Providing a Compound of Formula (I)
According to step (1.1) of the present invention, a compound of formula (I)

$$Y_3-NH_2 \qquad (I)$$

wherein $Y_3$ is an optionally substituted aryl residue and/or a suitable salt thereof is provided. No specific restrictions exist provided that the compound of formula (I) and/or the suitable salt thereof can be used to be suitably mixed and reacted according to step (2) of the present invention.

The term "optionally substituted aryl residue" as used in the context of the present invention refers to aryl residues which have for example, up to 6 or up to 12 carbon atoms. If such aryl residue is a substituted aryl residue, the number of carbon atoms refers to the number of carbon atoms of the corresponding unsubstituted aryl residue. According to preferred embodiments of the present invention, optionally substituted aryl residues are chosen so as to allow for the preparation of compounds which may be used as antifungal agent. More preferably, $Y_3$ is a suitably substituted aryl residue, more preferably a suitably substituted phenyl residue. Most preferably, the compound of formula (I) is a chiral compound of formula

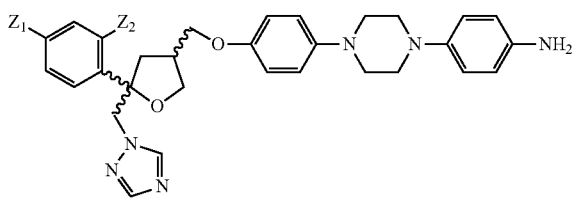

wherein $Z_1$ and $Z_2$ are independently F or Cl, preferably F. Even more preferably, the compound of formula (I) is a compound of formula

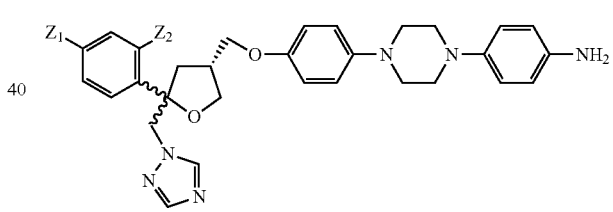

wherein $Z_1$ and $Z_2$ are independently F or Cl, preferably F, and wherein, according to an even more preferred embodiment, at least 95%, more preferably at least 97%, more preferably at least 99% of the molecules of said compound are present as isomer of formula

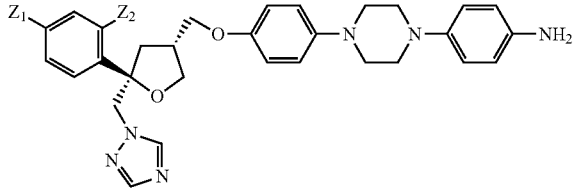

Therefore, according to a preferred embodiment of the present invention, the compound of formula (I) is a compound of formula

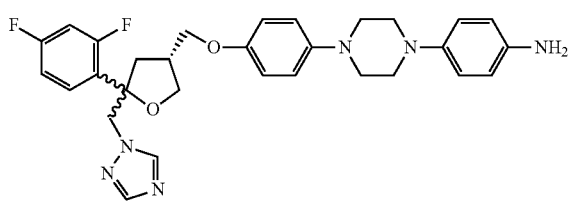

wherein at least at least 95%, more preferably at least 97%, more preferably at least 99% of the molecules of said compound are present as isomer of formula (Ia)

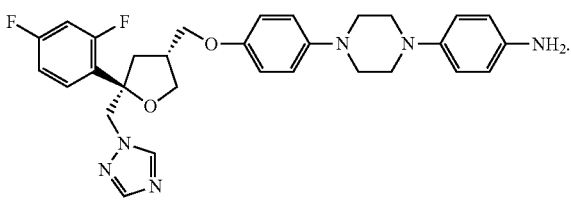

(Ia)

Thus, the present invention in particular relates to above-defined process wherein the compound of formula (I) is the compound of formula (Ia).

As far as the preparation of the compound of formula (Ia) is concerned, no particular restrictions exist. Preferably, the compound of formula (Ia) is prepared by reacting a compound of formula (A)

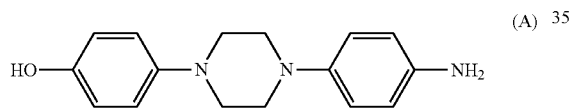

(A)

with a compound of formula (B)

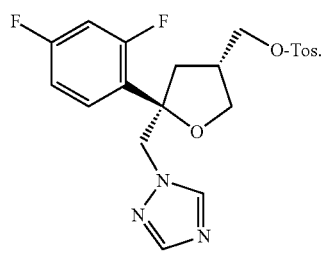

(B)

Step (1.1)—Providing a Compound of Formula (A)

As far as providing the compound of formula (A) is concerned, no particular restrictions exist. A conceivable process for the preparation of the compound of formula (A) is disclosed, for example, in M. Hepperle et. al *Tetrahedron Lett.* 2002, 43, 3359-3363, in U.S. Pat. No. 6,355,801 B1, or in EP 1 230 231 B1.

Step (1.1)—Providing a Compound of Formula (B)

As far as providing the compound of formula (B) is concerned, no particular restrictions exist. A conceivable process for the preparation of the compound of formula (B) is disclosed, for example, in U.S. Pat. No. 5,403,937, EP 0 736 030 A1, or in WO 95/17407.

According to a preferred embodiment of the present invention, the compound of formula (B) is provided by a process wherein the HCl salt of the compound of formula (GGa)

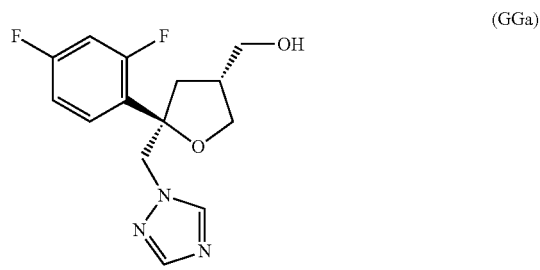 [SMILES: OC[C@@H]1CO[C@@](Cn2cncn2)(c2ccc(F)cc2F)C1]

(GGa)

is transformed into the compound of formula (B).

As far as converting the HCl salt of the compound of formula (GGa) to the respective tosylate according to formula (B) is concerned, no particular restrictions exist. According to a preferred embodiment of the present invention, the at least partially crystalline, preferably crystalline salt of the compound of formula (GG)

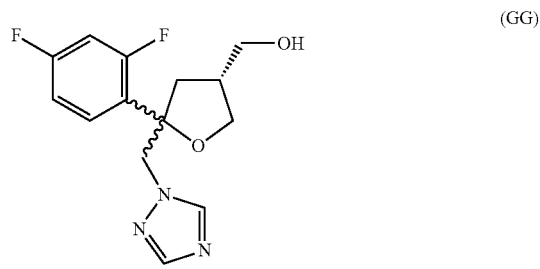

(GG)

is provided suspended in a suitable liquid, most preferably dichloromethane (DCM). To this suspension, preferably at least one suitable organic nitrogen base such as triethylamine (TEA) and/or 4-dimethylaminopyridine (DMAP) is/are added. To the resulting mixture, a suitable p-toluenesulfonyl containing compound such as p-toluenesulfonyl chloride (TsCl) is added at a preferred temperature of from 10 to 40° C. and preferably reacted for 1 to 6 hours. The obtained reaction mixture containing the compound of formula (B) is preferably suitably extracted, and from the obtained organic layer, optionally after suitable concentration, the compound of formula (B) is obtained as solid, e.g. by crystallization, which solid may be optionally suitably dried and preferably subsequently, without any further intermediate treatment, employed as starting material for the reaction with the compound of formula (A). Applying crystallization for obtaining the compound of formula (B) advantageously allows for purification of said compound as well as for a straightforward scale up of the herein described processes using said compound to a large scale production.

As far as the preparation of the HCl salt of the compound of formula (GGa) is concerned, no particular restrictions exist. According to a preferred embodiment of the present invention this HCl salt is prepared according to a process from which the HCl salt of the compound of formula (GG) is obtained, said compound of formula (GG) containing the cis-isomer of formula (GGa) and the trans-isomer of formula (GGb)

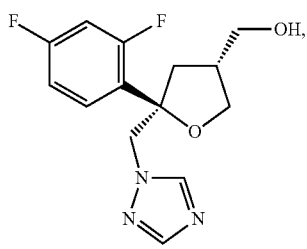
(GGa)

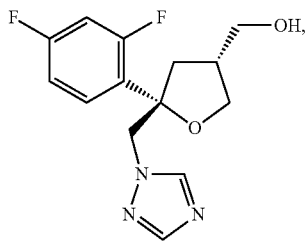
(GGb)

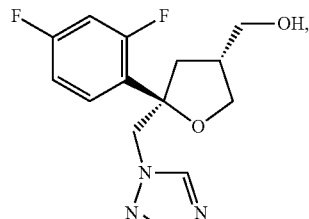
(GGa)

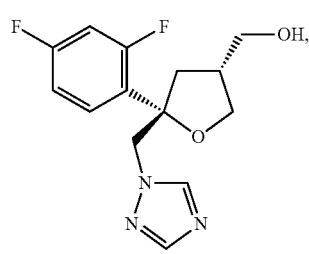
(GGb)

According to a preferred embodiment of the present invention, said preferably crystalline HCl salt contains at least 97%, preferably at least 98% and more preferably at least 99% of the HCl salt of the cis-isomer of formula (GGa) and at most 3%, preferably at most 2% and more preferably at most 1% of the HCl salt of the trans-isomer of formula (GGb).

According to an even more preferred embodiment of the present invention, said compound of formula (GG) is obtained by a process comprising (I) providing the compound of formula (GG) comprised in a first suitable solvent;

(II) treating the compound of formula (GG) comprised in the first suitable solvent with HCl comprised in a second suitable solvent to obtain the HCl salt of compound of formula (GG).

In particular, the process of providing the HCl salt of the compound of formula (GG) according to a preferred embodiment of the present invention comprises steps according to the following embodiments and the respective combinations thereof, as indicated:

1. A process for the preparation of a hydrogen chloride (HCl) salt of a compound of formula (GG)

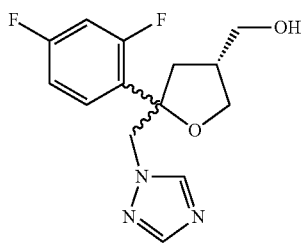
(GG)

said compound of formula (GG) containing the cis-isomer of formula (GGa) and the trans-isomer of formula (GGb) the process comprising (I) providing the compound of formula (GG) comprised in a first suitable solvent;

(II) treating the compound of formula (GG) comprised in the first suitable solvent with HCl comprised in a second suitable solvent to obtain the HCl salt of the compound of formula (GG).

2. The process of embodiment 1, wherein the compound of formula (GG) provided in (I) contains from 80 to 95%, preferably from 85 to 95% of the cis-isomer of formula (GGa) and from 20 to 5%, preferably from 15 to 5 % of the trans-isomer of formula (GGb).

3. The process of embodiment 1 or 2, wherein in (I), the compound of formula (GG) is provided by a method comprising (i.1) reacting a compound of formula (AA)

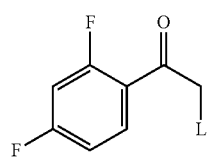
(AA)

wherein L is a leaving group, preferably a halogen, more preferably Cl, in a solvent with a nucleophilic compound comprising a nucleophilic residue $R_{aaa}R_{bbb}R_{ccc}Si$—$CH_2$ wherein $R_{aaa}$, $R_{bbb}$ and $R_{ccc}$ are the same or different and selected from the group consisting of optionally suitably substituted alkyl and aryl residues, to obtain a reaction mixture containing as intermediate a beta-hydroxy silane of formula

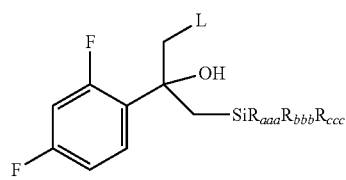

said reacting preferably being performed at a temperature in the range of from −50 to +20° C., more preferably from −30 to +10° C., more preferably from −15 to +5° C.;
(i.2) treating the resulting reaction mixture, preferably without change of solvent, with a reagent promoting elimination reaction to obtain a reaction mixture containing a compound of formula (BB)

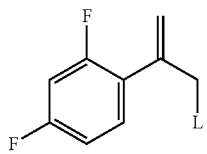
(BB)

wherein treating is performed at a temperature in the range of from −20 to +70° C. and wherein said reagent is preferably an acid, preferably an inorganic acid, more preferably sulfuric acid, wherein, if sulfuric acid is used, the temperature at which said treating is performed is preferably in the range of from 40 to 50° C.;
(ii) reacting the compound of formula (BB) with a malonic ester $R_{11}OOC—CH_2—COOR_{22}$ to obtain a compound of formula (CC)

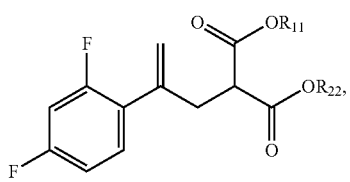
(CC)

wherein $R_{11}$ and $R_{22}$ are independently an optionally suitably substituted alkyl group having from 1 to 5 carbon atoms, preferably ethyl,
wherein, after (ii) and before (iii), the compound of formula (CC) is optionally separated by extraction in a suitable solvent, preferably cyclohexane;
(iii) reducing the compound of formula (CC) to obtain a compound of formula (DD)

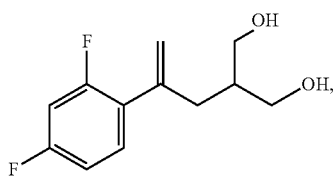
(DD)

the reducing agent preferably being $LiBH_4$ which is used in an amount of at most 2 molar equivalents with respect to the compound of formula (CC), said reduction preferably being carried out in a suitable solvent preferably comprising water, the solvent preferably being selected from the group consisting of water, alcohol, and a mixture of water and at least one alcohol, more preferably from the group consisting of water, methanol, ethanol, isopropanol, and a mixture of water and at least one of these alcohols, more preferably from the group consisting of water, etha-nol, isopropanol, and a mixture of water and at least one of these alcohols, more preferably from the group consisting of water, isopropanol, and a mixture of water and isopropanol, the solvent most preferably being a mixture of water and isopropanol, wherein the solvent preferably comprises from 1 to 20 vol.-%, more preferably from 5 to 15 vol.-% of water;
(iv) acylating the compound of formula (DD) with isobutyric anhydride to obtain a compound of formula (EE)

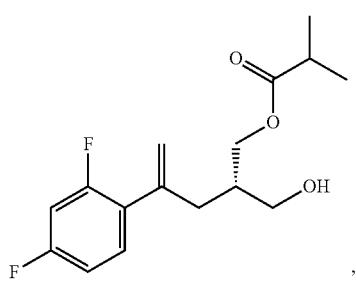
(EE)

said acylation preferably being carried out in the presence of a suitable enzyme, preferably Novo SP 435 enzyme in a suitable solvent, preferably acetonitrile or toluene, more preferably toluene,
wherein after (iv) and before (v), the compound of formula (EE) is preferably at least partially crystallized;
(v) reacting the compound of formula (EE) with a halogen $Hal_2$ selected from the group consisting of $Cl_2$, $Br_2$ and $I_2$, preferably $I_2$, in the presence of a base in a solvent to obtain a compound of formula (FF)

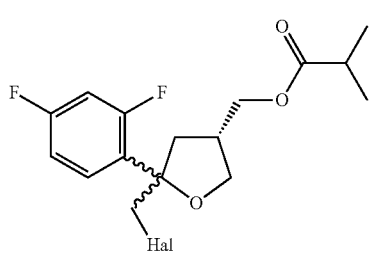
(FF)

wherein preferably from 80 to 95%, more preferably from 85 to 95% of the molecules of compound (FF) are present as cis-isomer of formula (FFa)

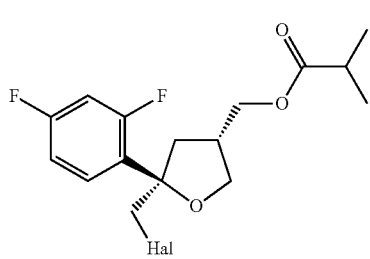
(FFa)

and preferably from 20 to 5%, more preferably from 15 to 5% of the molecules of compound (FF) are present as trans-isomer of formula (FFb)

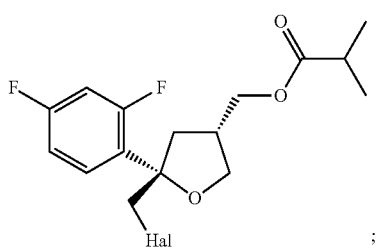

(FFb)

wherein the solvent is preferably ethyl acetate and wherein the base is preferably sodium hydrogencarbonate, and wherein the temperature at which the compound of formula (EE) is reacted is preferably less than 0° C., more preferably not higher than −5° C. and even more preferably not higher than −10° C.;

(vi.1) heating the compound of formula (FF) preferably at a temperature in the range of from +70 to +100° C., more preferably from +80 to +95° C., more preferably from +85 to +90° C., preferably in the absence of DMPU (1,3-dimethyl-3,4,5,6-tetrahydro-2(1H)-pyrimidinone), in a solvent, preferably a polar aprotic solvent, for example DMF (N,N-dimethylformamide) and DMSO, more preferably DMSO, with a 1,2,4-triazole alkali metal salt, preferably the sodium salt, and treating the resulting reaction mixture with a base suitable to promote saponification of the ester moiety such as alkali metal hydroxides, alkali metal bicarbonates, alkali metal carbonates, alkaline earth metal hydroxides, alkaline earth metal bicarbonates, and alkaline earth metal carbonates, preferably alkali metal bases, said base preferably being added in aqueous and/or alcoholic media, wherein suitable alcohols are alcohols containing 1 to 6, preferably 1 to 4, more preferably 1 to 3, most preferably 1 to 2 carbon atoms, said base even more preferably being sodium hydroxide, preferably employed as aqueous solution, in the presence of methanol, to obtain a compound of formula (GG)

(GG)

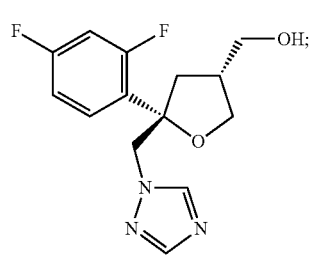

wherein preferably from 80 to 95%, more preferably from 85 to 95% of the molecules are present as cis-isomer of formula (GGa)

(GGa)

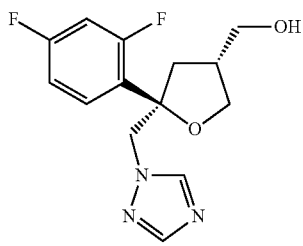

and preferably from 20 to 5%, more preferably from 15 to 5% of the molecules are present as trans-isomer of formula (GGb)

(GGb)

(vi.2) separating the compound of formula (GG) from the reaction mixture obtained from (vi.1) by extraction in a suitable solvent, the solvent preferably being a polar water-immiscible solvent, more preferably an ester such as ethyl acetate or isopropyl acetate, an ether such as tetrahydrofuran or methyl tetrahydrofuran, a ketone such as methyl isobutyl ketone, a halogenated solvent such as DCM, toluene, or a mixture of two or more of these solvents, more preferably an ester or an ether, more preferably an ether, and even more preferably methyl tetrahydrofuran.

4. The process of embodiment 3, wherein the method according to which the compound of formula (GG) is provided in (I) further comprises
   (vii) at least partially crystallizing the compound of formula (GG) after (vi.2).

5. The process of any of embodiments 1 to 4, wherein the first suitable solvent in which the compound of formula (GG) is comprised is an organic solvent, preferably an alcohol and/or a precursor of an alcohol, an ether, a ketone, an ester, or a mixture of two or more thereof.

6. The process of any of embodiments 1 to 5, wherein the first suitable solvent in which the compound of formula (GG) is comprised is selected from the group consisting of ethyl acetate, isopropyl acetate, diethyl ether, tetrahydrofuran (THF), methyl tetrahydrofuran, dioxane, methanol, n-propanol, 1-butanol, 2-butanol, 2-methyl-1-butanol, 3-methyl-1-butanol, acetone, 2-butanone, and methyl isobutyl ketone (MIBK), and wherein the second solvent is selected from the group consisting of dioxane, tetrahydrofuran (THF), diethyl ether, diisopropyl ether, methyl tert-butyl ether (MTBE), ethyl acetate, methanol, n-propanol, 1-butanol, 2-butanol, 2-methyl-1-butanol, 3-methyl-1-butanol, and toluene.

7. The process of embodiment 5 or 6, wherein the first and/or the second solvent comprise(s) an alcohol and/or a precursor of an alcohol.

8. The process of embodiment 7, wherein the first solvent is MIBK and the second solvent is THF, or wherein both the first and the second solvent is n-butanol.

9. The process of embodiment 7 or 8, wherein treating in (II) is carried out at a temperature in the range of from 20 to 100° C., preferably from 40 to 80° C., more preferably from 55 to 65° C.

10. The process of any of embodiments 7 to 9, wherein in (II), HCl comprised in the second solvent is employed relative to the compound of formula (GG) in a molar ratio HCl: (GG) in the range of from 1.0:1 to 2.0:1, preferably from 1.1:1 to 1.8:1, more preferably 1.2:1 to 1.7:1, more preferably from 1.3:1 to 1.5:1.

11. The process of any of embodiments 7 to 10, further comprising, after (II), at least partially crystallizing the HCl salt of compound of formula (GG).

12. The process of embodiment 11, wherein the at least partially crystallized HCl salt of compound of formula (GG) contains at least 97%, preferably at least 98% and more preferably at least 99% of the HCl salt of the cis-isomer of formula (GGa) and at most 3%, preferably at most 2% and more preferably at most 1% of the HCl salt of the trans-isomer of formula (GGb).

13. The process of any of embodiments 7 to 12, further comprising
    (IIa) separating the at least partially crystallized HCl salt of compound of formula (GG), preferably by filtration, optionally followed by washing with a suitable solvent, preferably with MIBK.

14. The process of any of embodiments 1 to 6, wherein treating in (II) is carried out at a temperature in the range from 0 to 100° C. and wherein in (II), HCl comprised in the second solvent is employed relative to the compound of formula (GG) in a molar ratio HCl:(GG) in the range of from 1.0:1 to 3.0:1, preferably from 1.5:1 to 2.5:1, more preferably from 2.0:1 to 2.2:1.

15. The process of embodiment 14, further comprising, after (II), at least partially crystallizing the HCl salt of compound of formula (GG).

16. The process of embodiment 15, wherein the at least partially crystallized HCl salt contains from 80 to 95%, preferably from 85 to 95% of the HCl salt of the cis-isomer of formula (GGa) and from 20 to 5%, preferably from 15 to 5% of the HCl salt of the trans-isomer of formula (GGb).

17. The process of embodiment 15 or 16, further comprising
    (IIb) separating the at least partially crystallized HCl salt of compound of formula (GG), preferably by filtration, optionally followed by washing with a suitable solvent, preferably with methyl tert-butyl ether (MTBE), acetone or methyl isobutyl ketone (MIBK), more preferably with MTBE.

18. The process of embodiment 17 or embodiment 13, further comprising
    (III) subjecting the at least partially crystallized HCl salt of compound of formula (GG) to solid extraction in a suitable solvent, preferably comprising MIBK, to obtain the HCl salt of compound of formula (GG), thereby increasing the content with regard to the HCl salt of the cis-isomer of formula (GGa).

19. The process of embodiment 18, wherein the suitable solvent is MIBK or a mixture of MIBK and an alcohol, preferably n-butanol, the molar ratio of MIBK relative to the alcohol preferably being in the range of from 0.5:1 to 10:1, more preferably from 0.75:1 to 5:1, more preferably from 0.95:1 to 1.05:1.

20. The process of embodiment 18 or 19, wherein the solid extraction is carried out at a temperature in the range of from 20 to 100° C., preferably from 40 to 80° C., more preferably from 55 to 65° C.

21. The process of any of embodiments 18 to 20, wherein in (III), the concentration of the HCl salt of compound of formula (GG) is in the range of from 0.25 to 0.75, preferably from 0.55 to 0.65 mol/liter solvent.

22. The process of any of embodiments 18 to 21, further comprising, after (III), isolating the at least partially crystallized HCl salt of compound of formula (GG).

23. The process of any of embodiments 18 to 22, wherein the at least partially crystallized HCl salt of compound of formula (GG) obtained from (III) contains at least 97%, preferably at least 98% and more preferably at least 99% of the HCl salt of the cis-isomer of formula (GGa) and at most 3%, preferably at most 2% and more preferably at most 1% of the HCl salt of the trans-isomer of formula (GGb).

24. The process of any of embodiments 18 to 23, further comprising
    (IIIa) isolating the at least partially crystallized HCl salt of compound of formula (GG) from the mixture obtained from (III), preferably by filtration, optionally followed by washing with a suitable solvent, preferably with diethyl ether or methyl tert-butyl ether (MTBE).

to 25. The process of embodiment 24, further comprising subjecting the HCl salt obtained from (IIIa) to solid extraction according to the process of any of embodiments 18 to 23, preferably followed by separating the thus obtained HCl salt according to the process of embodiment 24.

Step (1.1)—Reacting the Compound of Formula (A) with the Compound of Formula (B)

As far as the reaction of the compound of formula (A) with the compound of formula (B) is concerned, no specific restrictions exist provided that the compound of formula (I) is obtained.

Preferably, according to step (1.1) of the present invention, the compound of formula (I) is provided by a process
(aa) reacting a compound of formula (A)

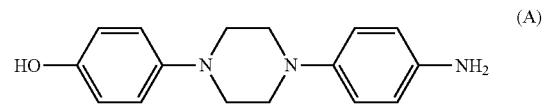

in a suitable solvent and in the presence of a suitable base, with a compound of formula (B)

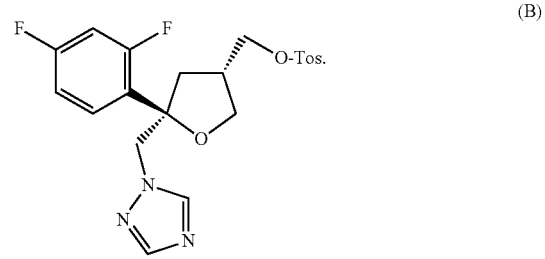

While as to the suitable solvent, no specific restrictions exist, preferred solvents according to the present invention are polar solvents. In particular, the suitable solvent is a polar protic solvent or a mixture of two or more thereof, or a polar aprotic solvent or a mixture of two or more thereof. More preferably, the suitable solvent is selected from the group consisting of dimethylsulfoxide (DMSO), dimethylformamide (DMF), N-methylpyrrolidone (NMP), sulfolane, methanol, ethanol, n-propanol, and iso-propanol, with ethanol or DMSO being particularly preferred.

Optionally, reacting in step (aa) is performed in the presence of at least one suitable anti-oxidant, such as butylated hydroxytoluene (BHT).

As to the suitable base, no specific restrictions exist provided that the compound of formula (A) and the compound of formula (B) can be reacted with each other to give the desired product. Preferred bases according to the present invention are inorganic bases, more preferably carbonates, hydroxides and/or hydrogencarbonates, and mixtures thereof. Even more preferably, the respective cations are selected from the group consisting of alkali metal ions, alkaline earth metal ions, or mixtures thereof. As alkali metals, lithium, sodium or potassium may be mentioned. As alkaline earth metals, magnesium, calcium, strontium or barium may be mentioned. Thus, a preferred base is in particular an alkali metal and/or an alkaline earth metal carbonate, an alkali metal and/or an alkaline earth metal hydroxide, and/or an alkali metal and/or an alkaline earth metal hydrogencarbonate, with sodium hydroxide and potassium carbonate being particularly preferred.

As to the preferred base sodium hydroxide, it is especially preferred to employ said base as aqueous solution. Employing an aqueous solution with a concentration of at least 20 wt.-%, preferably at least 45 wt.-% with respect to the base was found to be especially advantageous, and leads to a significant acceleration of the reaction rate as well as to increased selectivity of said reaction by reducing the formation of by-products.

With respect to the compound of formula (A), using an excess of the compound of formula (B) is preferred. Thus, the present invention relates to above-defined process wherein in step (aa), the molar ratio of the compound of formula (B) to the compound of formula (A) is greater than one. Further, preferred molar ratios are in the range of from greater than 1:1 to 1.2:1. Especially preferred molar ratios are in the range from 1.05:1 to 1, 15:1, with a molar ratio of 1.1:1 being particularly preferred.

With respect to the compound of formula (A), using an excess of base is preferred. Thus, the present invention relates to above-defined process wherein in step (aa), the molar ratio of the base to the compound of formula (A) is greater than one. Further, preferred molar ratios are in the range of from greater than 1:1 to 2.0:1, more preferably from greater than 1:1 to 1.8:1, more preferably from greater than 1:1 to 1.6:1, more preferably from greater than 1:1 to 1.5:1.

The temperature under which the reaction in (aa) is carried out can be suitably chosen. Preferred temperatures are in the range of from 20 to at most 35° C., more preferably from 25 to at most 32° C.

The pH under which the reaction in (aa) is carried out is suitably controlled by addition of above-defined base. In particular, the reaction is carried out at a pH of at least 10.

From step (aa) of the present invention, the compound of formula (I) is obtained as crystallized product contained in the reaction mixture. According to a preferred embodiment, the compound of formula (I) is suitably separated from the reaction mixture and optionally suitably washed. Said optional washing is preferably carried out with a base as washing agent wherein inorganic bases such as sodium hydroxide are preferred. Base concentrations of from 0.1 to 5 wt.-%, are preferred, with 0.5 to 2 wt.-% being particularly preferred. Additionally, the compound of formula (I) may be further washed at least once with water and/or at least once with a suitable alcohol such as isopropanol.

While in general, the thus obtained product may be used for further steps without further treatment, it is preferred, according to the present invention, to re-crystallize the product obtained from step (aa). Therefore, the present invention relates to above-defined process which further comprises (bb) re-crystallizing the compound of formula (I).

While every suitable re-crystallization method is conceivable, it is especially preferred to re-crystallize the compound of formula (I) at least once from acetonitrile and/or water. It was found that compared to the isolation from water, the product obtained from re-crystallization from acetonitrile can be much easier dried, and thus, re-crystallization from acetonitrile allows for milder post-treatment conditions.

Drying of the thus re-crystallized compound of formula (I) is preferably carried out at a temperature of at most 75° C., preferably of at most 70° C. at a pressure of preferably at most 500 mbar, more preferably of at most 100 mbar, more preferably of at most 75 mbar.

Most preferably, either re-crystallization, or drying, or re-crystallization and drying is/are carried out under inert atmosphere such as under nitrogen atmosphere.

Optionally, the product may be treated with a suitable porous material to remove remaining impurities. Among others, charcoal may be mentioned as such suitable material.

Step (1.2)—Providing a Compound of Formula (IIa) or (IIb)

According to step (1.2) of the process of the present invention, a compound of formula (IIa)

or (IIb)

is provided.

As far as the compound of formula (IIa) is concerned, the residue $Y_0$ is an optionally substituted alkyl or aryl residue. The term "optionally substituted aryl residue" as used in this context of the present invention refers to aryl residues which have, for example, up to 6 or up to 12 carbon atoms. If such aryl residue is a substituted aryl residue, the number of carbon atoms refers to the number of carbon atoms of the corresponding unsubstituted aryl residue. The term "optionally substituted alkyl residue" as used in this context of the present invention refers to straight or branched alkyl residues which have, for example, 1 to 20, preferably 1 to 10 carbon atoms. If such alkyl residue is a substituted alkyl residue, the number of carbon atoms refers to the number of carbon atoms of the corresponding unsubstituted alkyl residue. As preferred compound of formula (IIa), phenylisocyanate may be mentioned.

As far as the compound of formula (IIb) is concerned, the residues $Y_1N$— and $Y_2N$— are the same or different and are optionally substituted nitrogen heterocycle moieties. The term "nitrogen heterocycle" as used in the context of the present invention relates to a cyclic residue which contains at least one, preferably one, two or three, more preferably two nitrogen atoms. The cyclic structure as such preferably contains from five to ten atoms in total, preferably from five to nine atoms in total. Especially preferred residues $Y_1N$— and $Y_2N$— are imidazolyl or benzimidazolyl. According to an especially preferred embodiment of the present invention, the compound of formula (IIb) is carbonyldiimidazole (CDI) of formula (IIc)

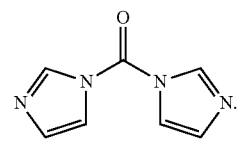

Typically, the compound of formula (IIb) is employed contained in a suitable solvent or in a mixture of two or more suitable solvents. Such suitable solvent is, for example, DCM, THF, Me-THF, DMF, acetonitrile, an ester like ethyl acetate or butyl acetate, with DCM being especially preferred.

Step (1.3)—Providing a Compound of Formula (III)

According to step (1.3) of the present invention, a compound of formula (III)

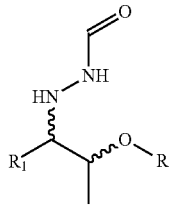
(III)

or a suitable salt thereof is provided.

In the compound according to formula (III), the residue $R_1$ is preferably a straight or branched alkyl residue which preferably has from 1 to 6 carbon atoms, namely 1, 2, 3, 4, 5, or 6 carbon atoms, more preferably from 1 to 4 carbon atoms, namely 1, 2, 3, or 4 carbon atoms, more preferably 1 or 2 carbon atoms, in particular 2 carbon atoms.

Further, in the compound of formula (III), the residue —R is either —H or a suitable hydroxyl protecting group. Conceivable protecting group are given, for example, in Greene et al., "Protective Groups in Organic Synthesis", $3^{rd}$ Ed., Wiley-Interscience (1999).

Preferably, the suitable hydroxyl protecting group is benzyl or a group —$SiR_a,R_bR^c$, wherein the residues $R_a$, $R_b$ and $R_c$ may be the same or different and are preferably alkyl or aryl residues. The term "aryl residue" as used in this context of the present invention relates to a carbocyclic aromatic group, such as phenyl or naphthyl or the like. The term "alkyl residue" as used in the context of the present invention relates to straight or branched alkyl moieties which preferably have 1, 2, 3, 4, 5, or 6 carbon atoms, more preferably 1, 2 or 3 carbon atoms, more preferably 1 carbon atom. Especially preferably, the residue —R is —H or a hydroxyl protecting group selected from the group consisting of —$Si(CH_3)_3$ and benzyl, —R most preferably being —H.

Even more preferably, the compound of formula (III) is provided as crystalline compound with a specific amount of molecules present as compound of the formula

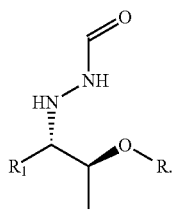

Thus, the present invention relates to above-defined process wherein the compound of formula (III) is a preferably crystalline compound

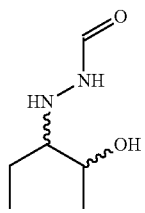
(IIIa)

and wherein, according to further preferred embodiment, at least 95%, preferably at least 97%, more preferably at least 99% of the molecules of said crystalline compound are present as compound of formula (IIIb)

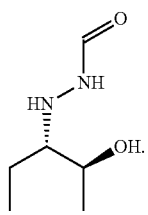
(IIIb)

Generally, there are no specific restrictions as far as the preparation of the compound of formula (III), in particular of formula (IIIa) is concerned.

According to a preferred process, the compound of formula (III) wherein —R=—H or a residue —$SiR_a,R_bR_c$ is provided in step (1.3) of the present invention by a process which comprises the following steps:

(a) providing a chiral compound of formula (i)

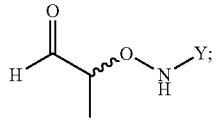
(i)

wherein Y is an optionally substituted aryl moiety, preferably an optionally substituted phenyl moiety, more preferably unsubstituted phenyl, said providing in (a) preferably comprising reacting propionaldehyde in a solvent with a compound of formula (j)

O=N—Y (j), preferably with nitrosobenzene, in the presence of a catalyst system preferably comprising at least one organocatalyst, more preferably proline (Pro), more preferably D-Pro, said catalyst system optionally further comprising a promoter, preferably an urea derivative, more preferably 1-(2-dimethylamino-ethyl)-3-phenyl urea, wherein preferably at least 95%, more preferably at least 97%, more preferably at least 99% of the molecules of the chiral compound of formula (I) provided in (a) are present as

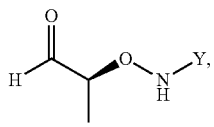

(ia)

said reaction of propionaldehyde with the compound of formula (j) preferably being carried out at a temperature in the range of from −15 to +5° C., preferably from −12 to +3° C., more preferably from −10 to 0° C., preferably in dichloromethane as solvent, and preferably in the presence of a catalytical amount of an acid, preferably acetic acid or propionic acid;

(b) reacting the compound of formula (I) with $H_2N$—NH—CHO in a solvent, preferably dichloromethane, to obtain a compound according to formula (ii)

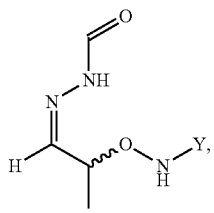

(ii)

wherein said reacting is preferably carried out in the presence of a molecular sieve, preferably having a pore diameter determined according to DIN 66131 in the range of from 0.3 to 0.5 nm (nanometre, 3 to 5 Angstrom), and wherein said reacting is preferably carried out at a temperature in the range of from −10 to +20° C., preferably from −5 to +5° C.;

(c) separating the compound of formula (ii) from the reaction mixture obtained from (b) by solvent extraction, wherein prior to (c), a solvent exchange is preferably carried out;

(d) optionally reacting the compound of formula (ii) in a solvent, preferably at a temperature in the range of from 15 to 70° C., with a silylating agent comprising the residue —$SiR_{aa}R_{bb}R_{cc}$ to obtain a compound of formula (iii)

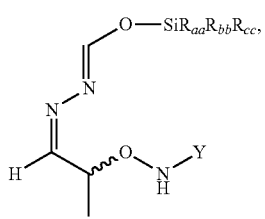

(iii)

wherein the residues $R_{aa}$, $R_{bb}$ and $R_{cc}$ may be the same or different and are preferably alkyl or aryl residues, more preferably alkyl residues having from 1 to 6 carbon atoms, preferably from 1 to 4 carbon atoms, more preferably 1 or 2 carbon atoms, and wherein the silylating agent is preferably hexamethyldisilazane, trimethylchlorosilane, bistrimethylsilylacetamide or a mixture of two or three of these compounds, more preferably bistrimethylsilylacetamide;

(e) reacting the compound of formula (II) or reacting the compound of formula (iii) with a nucleophilic compound comprising a nucleophilic residue $R_1$, the nucleophilic compound preferably being a Grignard compound $R_1MgX$ wherein X is preferably selected from the group consisting of Cl, Br, and I, and wherein $R_1$ is preferably an alkyl residue preferably having from 1 to 6 carbon atoms, more preferably from 1 to 4 carbon atoms, more preferably 1 or 2 carbon atoms, most preferably 2 carbon atoms, in a solvent, preferably selected from the group consisting of toluene, tetrahydrofurane (THF), MTBE, and a mixture of THF and MTBE, to obtain a compound of formula (iv)

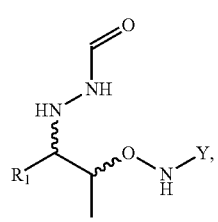

(iv)

wherein the nucleophilic compound is preferably $CH_3CH_2MgCl$, wherein the reaction with the nucleophilic compound is preferably carried out at a temperature in the range of from −80 to 0° C., preferably from −75 to −10° C., more preferably from −70 to −25° C.;

(f) reducing the compound of formula (iv), preferably by hydrogenation, wherein preferably a solvent mixture comprising an alcohol comprising 1 to 4 carbon atoms, preferably methanol, ethanol, isopropanol, most preferably methanol, is employed, to obtain a compound of formula (III) with R=H

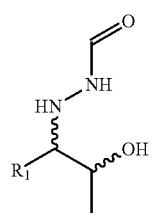

wherein the hydrogenation is preferably carried out at a temperature in the range of from 15 to 35° C., preferably from 20 to 30° C., at a hydrogen pressure in the range of from 0.5 to 50 bar, preferably from 1 to 20 bar, more preferably from 1 to 10 bar, in the presence of a precious metal containing catalyst, preferably a palladium containing catalyst, most preferably a Pd/C catalyst;

(g) optionally crystallizing the compound of formula (III) with R=H, wherein the compound of formula (III) is preferably crystallized from a mixture of MTBE and cyclohexane (CHX);
(h) optionally recrystallizing the compound of formula (III) with R=H, wherein the compound of formula (III) with R=H is preferably recrystallized from isopropyl acetate;
(i) optionally reacting the optionally crystallized compound of formula (III) with R=H in a solvent with a silylating agent comprising the residue —SiR$_a$R$_b$R$_c$ to obtain a compound of formula (III) with R=SiR$_a$R$_b$R$_c$

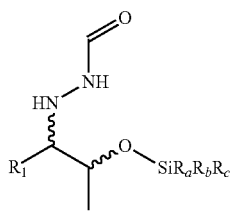

wherein the residues R$_a$, R$_b$ and R$_c$ are as defined above.

Step (2)—Mixing and Reacting the Compounds of Formulae (I), (IIa) and/or (IIb), and (III)

As to step (2) of the present invention, the compounds of formulae (I), (IIa) and/or (IIb), preferably (IIb), and (III) can be mixed in any suitable order wherein each of said compounds can be employed as such or contained in at least one suitable solvent or in a suitable solvent mixture.

According to a preferred embodiment of the present invention, in a first step (2.1), the compounds of formulae (I) and (IIa) and/or (IIb), preferably (IIb), are mixed and at least partially reacted in a solvent to obtain a reaction mixture.

No particular restrictions exist concerning the solvent in which the reaction in step (2) and/or in step (2.1) is carried out. Preferably, the solvent is a polar aprotic solvent or a mixture of two or more thereof. More preferably, the at least one solvent is selected from the group consisting of dichloromethane (DCM), tetrahydrofurane (THF), methyl tetrahydrofurane (MeTHF), dimethyl formamide (DMF), acetonitrile (AN), an ester, preferably butylacetate (BuAc) or ethylacetate (EtAc), and a mixture of two or more thereof, preferably DCM or THF. Especially preferably, the solvent is DCM.

As described above, it is particularly preferred to employ the compound of formula (IIa) and/or (IIb), preferably (IIb), contained in DCM. As to the compound of formula (I), it is conceivable to introduce it either as solid compound, as, for example, obtained according to step (bb) described above wherein the compound of formula (I) is re-crystallized, preferably from acetonitrile, or contained in a suitable solvent such as DCM. According to a preferred embodiment of the present invention, the compound of formula (I) is introduced as solid compound obtained from step (bb) into the solution containing the compound of formula (IIa) or (IIb) wherein DCM is the most preferred solvent.

Preferably, the compound of formula (IIa) or (IIb) and the compound of formula (I) are employed in a molar ratio so that the compound of formula (IIa) or (IIb) is used in excess. Preferably, said molar ratio is in the range of from greater than 1:1 to 1.3:1, more preferably from greater than 1:1 to 1.2:1, more preferably from 1.05:1 to 1.15:1 such as 1.1:1.

After step (2.1), it is preferred to add the compound of formula (III) to the reaction mixture obtained from step (2.1).

As to the compound of formula (III), it is conceivable to introduce it either as solid compound, as, for example, obtained according to step (h) described above wherein the compound of formula (III) is recrystallized, preferably from isopropyl acetate, or contained in a suitable solvent such as DCM, THF or, preferably, a mixture thereof. According to a preferred embodiment of the present invention, the compound of formula (III) is introduced as solid compound obtained from step (h) into the reaction mixture obtained from step (2.1).

Preferably, the compound of formula (III) is employed, relative to the compound of formula (I), in a molar ratio so that the compound of formula (III) is used in excess. Preferably, said molar ratio is in the range of from greater than 1:1 to 1.3:1, more preferably from greater than 1:1 to 1.2:1, more preferably from 1.05:1 to 1.15:1 such as 1.1:1.

The temperature under which the reaction in step (2) is carried out, is preferably in the range of from −20 to +40° C. More preferably, the reaction in step (2.1) is carried out at a temperature in the range of from −20 to +20° C., more preferably from −15 to 0° C., more preferably from −10 to −5° C. The reaction according to step (2.2) of the present invention is preferably carried out at a temperature in the range of from −20 to +40° C., more preferably, in a first reaction period, in the range of from −20 to 0° C., more preferably from −15 to 0° C., more preferably from −15 to −5° C., and, in a subsequent reaction period, in the range of from −5 to +40° C., preferably from 15 to 40° C., more preferably from 25 to 35° C., most preferably 30° C.

Generally, the compound of formula (IV) can be crystallized from at least one suitable solvent, for example, from acetonitrile. Preferably, according to the present invention, the compound of formula (IV) is crystallized directly from the reaction mixture. For example, in a subsequent reaction period, the reaction mixture described above is preferably suitably cooled to initiate crystallization of the compound of formula (IV), wherein the reaction mixture is preferably cooled to initiate crystallization and subsequently further cooled to a temperature in the range of from −10 to +5° C., more preferably from −5 to +5° C. Seed crystals may be added to initiate crystallization.

Therefore, the present invention relates to above-defined process comprising isolating the chiral compound of formula (IV)

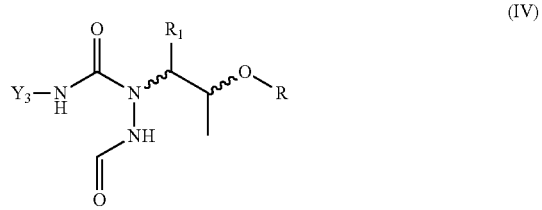

from the reaction mixture obtained from (2).

As described, said isolating is preferably carried out by crystallization. Further, it is also conceivable to isolate the compound of formula (IV) by chromatography.

From the reaction in step (2), the suitably isolated, preferably crystallized compound of formula (IV) is obtained.

After separation from its mother liquor, the crystallized compound of formula (IV) can be suitably washed at least once and optionally dried.

According to a preferred embodiment of the present invention, the compound of formula (IV) being a compound of formula (IVb), in particular being a compound of formula (IVd) as herein described, is crystallized directly from the reaction mixture preferably containing imidazol and a solvent such as preferably DCM, and by applying the above described reaction periods and conditions.

Surprisingly, it was found that in case the compound of formula (IVb), in particular the compound of formula (IVd) is directly crystallized from the reaction mixture in particular containing DCM and imidazole, the compound of formula (IVb), in particular the compound of formula (IVd) may crystallize as adduct compound of formula (IVd):imidazole:DCM for example as 1:1:1 adduct, wherein said adduct is obtained in at least one polymorphic form.

After separation from its mother liquor, the crystallized compound of formula (IVd) can be suitably washed at least once and optionally dried. The product can be recrystallized from DCM to give the same 1:1:1 adduct as described above, or from acetonitrile to give an 1:1 adduct with imidazole.

The procedure of crystallizing the compound of formula (IVd) as adduct directly from the reaction mixture as described above leads to an improved process, because it avoids the application of complex technical requirement, and it allows an easy isolation of the crystalline product moreover resulting in low amounts of impurities in the isolated product as well as in high yields of said product.

Depending on the specific crystallization conditions and/or the components contained in the reaction mixture, also other adducts are conceivable each possibly being present in at least one polymorphic form.

Thus, the present invention also relates to an optionally crystalline chiral compound of formula (IVa)

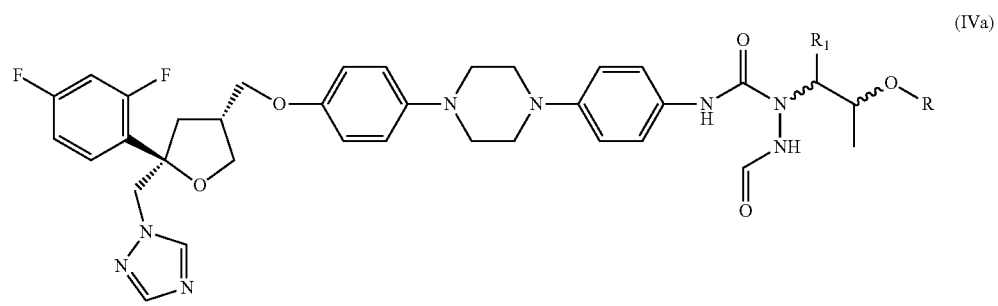

(IVa)

or a salt thereof, wherein $R_1$ is an alkyl residue preferably having from 1 to 6 carbon atoms, more preferably from 1 to 4 carbon atoms, more preferably 1 or 2 carbon atoms, most preferably 2 carbon atoms, $R_1$ in particular being ethyl, and wherein —R is —H or a suitable hydroxyl protecting group preferably selected from the group consisting of —$SiR_aR_bR_c$ and optionally substituted alkyl, aryl, alkaryl or aralkyl residues, where $R_a$, $R_b$ and $R_c$ are the same or different and selected from the group consisting of optionally suitably substituted alkyl and aryl residues, with —R preferably being —H or a hydroxyl protecting group selected from the group consisting of —$Si(CH_3)_3$ and benzyl, —R in particular being —H, and wherein said compound is most preferably a compound of formula (IVb)

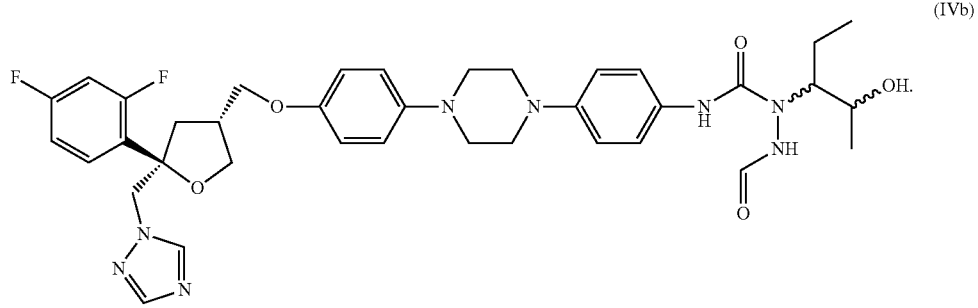 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

(IVb)

According to an even more preferred embodiment, at least 95%, preferably at least 97%, more preferably at least 99% of the molecules of said compound of formula (IVb) are present as compound of formula (IVc)

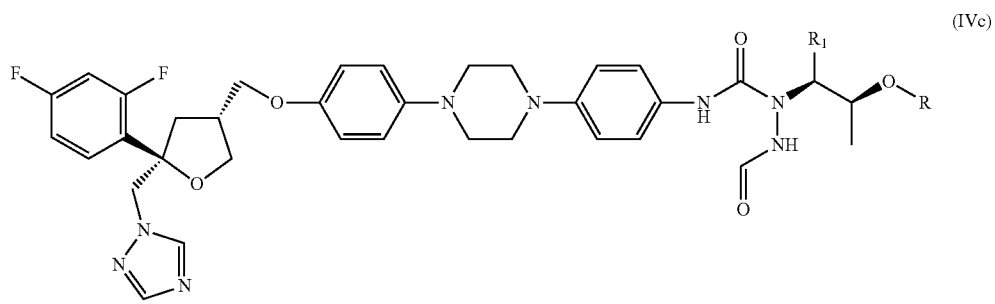

most preferably as compound of formula (IVd)

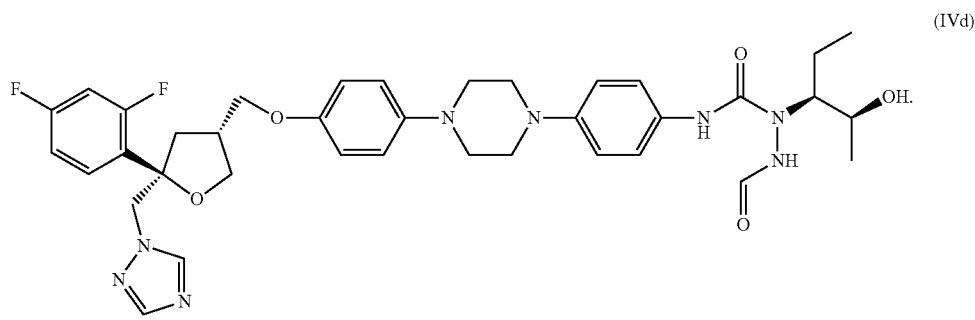 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

According to an optional embodiment of the present invention, the reaction in step (2) can be carried out in the presence of an acid which is either employed in stoichiometric or preferably employed in a substoichiometric amount. Typically, the acid used is at least partially soluble in the solvent or solvent mixture employed in step (2). Most preferably, the acid is trifluoroacetic acid (TFA) or para-toluenesulfonic acid (PTSA), with trifluoroacetic acid (TFA) being especially preferred.

However, as indicated, reacting in step (2) can be carried out in the absence of trifluoroacetic acid (TFA), preferably in the absence of trifluoroacetic acid (TFA) or para-toluenesulfonic acid (PTSA), more preferably in the absence of an acid.

As described above, the process of the present invention, compared to known processes of the prior art, in particular compared to known processes for the preparation of posaconazole, is characterized in that it is carried out in the absence of a compound of formula Cl—C(═O)—O-Ph (phenyl chloroformate), in particular in the absence of an ester of a halogenated formic acid. Thus, the use of mutagenic compounds is avoided which may be found in the final product or the pharmaceutical composition containing such product.

Step (3)—Heating the Mixture Obtained from Step (2)

According to a first preferred embodiment of the present invention, the reaction mixture obtained from step (2), without isolation of the compound of formula (IV) is subjected to a heating step (3).

Optionally, prior to heating, the solvent present in the reaction mixture obtained from step (2), can be exchanged by at least one further solvent. Preferably, the reaction mixture obtained from step (2) contains a solvent selected from the group consisting of dichloromethane (DCM), tetrahydrofurane (THF), methyl tetrahydrofurane (MeTHF), acetonitrile (AN), an ester, preferably butylacetate (BuAc) or ethylacetate (EtAc) and dimethylformamide (DMF), and a mixture of two or more thereof, preferably DCM or THF, in particular DCM. If solvent exchange is carried out, the solvent described above are exchanged by a solvent allowing for the heating conditions of step (3) described in detail hereinunder. Preferably, such solvent preferably used for heating in step (3) is selected from the group consisting of toluene, benzene, an ester of a saturated carboxylic acid, preferably isopropyl acetate, dimethylformamide (DMF), acetonitrile (AN), methyltetrahydrofurane (Me-THF), methylisobutylketone (MIBK), dioxane, hexamethyldisilazane (HMDS) and a mixture of two or more thereof, preferably toluene or isopropyl acetate.

According to a second preferred embodiment, the compound of formula (IV) is suitably isolated after step (2), preferably by crystallization. As to this embodiment of the present invention, the isolated, preferably crystallized compound of formula (IV) is admixed with a suitable solvent prior to heating in step (3), wherein the solvent is preferably selected from the group consisting of toluene, benzene, an ester of a saturated carboxylic acid, preferably isopropyl acetate, dimethylformamide (DMF), acetonitrile (AN), methyltetrahydrofurane (Me-THF), methylisobutylketone (MIBK), dioxane, hexamethyldisilazane (HMDS) and a mixture of two or more thereof, preferably toluene or isopropyl acetate.

The temperature to which such mixture is heated in step (3) is preferably in the range of from 40 to 150° C., preferably from 60 to 140° C., more preferably from 70 to 130° C. Typical temperatures will be in the range of from 70 to 80 or from 80 to 90 or from 90 to 100 or from 100 to 110 or from 110 to 120 or from 120 to 130° C.

According to a preferred embodiment of the present invention, prior to heating according to step (3), the compound of formula (IV), either as contained in the reaction mixture obtained from step (2) with an optional subsequent solvent exchange as described above, or as contained in the mixture obtained from suitably isolating the compound of formula (IV) and admixing the isolated compound with a suitable solvent as described above, is admixed and reacted with a suitable silylating agent. Such admixing with a silylating agent is particularly preferably carried out if the residue —R as described above is —H, i.e. in case the respective hydroxyl group of the compound of formula (III) is employed in its non-protected form.

No particular restrictions exist as to such silylating agent. A conceivable silylating agent is, for example, a trialkylsilylhalide, more preferably a trialkylsilylchloride and/or a trialkylsilyliodide, in particular trimethylsilylchloride (TMSCl) and/or trimethylsilyliodid (TMSI). According to a preferred embodiment of the present invention, bis-trimethylsilylacetamide (BSA) is used as silylating agent. Optionally, in particular if BSA is used, reaction of the compound of formula (IV) with the silylating agent is performed in the presence of a suitable acid, preferably a Lewis acid, more preferably a silicon-containing Lewis acid, in particular trimethylsilyl iodide (TMSI).

Relative to the compound of formula (IV), the silylating agent is preferably employed in excess. Preferred molar ratios of the silylating agent relative to the compound of formula (IV) are in the range of from greater than 1:1 to 3:1, more preferably from greater 1.45:1 to 2.7:1, more preferably from greater 1.5:1 to 2.1:1, more preferably from 1.9:1 to 2.1:1, most preferably 2:1.

Relative to the compound of formula (IV), the acid, preferably the Lewis acid, is preferably employed in substoichiometric amount. Preferred molar ratios of the Lewis acid, preferably TMSI, relative to the compound of formula (IV) are in the range of from 0.05 to less than 1:1, preferably from 0.1 to 0.5, more preferably from 0.15 to 0.25, most preferably 0.2.

As mentioned above, in case the most preferred compound CDI is employed, the compound of formula (IV) as obtained after solvent exchange or after crystallization and admixing with solvent will typically contain imidazole, generally in the range of from 1 to 10 wt.-%, preferably from 2 to 10 wt.-%, more preferably from 4 to 10 wt.-%, more preferably from 6 to 10 wt.-%. According to an especially preferred embodiment of the present invention, imidazole is added to the compound of formula (IV) in order transform the compound of formula (IV) to the compound of formula (V). Therefore, since imidazole is already contained in the compound of formula (IV) due to the use of CDI, only a lesser amount of imidazole has to be added. At this stage, imidazole is added in amount so that, relative to the compound of formula (IV), imidazole is present in excess wherein preferred molar ratios of imidazole relative to the compound of formula (IV) are in the range of from 2:1 to 10:1, more preferably from 4:1 to 9.5:1, more preferably from 7:1 to 8:1, most preferably 7.5:1.

Most preferably, imidazole is added prior to admixing the compound of formula (IV) with the silylating agent as described above.

From the compound of formula (IV), after heating in step (3), preferably after addition of imidazole, and optionally after addition of the silylating agent, the compound of formula (V) is obtained, preferably contained in a solvent selected from the group consisting of toluene, benzene, an ester of a saturated carboxylic acid, preferably isopropyl acetate, dimethylformamide (DMF), acetonitrile (AN), methyltetrahydrofurane (Me-THF), methylisobutylketone (MIBK), dioxane, hexamethyldisilazane (HMDS) and a mixture of two or more thereof, preferably toluene or isopropyl acetate.

Step (4)—Extracting the Compound of Formula (V)

According to a further preferred embodiment of the present invention, the compound of formula (V) contained in abovementioned solvent is subjected to suitable solvent extraction.

For solvent extraction, an aqueous acid is preferably used as extracting agent wherein said aqueous acid is preferably an aqueous inorganic acid and more preferably aqueous hydrochloric acid. The concentration of the aqueous inorganic acid, preferably the aqueous hydrochloric acid, is preferably in the range of from 5 to 15 wt.-%. The temperature under which the extracting agent is added is preferably in the range of from 10 to 50° C., preferably from 20 to 40° C. The thus obtained layers are separated.

Preferably, the acidic aqueous layer which contains the compound of formula (V) is is subjected to a further solvent extraction wherein at least one suitable organic solvent, in particular DCM is used. The pH of the thus obtained aqueous layer is preferably adjusted to a value in the range of from 0.8 to 1.5, preferably from 1 to 1.2 using a suitable amount of at least one suitable base, preferably an inorganic base, more preferably an inorganic hydroxide, more preferably an aqueous sodium hydroxide solution. The thus obtained layers are separated.

Preferably, the organic layer thus obtained which contains the compound of formula (V) is subjected to a suitable washing treatment. Every conceivable washing agent or combination of washing agents can be used. According to a preferred embodiment of the present invention, the organic layer is washed with an acid, preferably an inorganic acid, more preferably hydrochloric acid, more preferably aqueous hydrogen chloride, and further washed with a base, preferably an inorganic base, more preferably an alkali hydrogen carbonate, more preferably sodium hydrogen carbonate. Preferably, the organic layer is first washed with the acid and subsequently washed with the base. The thus obtained layers are separated.

Preferably, the organic layer thus obtained and containing the compound of formula (V) is suitably concentrated in one, two or more individual concentration steps wherein between two subsequent concentration steps, at least one solvent such as acetone or methanol, preferably acetone can be added.

The finally obtained concentrated organic layer is preferably admixed with water at a temperature which is preferably in the range of from 15 to 40° C., more preferably from 20 to 30° C. Optionally, the thus obtained suspension may be subjected to a treatment with a suitable porous material to remove remaining impurities. Among others, charcoal may be mentioned as such suitable material.

After solvent extraction and preferred post-treatment steps as described, the preferred resulting suspension contains the compound of formula (V) in solution. The compound of formula (V) is preferably suitably separated from the above-mentioned suitable porous material, for example via filtration. The filter cake preferably containing above-mentioned suitable porous material such as charcoal is preferably washed with a suitable solvent or solvent mixture. Suitable washing agents are, for example, mixtures of acetone or methanol with water. The filtrate and the washing liquids, containing the compound of formula (V), are preferably combined.

According to a preferred embodiment, the compound of formula (V) preferably contained in the combined filtrate and washing liquids, is suitably crystallized in step (5) of the present invention and optionally separated from its mother liquor in a step (6) of the present invention.

Step (5)—Crystallizing the Compound of Formula (V)

According to step (5), the compound of formula (V) is suitably crystallized in a solvent or in a mixture of two or more solvents.

No particular restrictions exist concerning the solvent provided that the compound of formula (V) can be crystallized. Preferably, crystallizing in (5) is carried out in a solvent which is selected from the group consisting of alcohols, preferably methanol, ethanol, n-propanol, iso-propanol, ethers, preferably THF, ketones, preferably acetone, acetonitril, and a mixture of two or more thereof, most preferably admixed with water, the solvent most preferably being methanol admixed with water or acetone admixed with water.

Depending on the solvent or solvents used, the temperature at which crystallization is carried out in step (5) is preferably in the range of from −20 to +90° C., more preferably from −10 to +70° C., more preferably from 0 to 50° C., more preferably from 10 to 40° C.

Optionally, seed crystals of the compound of formula (V) can be added.

According to a particularly preferred embodiment of the present invention, crystallization is performed in two or more steps, preferably in three or more steps. In an especially preferred first step, water is added, preferably to the combined filtrate and washing liquids as described above. The temperature at which this first step is carried out is preferably in the range of from 10 to 50° C., more preferably from 20 to 40° C. In an especially preferred second step, seeding crystals of the compound of formula (V) are added and the resulting mixture is stirred, preferably at a temperature in the range of from 10 to 50° C., more preferably from 20 to 40° C. In an especially preferred third step, water is added and the resulting mixture is stirred, preferably at a temperature in the range of from 10 to 50° C., more preferably from 20 to 40° C. In an especially preferred fourth step, the stirred mixture is cooled to a temperature below 20° C., preferably to a temperature in the range of from 0 to less than 20° C., more preferably from 10 to less than 20° C.

Step (6)—Separating the Crystallized Compound of Formula (V)

The crystallized compound thus obtained is optionally suitably separated from the solvent or solvent mixture in step (6) of the present invention. Suitable separation is preferably carried out by filtration. The separated crystallized compound of formula (V), preferably contained in the filter cake obtained from filtration, is preferably washed with a suitable solvent or solvent mixture. Suitable washing agents are, for example, mixtures of methanol, ethanol, n-propanol, iso-propanol, ethers, preferably THF, ketones, preferably acetone and acetonitrile with water. The temperature of the washing agents is preferably in the range of from 0 to 10° C., more preferably from 0 to 5° C.

The separated and preferably washed crystallized compound of formula (V) is preferably dried at suitable conditions. Drying of the crystallized compound of formula (V) is preferably carried out at a temperature of at most 50° C., preferably of at most 45° C. at a pressure of preferably at most 500 mbar, more preferably of at most 100 mbar, more preferably of at most 75 mbar, more preferably at most 50 mbar.

According to the present invention, it was found that generally, there is no need to further purify the thus obtained crystallized compound of formula (V) by tedious processes taught in the art, in particular by chromatography, and that said crystallized compound of formula (V) can be used without further purification, in particular as antifungal agent. Therefore, the present invention relates to above-defined process wherein the crystallized compound obtained from (5) or (6) is not subjected to a subsequent chromatography purification stage.

Thus, the present invention also relates to a composition which is especially preferably obtained or obtainable after step (5) or step (6) of the present invention, said composition comprising, preferably essentially consisting of a preferably crystalline chiral compound of formula (Va)

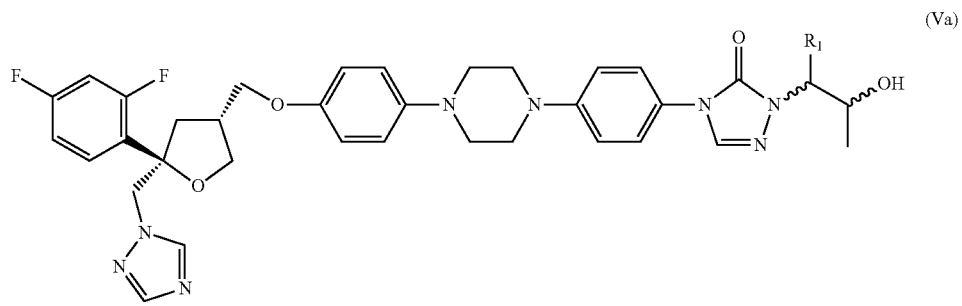

(Va)

or a salt thereof, wherein $R_1$ is an alkyl residue preferably having from 1 to 6 carbon atoms, more preferably from 1 to 4 carbon atoms, more preferably 1 or 2 carbon atoms, most preferably 2 carbon atoms, said composition preferably comprising a compound of formula (Vb)

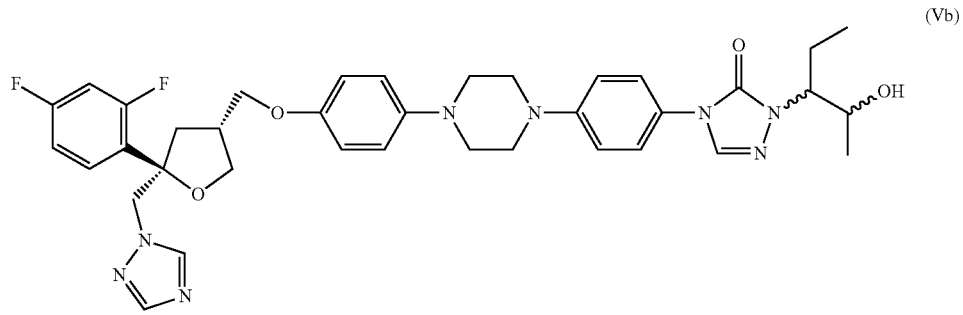 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vb)

wherein preferably at least 95%, more preferably at least 97%, more preferably at least 99% of the molecules of said preferably crystalline compound are present as isomer of formula (Vc)

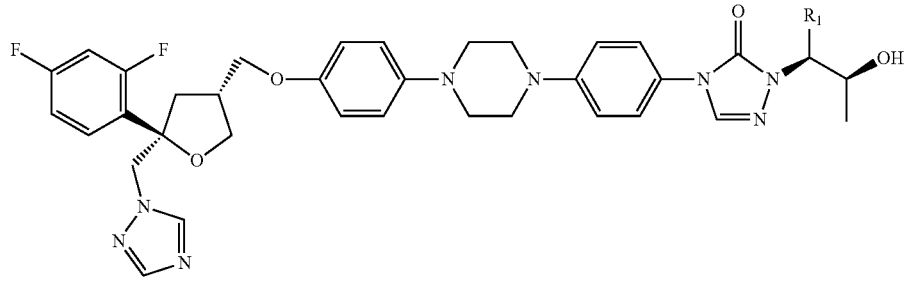

preferably as isomer of formula (Vd)

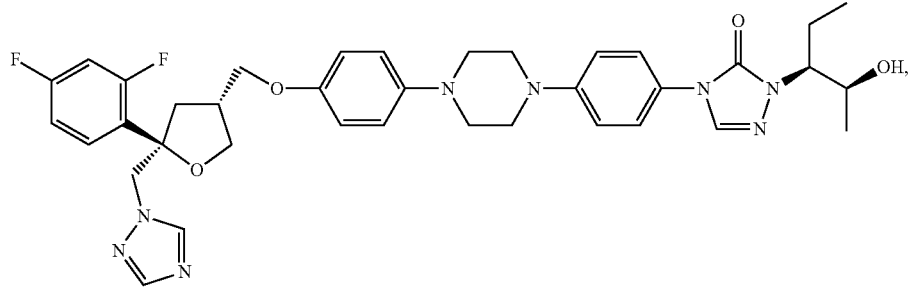

said composition containing at most 70 weight-ppm, preferably at most 50 weight-ppm, more preferably at most 30 weight-ppm, more preferably at most 10 weight-ppm, said composition in particular being free of a compound of formula (Ve)

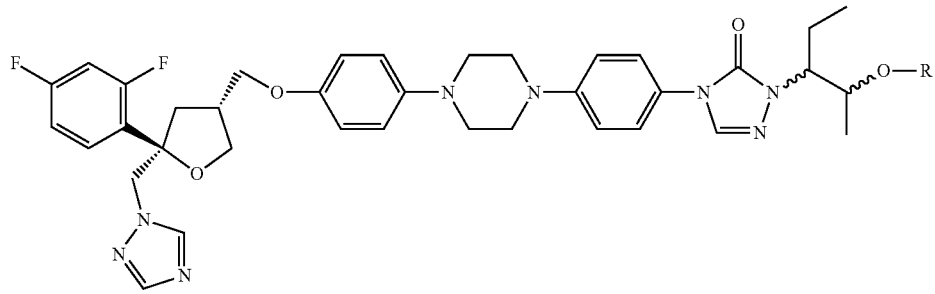

preferably of a compound of formula (Vf)

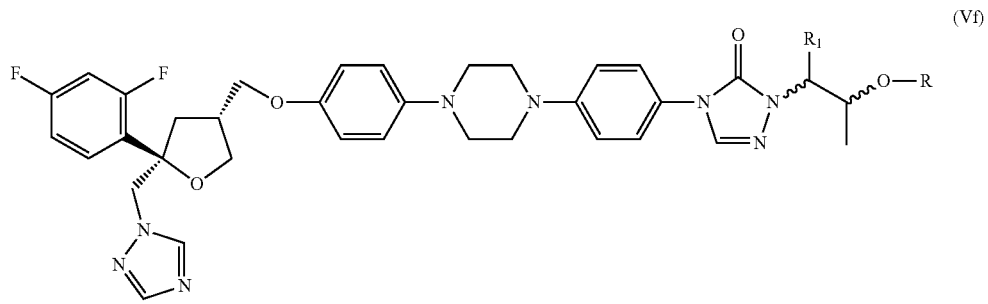

wherein —R is —CH$_2$—C$_6$H$_5$, —R preferably being selected from the group consisting of —SiR$_a$R$_b$R$_c$ and optionally substituted alkyl, aryl, alkaryl or aralkyl residues, where R$_a$, R$_b$ and R$_c$ are the same or different and selected from the group consisting of optionally suitably substituted alkyl and aryl residues, —R more preferably being a hydroxyl protecting group. The term "essentially consisting of" as used in this context of the present invention relates to such compositions of which at least 99.9 wt.-%, more preferably at least 99.99 wt.-% consist of the compound of formula (Va), relative to the total content with respect to the compounds of formula (Va) and (Vf).

Therefore, due to the novel advantageous process of the present invention, a composition as defined above can be provided which is free of benzyl-protected compound of formula (V). Especially preferably, a composition is provided which contains crystallized posaconazole which is free of benzyl-protected posaconazole.

According to above-defined process according to which posaconazole is prepared, usually a specific polymorphic form or a mixture of two or more polymorphic forms is obtained. If desired, this (crude) posaconazole can be re-crystallized at least once to give only one of these polymorphic forms or to give another polymorphic form or a mixture of two or more other polymorphic forms.

Preferably, according to the present invention, the crude posaconazole as described above is re-crystallized in a first step. Re-crystallization is especially preferably carried out from a mixture of acetone and water or from methanol as described in example 6 of U.S. Pat. No. 6,958,337.

A solvent-mediated solid phase transformation gives posaconazole of polymorphic form IV as described in WO 2010/000668. According to a preferred embodiment, the product obtained after re-crystallization as described above is stirred in a mixture of methanol and water in the preferred presence of seed crystals of posaconazole form IV to a temperature in the range of from 40 to 45° C. for a time in the range of from 4 to 48 hours. The obtained posaconazole of polymorphic form IV is suitably separated, preferably by filtration. The isolated product posaconazole of polymorphic form IV is preferably dried at suitable conditions. Drying is preferably carried out at a temperature of at most 45° C., preferably of at most 40° C. at a pressure of preferably at most 500 mbar, more preferably of at most 100 mbar, more preferably of at most 75 mbar, more preferably at most 50 mbar, more preferably in the range of from 30 to 40 mbar.

Therefore, the present invention also relates to the above-defined process, wherein the crystallized compound obtained from (5) or (6), in particular the compound of formula (Vb)

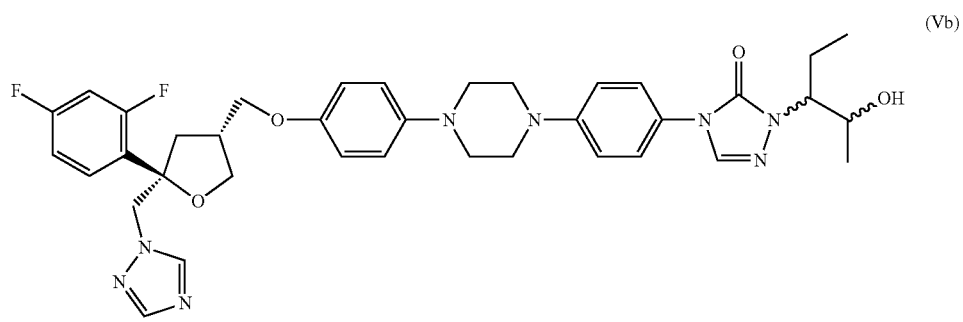 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

wherein preferably at least 95%, more preferably at least 97%, more preferably at least 99% of the molecules of said crystalline compound are present as isomer of formula (Vd)

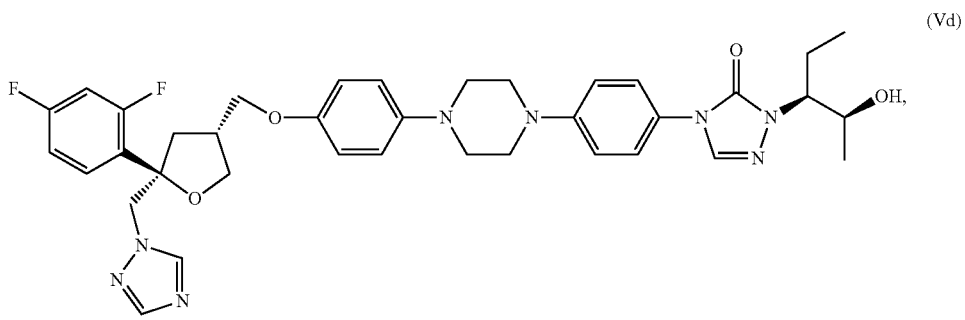

(Vd)

is re-crystallized, preferably from a mixture of acetone and water or from methanol, and is subsequently stirred in a mixture of water and methanol, preferably in the presence of seed crystals, said seed crystals comprising the crystalline compound of formula (Vd) in the form of polymorph IV.

The antifungal agent according to the present invention, or obtainable or obtained according to the process of the present invention may be suitably contained in a pharmaceutical composition, in particular for treating fungal infections. Such pharmaceutical compositions typically comprise an antifungally effective amount of the antifungal agent, preferably posaconazole, in particular posaconazole of polymorphic form IV. In particular, the pharmaceutical compositions according to the present invention contain the above-defined composition which is especially preferably obtained or obtainable after step (5) or step (6) of the present invention or after re-crystallization and/or solid phase transformation as herein described, said composition comprising, preferably essentially consisting of a preferably crystalline chiral compound of formula (Vb) and containing at most 70 weight-ppm, preferably at most 50 weight-ppm, more preferably at most 30 weight-ppm, more preferably at most 10 weight-ppm, said composition in particular being free of a compound of formula (Ve).

In addition to the antifungally effective amount of the antifungal agent, the pharmaceutical composition of the present invention preferably contains at least one pharmaceutically acceptable additive. Any pharmaceutically acceptable additive can be employed as long as it does not detrimentally affect the properties of the pharmaceutical composition. Examples of typical pharmaceutically acceptable additives are described, for example, in WO 2010/000668 A1, on page 13, lines 13 to 23, the respective disclosure being incorporated herein by reference. Other suitable pharmaceutically acceptable additives are described e.g. in Remington's Pharmaceutical Sciences, 15th Ed., Mack Publishing Co., New Jersey (1991).

The pharmaceutical compositions of the invention can be produced in a manner known per se to the skilled person as described, for example, in Remington's Pharmaceutical Sciences, 15th Ed., Mack Publishing Co., New Jersey (1991).

The pharmaceutical composition according to the present invention may be a solid or liquid. In this context, reference is made to WO 2010/000668 A1, page 13, lines 28 to 36, the respective disclosure being incorporated herein by reference. The pharmaceutically acceptable additive can also be an encapsulating material. In this context, reference is made to WO 2010/000668 A1, page 14, lines 1 to 6, the respective disclosure being incorporated herein by reference.

Formulations containing the antifungal agent of the present invention, preferably the composition of the present invention, may be topical formulations normally containing one or more non-toxic, pharmaceutically acceptable topical carriers, or other formulations such as those typically described for posaconazole. In this context, reference is made to WO 2010/000668 A1, page 14, lines 8 to 19, the respective disclosure and also the patent documents cited therein being incorporated herein by reference.

Therefore, the present invention relates to a pharmaceutical composition for treating fungal infections comprising an antifungally effective amount of a composition as defined above and a pharmaceutically acceptable carrier therefore.

In particular for these cases wherein the antifungal agent prepared according to the present invention is posaconazole, the agent, in particular the above-defined composition, can be used as a medicament to treat or prevent any of the disorders which can be treated or prevented by posaconazole. In particular, it can be used for treating or preventing fungal infections, especially in mammals, such as humans. Thus, a method of treating or preventing a fungal infection by administering a therapeutically effective amount of above-defined composition to a patient in need thereof is also contemplated, as well as the above-defined composition for use in a method of treating or preventing fungal infections in mammals in need of such treating or preventing such infections. The above-defined composition is suitable for treating or preventing a wide range of infections caused by fungal pathogens, including yeasts, dermatophytes and molds. Typical fungal infections which can be treated are disclosed in WO 2010/000668 A1, on page 11, line 29 to page 12, line 5, the respective disclosure being incorporated herein by reference.

Therefore, the present invention relates to the use of above-defined composition for use as a medicament. Further, the present invention relates to the use of above-defined composition for the preparation of a medicament for treating or preventing fungal infections in mammals in need of such treating or preventing such infections.

As indicated hereinabove, the present invention is, among others, characterized in that for the preparation of the compound of formula (IV), preferably the compound of formula (V), more preferably posaconazole, even more preferably posaconazole contained in above-defined composition which is essentially free of the compound of formula (Ve), the compound of formula (IIc) is employed. The advantages of the use of this specific compound are explained throughout the present invention hereinabove. Therefore, the present invention also relates to the use of a compound of formula (IIc)

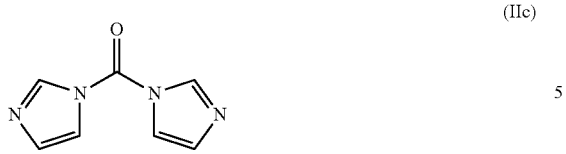
(IIc)

for the preparation of an antifungal agent, preferably for the preparation of a preferably crystalline chiral compound of formula (Vb)

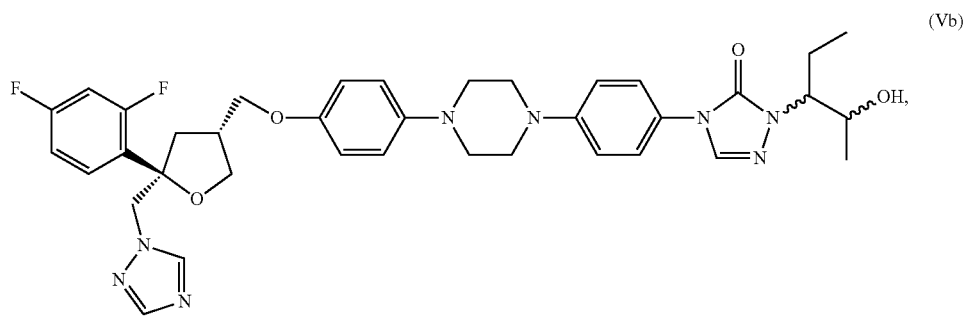 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vb)

most preferably for the preparation of a preferably crystalline compound of formula (Vd)

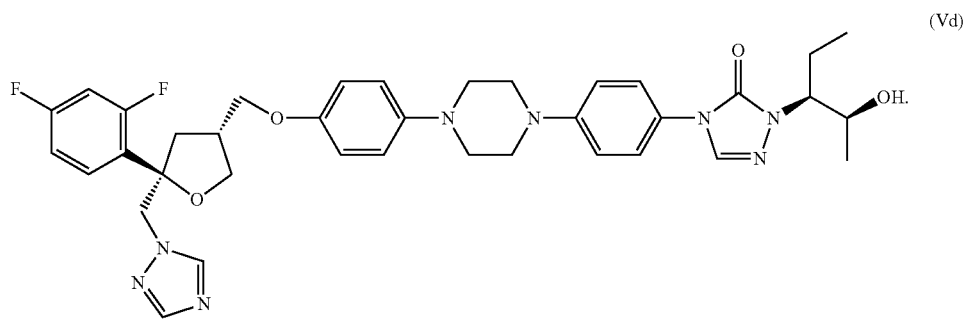 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vd)

Also, the present invention relates to a method for the preparation of an antifungal agent, preferably for the preparation of a preferably crystalline chiral compound of formula (Vb), most preferably for the preparation of a preferably crystalline compound of formula (Vd), wherein a compound of formula (IIc) is employed.

Generally, the present invention also relates to a chiral compound which is obtainable or which is obtained according to a process of the present invention comprising steps (1.1) to (2), or comprising steps (1.1) to (3), or comprising steps (1.1) to (4), or comprising steps (1.1) to (5), or comprising steps (1.1) to (6), preferably comprising steps (1.1) to (2) or comprising steps (1.1) to (5) or (1.1) to (6).

The present invention is illustrated by the following examples.

EXAMPLES

Example 1

Synthesis of the Compound of Formula (B)

Ex1.a

Preparation of the compound of formula (BB) with L=Cl

(BB)

In 20 ml of MTBE, 3.8 g of Mg were suspended. The temperature of the suspension was 55° C. Then, 0.5 g of Grignard reagent (CH$_3$)$_3$Si—CH$_2$MgCl in MTBE from a previous batch were added in order to dry the system (if no such Grignard reagent is available for the first batch, (CH$_3$)$_3$Si—CH$_2$MgCl in diethyl ether (CAS Registry Number: 13170-43-9) commercially available as 1.0 M solution from Sigma-Aldrich, can be used), followed by 1.0 ml of chloromethyl trimethylsilane (CM-TMS; CAS Registry Number: 2344-80-1; commercially available from Sigma-Aldrich). Then, a solution of 14 ml of the CM-TMS in 43 ml of MTBE was added slowly over a period of 2 hours at a temperature of 55° C. The mixture was stirred for 2 hours at 55° C. and then cooled to a temperature of −10° C. Subsequently, 10.0 g of the commercial compound of formula (AA) with L=Cl (CAS Registry Number: 51336-94-8; commercially available from Sigma-Aldrich) in 30 ml of MTBE were added and the temperature was kept in the range of from 0 to −10° C. The reaction mixture was quenched in a 20% (w/v) aqueous solution of ammonium chloride. The obtained organic layer was washed with a 20% (w/v) aqueous solution of ammonium chloride. The thus washed organic layer was then washed with water.

To the organic layer, 11.0 ml of concentrated sulphuric acid were added, and the temperature was kept at 25 to 30° C. Then, the reaction mixture was stirred at a temperature of from 45 to 50° C. for 3 hours. Subsequently, the reaction mixture was cooled to 20° C. and 25 ml of water were added, and the organic layer was separated. The obtained organic layer was extracted with a 9% (w/v) aqueous solution of sodium bicarbonate, followed by washing with water. The solvents of the washed organic layer were removed by distillation under reduced pressure, and the title compound was obtained as an oil. The yield was 9.4 g, corresponding to a theoretical value of 95%.

Ex1.b

Preparation of the compound of formula (CC) with $R_{11}=R_{22}=CH_2CH_3$

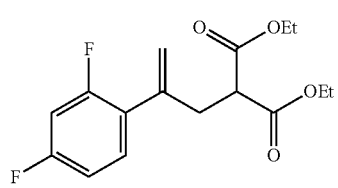

(CC)

10.0 g of the compound of formula (BB) as oil, as obtained according to (Ex1.a) were dissolved in 20 ml of DMSO under stirring. Then, 3.2 g of NaOH flakes and 24.0 ml of diethyl malonate were added. The resulting suspension was stirred for 5 hours at 25 to 30° C. Subsequently, 100 ml of water were added, and the resulting mixture was stirred for 30 min. The thus obtained solution was extracted with 80 ml of cyclohexane at 25 to 30° C. After separation of the layers the aqueous layer was extracted with 40 ml of cyclohexane at 25 to 30° C. The combined organic layers were washed with a 5% (w/v) aqueous solution of NaOH, followed by washing with water. After washing, the solvents of the organic layer were removed by distillation under reduced pressure and the title compound was obtained as an oil. The yield was 15.0 g, corresponding to a theoretical value of 90.0%.

Ex1.c

Preparation of the compound of formula (DD)

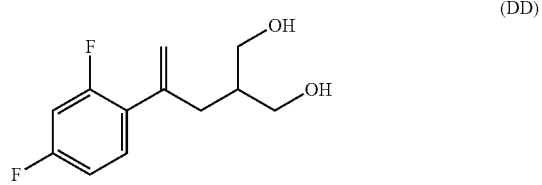 [SMILES: C=C(CC(CO)CO)c1ccc(F)cc1F]

(DD)

10.0 g of the compound of formula (CC) as oil, as obtained according to (Ex1.b), were dissolved in 120 ml of isopropyl alcohol and 13.0 ml of water under stirring at 25 to 30° C. The resulting mixture was cooled to a temperature of from 0 to −5° C. Then, 2.3 g of lithium chloride and 2.1 g of sodium borohydride were added at 0 to −5° C. The resulting suspension was stirred at 25 to 30° C. for 20 hours. The pH of the stirred mixture was adjusted to a value of 1 (measured by using a calibrated pH meter) by addition of 4 N aqueous HCl. Afterwards, a 20% (w/v) aqueous solution of NaOH was added to adjust the pH to a value of 10 (measured by using a calibrated pH meter). The resulting mixture was stirred for 1 hour. Then, the lower aqueous layer was drained. From the separated organic layer, the isopropyl alcohol was distilled off, and an oil was obtained. To the oil, 100 ml of toluene and 100 ml of water were added, and the product was extracted into the toluene layer. The solvents of the resulting toluene layer were removed by distillation, under reduced pressure and the title compound was obtained as oil. The yield was 6.0 g, corresponding to a theoretical value of 82.0%.

Ex1.d

Preparation of the compound of formula (EE)

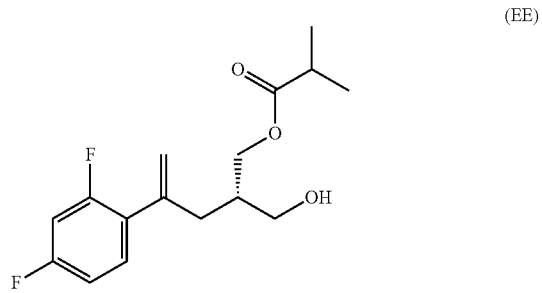 [SMILES: C=C(C[C@@H](CO)COC(=O)C(C)C)c1ccc(F)cc1F]

(EE)

10.0 g of the compound of formula (DD) as oil, as obtained according to (Ex1.c), were dissolved in 80 ml of toluene and cooled to −15° C. Then, 7.4 g of sodium bicarbonate, 0.5 g of enzyme (Novo SP 435; Candida antaretica, Novozym 435 from Novo Nordisk), and 7.9 ml of isobutyric anhydride were added. The resulting mixture was stirred at −15° C. for 24 hours. Then the solids were filtered off and the filtrate was washed with a 5% (w/v) aqueous solution of sodium bicarbonate, followed by washing with water. The solvents of the resulting organic layer were removed by distillation under reduced pressure to obtain the desired product as an oil. This oil was dissolved in 40 ml of n-heptane at 50 to 60° C. The clear solution was gradually cooled to a temperature of 10° C.

The compound of formula (EE) crystallized as colorless crystals. The obtained solids were filtered, and the wet filter cake was washed with 20 ml of n-heptane. The filter cake was then dried at 40° C. in vacuo and the title compound was obtained as colorless crystals. The yield was 9.2 g, corresponding to a theoretical value of 70.0%.

Ex1.e

Preparation of the compound of formula (FF) with Hal=I

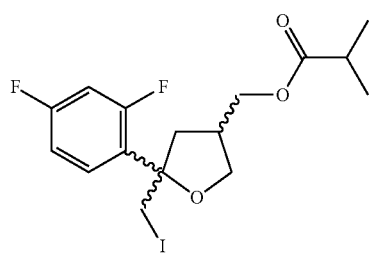

(FF)

10.0 g of the crystals obtained in (Ex1.d) were dissolved in 80 ml of ethyl acetate under stirring. The resulting solution was cooled to −15° C., and 21.5 g of iodine and 7.0 g of sodium bicarbonate were added. The obtained suspension was stirred at −15° C. for 5 hours. The reaction mixture was quenched in 200 ml of a 10% (w/v) aqueous solution of sodium sulphite. The organic layer was washed with 100 ml of a 10% (w/v) aqueous solution of sodium sulphite, followed by washing with water. The solvents of the thus obtained, washed organic layer were removed by distillation under reduced pressure to obtain the title compound as an oil. The yield was 13.5 g, corresponding to a theoretical value of 95.0%.

Ex1.f

Preparation of the compound of formula (GG)

10.0 g of the compound of formula (FF) as oil, as obtained according to (Ex1.e), were dissolved in 80 ml of DMSO under stirring. Then, 10 g of the sodium salt of 1,2,4-triazole were added at 25 to 30° C., and the resulting reaction mixture was stirred for 24 hours at 85 to 90° C. The mixture was then cooled to 25 to 30° C., and 25 ml of 5% (w/v) aqueous solution of sodium hydroxide were added. The mixture was then stirred for 3 hours at 25 to 30° C. 100 ml of water were added, and the product was extracted into 150 ml of methyl tetrahydrofuran. The thus obtained organic layer was washed with a 10% (w/v) aqueous solution of sodium chloride, and subsequently the solvents of the resulting separated organic layer were removed by distillation under reduced pressure to obtain the title compound of formula (GG)

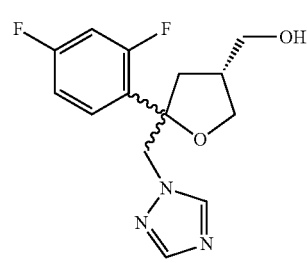

(GG)

as a crude oil. The yield was 6.0 g, corresponding to a theoretical value of 86.0%.

Ex1.g

Preparation of the HCl salt of compound (GG)

10.0 g of the compound of formula (GG) as crude oil as obtained in (Ex1.f) were dissolved in 200 ml of acetone under stirring at 30 to 40° C. The resulting solution was cooled to 25 to 30° C. Then, HCl in MTBE (10 wt.-%) was added over a period of 15 min at 25 to 30° C. The solid crystallized when the mixture was stirred for 15 min. Then, 200 ml of MTBE were added slowly over a period of 30 min. The suspension was cooled to 0 to −5° C. and stirred for 2 hours. The product was filtered, and the wet cake was washed with 20 ml of MTBE. After drying at 70° C. in vacuo, the HCl salt of the compound (GG) was obtained as colourless solid. The yield was 9.5 g, corresponding to a theoretical value of 85.0%.

The HCl salt of compound of formula (GG) was obtained as mixture of the cis-isomer with the respective trans-isomer with a cis:trans ratio of 9:1.

Ex1.h

Preparation of an HCl salt of the compound of formula (GG) with solid extraction, using MIRK and n-butanol as solvent mixture 20.0 g of the crystalline HCl salt of the compound of formula (GG) containing the HCl salt of the cis-isomer of formula (GGa)

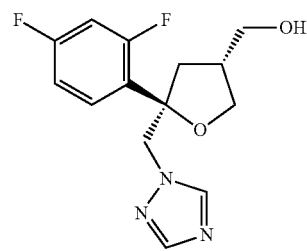

(GGa)

and the HCl salt of the trans-isomer of formula (GGb)

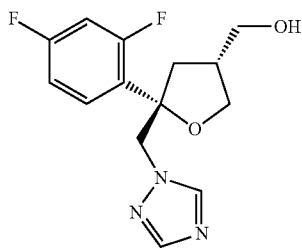

(GGb)

with a cis:trans ratio of 9:1 (60 mmol) obtained as described above in (Ex1.g) were suspended in a mixture of n-butanol (50 ml) and MIBK (50 ml). The mixture was heated to 60° C., and this temperature was maintained for a period of 2 hours. Subsequently, the mixture was cooled to room temperature. The obtained solid was filtered off and washed with a small amount of diethyl ether.

This solid (14.55 g, 43.9 mmol) was re-suspended in a mixture of n-butanol (36.4 ml) and MIBK (36.4 ml). The mixture was heated to 60° C., and this temperature was maintained for a period of 2 hours. Subsequently, the mixture was cooled to room temperature. The obtained solid was filtered off and washed with a small amount of diethyl ether.

After drying under vacuum at 45° C., the HCl salt of compound of formula (GG) was obtained as colorless crystalline solid with an overall yield of 66% over 2 steps, corresponding to 10.75 g. The crystals showed bifringing under the microscope.

The HCl salt of compound of formula (GG) contained the HCl salt of the cis-isomer and the HCl salt of the trans-isomer with a cis:trans ratio of 99.2:0.8, as determined by HPLC.

HPLC Method for Determination of Purity and Cis/Trans Ratio:

| Principle | Determination by HPLC using UV detector | |
|---|---|---|
| Reagents and Equipment | Potassium dihydrogen phosphate | Merck Cat. No. 60487305001730 |
| | Orthophosphoric acid (85 %) | AR Grade e.g (Merck, Cat No 61768205001046) |
| | Acetonitrile | HPLC grade (e.g. Merck Cat. No. 61830025001046) |
| | HPLC system | Agilent 1100 series or similar |
| | pH meter | e.g. Metrohm or equivalent |
| Buffer Preparation | Dissolve 2.72 g of Potassium dihydrogen phosphate in 1000 ml of water and adjust the pH to 3.0 ± 0.05 by adding dilute orthophosphoric acid (85%) using a pH meter. Filter through 0.45 μm (micrometer) filter and degas. | |
| Diluent | Buffer: Methanol (80:20) v/v | |
| Chromatographic Conditions | | |
| Column | $C_{16}$, 250 mm X 4.6 mm i.d.5 μ, e.g. Ascentis RP amide or equivalent column can be used after appropriate validation. | |
| System. | Gradient | |
| Column Temperature | 40° C. | |
| Mobile phase A | Buffer | |
| Mobile phase B | Buffer: Acetonitrile (30:70) v/v | |
| Flow rate | 2.0 ml/min | |
| Injection temperature | 25° C. | |
| Injection volume | 25 μl (microliter) | |
| Run time | 45 minutes | |
| Detection wavelength | 210 nm | |
| System | Gradient | |

| Gradient program | Time | % mobile phase B |
|---|---|---|
| | 0 | 20 |
| | 5 | 20 |
| | 15 | 40 |
| | 25 | 80 |
| | 28 | 90 |
| | 39 | 90 |
| | 41 | 20 |
| | 45 | 20 |

The X-ray powder diffraction pattern (XRD) of this compound of formula (GG) is shown in FIG. 3.

Method for the Recording of X-Ray Diffractograms:

The samples were analyzed on the Zero background holder in spinning mode at ambient conditions. A typical precision of the 2-Theta values is in the range of about ±0.2° 2-Theta. Thus a diffraction peak that appears at 8.6° 2-Theta can appear between 8.4 and 8.8° 2-Theta on most X-ray diffractometers under standard conditions.

Instrument Parameters:

XRD Measurement Conditions:

| Instrument | X'PERT PRO PANalytical |
|---|---|
| Scan Axis | Gonio |
| Start Position [°2 Th.] | 3.0 |
| End Position [°2 Th.] | 40.0 |
| Step Size [°] | 0.0170 |
| Scan Step Time [s] | 100 |
| Scan Type | Continuous |
| Anode Material | Cu |
| Generator Settings | 45 kV, 40 mA |
| Spinning | Yes |

Incident Beam Optics:

| Soller Slits | 0.02 radians |
|---|---|
| Divergence Slit Type | Programmable Slits (Fixed 0.5°) |
| AntiScatter Slits | Fixed Slits (1°) |
| Beam Mask | 10 mm (MPD/MRD) |

Diffracted Beam Optics:

| Antiscatter Slit | Programmable Slits (Fixed 0.5°) |
|---|---|
| Soller Slits | 0.02 radians |
| Filter | Nickel |
| Detector | X'celerator |
| Mode | Scanning |
| Active Path Length | 2.122° |

Ex1.j

Synthesis of the compound of formula (B)

A suspension of 292.0 g of the compound of formula (GG) obtained according to (Ex1.h) above (MW: 331.75 g/mol; 0.88 mol, d. r.>99:1; 1.0 equiv.) in 2.92 L of $CH_2Cl_2$ was prepared at a mass temperature of 12±3° C. To this, 142.5 g of $Et_3N$ (MW: 101.19 g/mol, 195.9 mL, 1.41 mol, 1.6 equiv.) were added slowly at 22±8° C. within 60 min. The mixture was cooled to a mass temperature of 12±3° C. and 129.5 g of DMAP (4-dimethylamino-pyridine; MW: 122.17 g/mol; 1.06 mol, 1.2 equiv.) were added in one portion. Subsequently, 185.0 g of TsCl (tosyl chloride; MW: 190.65 g/mol; 0.97 mol; 1.1 equiv.) were added in at least five portions at a mass temperature of 22±8° C. within 60 min. By the last addition, the mass temperature was adjusted to 25±3° C. and stirring of the pink suspension was continued for further 3 h at 25±3° C. The reaction mixture was extracted with 1.46 L of aq. 10% HCl at 25±3° C. followed by 1.46 L of aq. 9% NaHCO₃ at 25±3° C. followed by 1.46 L of H₂O. The organic layer was concentrated to approx. 20% of its original volume at 25±3° C. under reduced pressure. To the concentrate, 5.83 L of heptane (25±3° C.) were added slowly at 25±3° C. within 60 min. The resulting suspension was cooled to 2±3° C. and stirring was continued for 60 min. The solid was filtered off and washed with 2×1.46 L of heptane (25±3° C.). The product was dried under reduced pressure<50 mbar) at 40° C. over night until a level of ≤0.1% of DCM was achieved.

372.8 g of the compound of formula (B) (0.83 mol, 94% yield "as is") were obtained.

The product contained the compound of formula (B), the cis-isomer

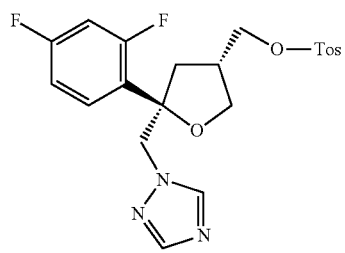

(B)

and the trans-isomer

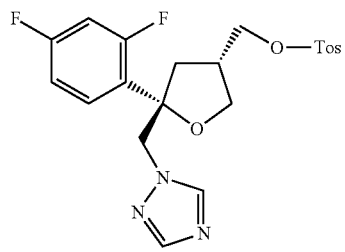

with a cis:trans ratio of 99.2:0.8.

Example 2

Synthesis of the Compound of Formula (Ia)

A solution of 297 mg of BHT (butylated hydroxytoluene; M=220.35 g/mol; 1.35 mmol; 500 ppm) and 727 g of the compound of formula (A)

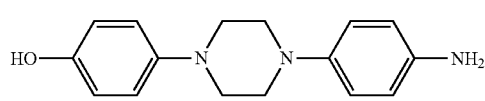

(A)

(MW: 269.35 g/mol; 2.698 mol; 1.0 equiv.; obtainable, for example, according to example 1 of EP 1 230 231 131 (on page 4)) in 4.7 L of DMSO was prepared at a mass temperature of 30±2° C. To this was added a solution (30±2° C.) of 161.9 g of NaOH (MW: 40.0 g/mol, 4.047 mol, 1.5 equiv.) in 161.9 g of oxygen-free H₂O upon keeping the mass temperature at ≤32° C. The mixture was stirred for 10 min at 30±2° C. Then, a solution (30±2° C.) of 1335 g of the compound of formula (B) contained in the product as obtained according to Example 1 (Ex1.j) above

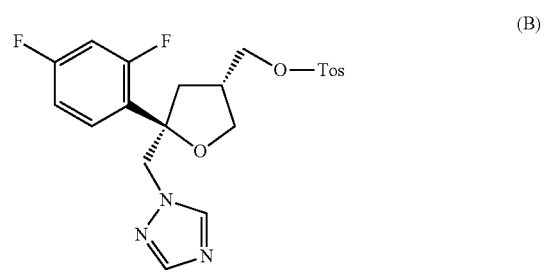

(B)

(12.968 mol=1.1 equiv., MW=449.48 g/mol) in 6.6 L of DMSO was added at a mass temperature of ≤32° C. within 10 min. The pH of the reaction mixture was checked after a reaction time of 60 min and at least also after 5 and 8 hours. After stirring for 60 to 90 min at 30±2° C. the crystallization of the product started. The dark brownish, thin suspension was stirred for 10-15 h at 30±2° C. At minimum agitation rate, the addition of 21.8 L of H₂O was started at 30±2° C. and was carried out at a constant rate whereby the reaction temperature was allowed to rise simultaneously to 45±5° C. Then, the remaining water was added at a rate to keep the temperature at 45±5° C. (overall addition time: about 60 min in total). Subsequently, the suspension was cooled to 20±2° C. in 60 min and stirred for further 60 min at 20±2° C. The resulting solid was filtered off and washed with 8.5 L of cold 1% oxygen-free aqueous NaOH (5-10° C.), then 2×8.5 L of cold oxygen-free H₂O (15-10° C.) followed by 2×8.5 L of isopropanol (22±3° C.).

All operations being part of the following purification procedure were carried out under a positive nitrogen atmosphere.

The wet crude product (approx. 2.44 kg) in 72.7 L of acetonitrile was heated to reflux temperature. The mixture was refluxed for 10-15 minutes. To the resulting solution 116 g of charcoal (Ceca Eno) were added and the suspension was stirred for 10 min at reflux temperature. The charcoal was filtered off and the filter cake was washed with 11.6 L of hot acetonitrile. Under stirring the yellow coloured filtrate was cooled to 20±2° C. during 1 hour. Crystallization started at approx. 60° C. Under stirring the crystal suspension was cooled to 0±2° C. over 30 min and stirred at this temperature for one hour. The resulting crystals were filtered off and washed with 6 L of cold acetonitrile (≤5° C.).

The product was dried at ≤75° C. (preferred temperature 70±5° C.) under reduced pressure≤55 mbar) until a level of ≤1.4% of residual water was achieved. 1180 g of the compound of formula (Ia.)

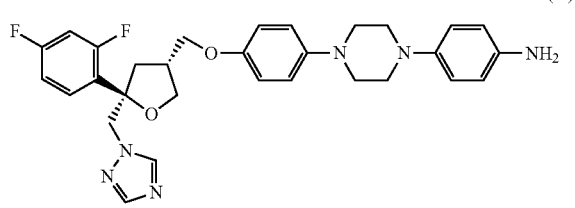

(Ia)

(MW: 546.63 g/mol; 2.18 mol, 80.0% yield "as is") were obtained as a white to yellow crystalline powder.

Example 3

Synthesis of the compound of formula (IIIa)

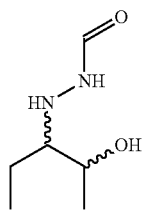

(IIIa)

Example 3.1

Synthesis of the compound of formula (II) with Y=phenyl a) 1.70 kg of nitrosobenzene (MW: 107.11; 15.9 mol; 1.0 eq.) were dissolved in 6.16 L of DCM by stirring at 20-25° C. under $N_2$ atmosphere.

b) In a separate vessel, 2.76 kg propionaldehyde (MW: 58.08; density: 0.798 g/mL; 47.5 mol; 3.0 eq.) and 5.28 L of DCM were cooled to −6 to −4° C. under $N_2$ atmosphere. To the resulting mixture, 0.057 kg of glacial acetic acid (MW: 60.05; density: 1.049 g/mL; 0.95 mol; 0.06 eq.) and 0.55 kg of D-proline (MW: 115.13; 4.75 mol; 0.3 eq.) were added, and a fine suspension was obtained.

c) To this suspension of b), 0.4 L of the nitrosobenzene solution obtained in a) were added. Onset of the reaction was indicated by discoloration of the suspension and a temperature rise up to +3° C. within 1 min. Then, the remaining nitrosobenzene solution (about 7 L) of the nitrosobenzene solution obtained in a) were added at a rate to keep the reaction temperature between −5 and −3° C. The mixture gradually turned darker and resulted in a clear solution when addition was complete. Stirring was then continued for 10 min, and complete conversion was determined using HPLC. The compound of formula (I) with Y=phenyl was obtained as intermediate with an enantiomeric purity expressed as enantiomeric excess (ee)>98%, i.e. more than 99% of the molecules of the chiral compound of formula (i) with Y=phenyl were present as isomer of formula (Ia) with Y=phenyl. Enantiomeric purity was determined analogously to the method described in Brown et al., *J. Chem. Soc.* 2003, 125 (36), 10808-10809 and using Chiralcel OD-H and n-heptane/isopropanol/diethylamine as eluent.

d) Subsequently, 8.8 L of DCM, 3.0 kg of a molecular sieve having pores with a diameter of 0.4 nm (4 Angstrom; commercially available from Aldrich), and 3.14 kg of formyl hydrazine (MW: 60.06; 52 mol; 3.3 eq.) were added at 0-5° C., leading to an increase in temperature. Stirring was continued at 0-5° C. under $N_2$ atmosphere. After 3 hours, complete conversion was determined using HPLC.

e) The obtained solids were filtered and washed with 4.4 L of DCM. The solution was concentrated to ¼ of its original volume at a bath temperature of <10° C. Then, 28 L of MTBE were added, and the resulting solution was reduced to ¼ of its original volume by distillation at a bath temperature of <10° C. The resulting organic layer was then diluted with 7 L of MTBE and extracted five times with 28 L of a 20% aqueous sodium chloride solution. Then, 8.8 L of DCM were added for azeotropic removal of water. The resulting solution was concentrated to give 12 kg of a solution of the compound of formula (ii) with Y=phenyl in MTBE which contained 2.86 kg of said compound (MW 207.23; 80% yield), f) This solution containing the compound of formula (II) with Y=phenyl was used in the next step (Example 3.2) without further purification.

Example 3.2

Synthesis of the compounds of formula (iii) and (iv) with Y=phenyl, and $R_{aa}$, $R_{bb}$ and $R_{cc}$=methyl and $R_1$=ethyl a) 0.887 kg of the compound of formula (II) as obtained according to Example 3.1 (MW: 207.23; 4.28 mol; 1.0 eq.), employed as a solution in MTBE (total weight 290 g) which contained about 2 wt.-% of $H_2O$, were dried with 1.54 kg of a molecular sieve having pores with a pore diameter of 0.4 nm (4 Angstrom; commercially available from Aldrich) at 20-25° C. for 30 min. Thus, the water content was reduced to a value of less than 0.1 wt.-%. Then, the molecular sieve was removed by filtration and washed with 1.7 L of MTBE. The resulting solution was diluted with 16 L of MTBE. The water content of this solution was about 0.05% (0.5 mol; 0.12 eq.).

b) Then, 2.8 L of BSA (bistrimethylsilylacetamide) (MW: 203.43; density: 0.832 g/mL; 11.5 mol; 2.7 eq.) were added to the filtrate. The resulting solution was stirred at 20-25° C. After 1 hour, silylation was complete, as detected by $^1$H-NMR. The compound of formula (iii) with Y=phenyl and $R_{aa}$, $R_{bb}$ and $R_{cc}$=methyl was obtained as intermediate.

c) Then, the solution was cooled to −70 to −60° C., and 8.65 L of a solution of ethyl magnesium chloride in THF (2 mol/l; MW: 88.82; density: 0.978 g/ml; 17.3 mol; 4.0 eq.) were added at a rate to keep the reaction temperature between −70 and −60° C. This mixture was stirred for 1 hour at −60° C. Subsequently, the temperature was raised to −25° C., and stirring was continued. After 3 hours, complete conversion was detected by HPLC. The reaction was then quenched by dropwise addition of 5.5 kg of MeOH at a temperature of −25° C. During quenching, the mixture was allowed to warm up to 0-15° C.

d) The resulting organic layer was then extracted at 20-25° C. twice with 30 L of a 10% aqueous ammonium chloride solution and once with 30 L of a 20% aqueous sodium chloride solution. The organic layer (20 kg) contained approximately 0.89 kg of the compound of formula (Iv) with Y=phenyl and $R_1$=ethyl (MW: 237.30; 80% yield) and was used for the next step (Example 3.3) without further purification.

Example 3.3

Synthesis of the compounds of formula (III) with R=H and $R_1$=ethyl, i.e. the compound of formula (IIIa)

a) 0.89 kg of the compound of formula (iv) (MW: 237.30; 3.76 mol; 1.0 eq.), obtained according to Example 3.2 and used as a solution in MTBE (total weight 20 kg) was diluted with 1 L of MeOH at 20-25° C.

b) Then, 0.9 kg of palladium on carbon (Pd/C; 5% Pd; 50% water) were added, and the resulting solution was stirred vigorously at 20-25° C. Reduction reaction was carried out with 1 atm of $H_2$. The vessel was evacuated and vented with 1 atm $H_2$ three times. After 1.5 hours of stirring under $H_2$ atmosphere, complete conversion was detected by HPLC. Then, the suspension was filtrated and the catalyst washed with 1.8 L of MTBE/MeOH (1/1 v/v). The combined filtrates were concentrated to a yellow oil to yield the crude compound of formula (IIIa), containing about 40% (about 0.55 kg) of the compound of formula (IIIa).

c) This oil was diluted with 13.9 L of MTBE at 20-25° C., and the resulting solution was seeded. After 1 hour of stirring at 20-25° C., a fine suspension was obtained. Then, 17 L of CHX (cyclohexane) were added, the mixture was cooled to 0° C. and stirred at 0° C. for 3 hours, resulting in a thick suspension of the compound of formula (IIIa). The thus obtained crystals were collected and washed with 2.2 L of a cold (0° C.) mixture of MTBE and CHX (1/1 v/v) to give 0.44 kg of the compound of formula (IIIa) after drying (MW 146.19; 80% yield; 64% yield with respect to the compound of formula (ii)). More than 99% of the molecules of the chiral compound of formula (IIIa) were obtained as isomer according to formula (IIIb).

10.4 g of this yellow colored material were added to 50 mL of isopropyl acetate, and the resulting mixture was heated to a temperature of 85 to 89° C. until a solution was obtained. 0.5 g of activated carbon were added to the yellow solution, and after stirring for several minutes, the hot mixture was filtered and allowed to cool to about 5° C. under stirring. After stirring for 2 to 3 hours, the precipitated product was filtered, washed with 5 mL of isopropyl acetate and dried at room temperature under vacuum over night to give 8.54 g of the product as a off-white solid (melting point 78 to 80° C.), i.e. the compound of formula (Ma), wherein more than 99% of the molecules of said compound were obtained as isomer according to formula (IIIb).

Preparation of seeds used in this step c):

100 g of the crude oil obtained in step b) above were purified by column chromatography using 800 g silica gel 60 (0.063-0.200 mm, Merck) as stationary phase and DCM/methanol=20/1 as mobile phase. The fractions containing the desired product in pure form, as determined by TLC (Merck, silica gel 60 $F_{254}$, mobile phase CHX/ethyl acetate 1/1), were collected. After evaporation of the solvents the obtained solid was recrystallized from diethyl ether. The resulting crystals were collected and used as seeds after drying (20° C., <100 mbar).

d) The IR spectrum and the X-ray diffractogram are shown in FIGS. 1 and 2.

Experimental data were obtained as follows:

The enantiomeric purity of the compound of formula (IIIa) as obtained in c) was measured by HPLC as follows:

Chromatography

HPLC apparatus: Agilent 1200
Column: Waters)(Bridge C18, 2.5 μm, 50×4.6 mm (order no. 186003090)
System: gradient
Eluent A: buffer solution pH 7.0
Eluent B; buffer solution pH 7.0/acetonitrile=2/8 (v/v)
Flow rate: 1.8 mL/min
Oven temperature: 40° C.
Injection volume: 10 μL (microliter)
Stop time: 20 min
Detection: λ (lambda) 260 nm
Gradient:

| t (min) | 0 | 8 | 12 | 14 | 15 | 20 |
|---|---|---|---|---|---|---|
| % B | 10 | 20 | 100 | 100 | 10 | 10 |

Buffer solution pH 7.0 prepared according to the following recipe: dissolve 7.0 mL of triethylamine in 900 mL of water, adjust the pH to 7.0 with $H_3PO_4$ and dilute to 1000 mL with water.

Reagent solution prepared according to the following recipe: dissolve 80 to 90 mg of (S)-(−)-α-methylbenzyl isocyanate in acetonitrile and dilute to 1.0 mL with acetonitrile.

Sample Preparation:

a) Test Stock Solution Prepared According to the Following Recipe:

Dissolve 38 to 42 mg of the substance to be tested, weighed accurately to 0.01 mg, in 1.0 mL of acetonitrile.

b) Test Solution Prepared According to the Following Recipe:

In an HPLC vial, mix 100 μL (microliter) of test stock solution and 100 μL (microliter) of reagent solution. Keep at room temperature (20 to 25° C.) for 30 min, add 800 μL (microliter) of buffer solution pH 7.0 and shake well. Then cool the solution on an ice bath (0° C.) for additional 30 min (precipitation of reagent) and filtrate a sample through 0.2 μm (micrometer) directly into another HPLC vial.

Infrared spectra (IR) data were collected on a MKII Golden Gate™ Single Reflection Diamond ATR (attenuated total reflection) cell with a Bruker Tensor 27 FTIR spectrometer with 4 $cm^{-1}$ resolution at ambient conditions. To collect a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus, an infrared peak that appears at 1716 cm$^{-1}$ can appear between 1714 and 1718 cm$^{-1}$ on most infrared spectrometers under standard conditions.

X-ray data (powder diffraction pattern XRPD, X-ray diffraction pattern XRD, X-ray diffractogram) were collected on a Unisantis XMD 300 X-ray powder diffractometer with a position sensitive detector in parallel beam optics using the following acquisition conditions: tube anode: Cu, 40 kV, 0.8 mA; 3-43° theta/2theta; simultaneous detection of regions of 10 per step with detector resolution 1024, counting time 300 seconds per step. Samples were measured at room temperature in a standard sample holder on a rotating sample spinner. A typical precision of the 2-theta values is in the range of ±about 0.2° 2-Theta. Thus a diffraction peak that appears at 5.0° 2-Theta can appear between 4.8 and 5.2° 2-Theta on most X-ray diffractometers under standard conditions.

HPLC for determination of completion of conversion as mentioned in Example 3.1, c) and d), Example 3.2), c) and Example 3.3, b) was performed as follows:
Column: Zorbax Eclipse XDB-C18, 150*4.6 mm, 5 µm (micrometer).
System: gradient
Buffer: 2.10 g KH$_2$PO$_4$+4.28 g K$_2$HPO$_4$/2.0 L H$_2$O, adjust with 85% H$_3$PO$_4$ to pH 6.5
Mobile phase A: 20 mM phosphate buffer pH 6.5/acetonitrile, 85/15, v/v
Mobile phase B: 20 mM phosphate buffer pH 6.5/acetonitrile, 50/50, v/v
Solvent: H$_2$O/acetonitrile=50/50 v/v
Flow rate: 1.5 mL/min
Oven temperature: 60° C.
Injection volume: 5-20 µL (microliter)
Stop time: 30 min
Detection: λ (lambda)=210 nm (Agilent 1200 detector)
Autosampler: 5° C.
Gradient:

| t [min] | | | | |
|---|---|---|---|---|
| 0 | 20 | 25 | 26 | 30 |
| % B | 5 | 100 | 100 | 5 | stop |

Sample Preparation:
Sample solution for HPLC in Example 3.1), c) was prepared according to the following recipe: dissolve approx. 100 µL (microliter) of the reaction mixture in 0.2 mL of isopropanol, add approx. 50 mg of NaBH$_4$ and agitate for 10 min at 25° C. Extract with 0.2 mL of ethyl acetate and 0.5 mL of a 5% KH$_2$PO$_4$ buffer (pH 7,0). Dilute 50 µL (microliter) of the resulting organic layer in a 10 mL volumetric flask and fill to the mark with solvent. Sample weights are adapted according to instrument requirements.

Sample solution for HPLC for Example 3.1), d), Example 3.2), c) and Example 3.3), b) was prepared according to the following recipe: dissolve approx. 100 µL of the reaction mixture in 2 mL of acetonitrile in a 20 mL volumetric flask and fill to the mark with solvent. Sample weights are adapted according to instrument requirements.

Example 4

Synthesis of the Compound of Formula (IVb)

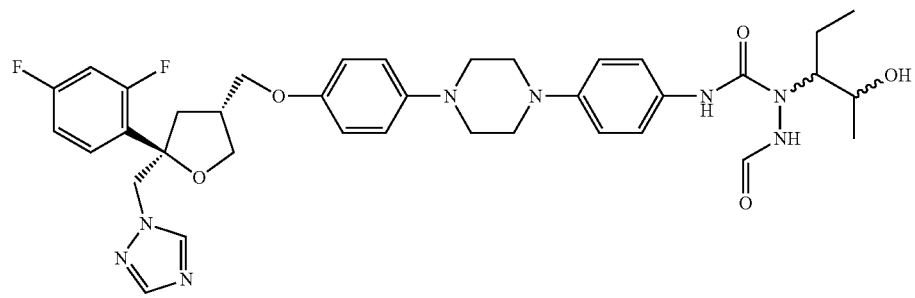 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

32.63 g carbonyldiimidazole (compound of formula (IIc), 1.1 eq, 201.2 mmol, Sinochem Jiangsu #090506) were dissolved under nitrogen atmosphere in 1300 mL DCM in a 2.0 L Schmizo reactor and cooled to −10° C. under permanent stirring.

Afterwards 100.0 g of the compound of formula (Ia) obtained according to Example 2 (1 eq., 182.9 mmol) were added and rinsed in with additional 300 mL DCM. The reaction mixture was stirred at −10° C. for 2 hours.

Subsequently, 30.76 g of the compound of formula (IIIa) as obtained in Example 3 (1.1 eq, 201.23 mmol) were added and rinsed with 300 mL DCM. The reaction mixture was warmed to 30° C. and afterwards stirred for 3 hours at this temperature.

Afterwards the reaction mixture was cooled to 25° C. and the mixture was stirred at this temperature for 4 hours. Crystallization occurred after 2.5 hours. The suspension then was cooled to 0° C. and stirred for additional 15 hours at this temperature. The solid was isolated via vacuum filtration (time: about 15 min) and afterwards, the filtercake was washed two times each with 100 mL of ice cold DCM. The filtercake was dried (20-25° C., <50 mbar) and afterwards, 129.2 g of the compound of formula (IVb) were isolated as a 1/1/1 crystallisate with imidazole and DCM (MED) (>98.5 area % of the compound of formula (IVb) excluding imidazole, determined by HPLC as described below yield: 81.5%). The ratio of the compound of formula (IVb) to imidazole and to DCM (MED) was detected via NMR.

At least 99% of the molecules of the compound of formula (IVb) were obtained as isomer of formula (IVd)

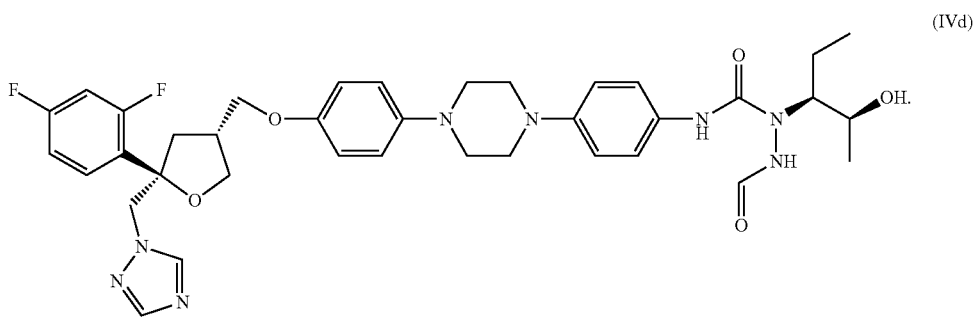

(IVd)

The IR spectrum and X-ray diffractogram of the obtained compound of formula (IVb) are shown in FIGS. 4 and 5.

Infrared spectra (IR) data and X-ray data (powder diffraction pattern XRPD) were determined according to the methods as described in Example 3.

$^1$H-NMR and $^{13}$C-NMR spectra of the obtained compound of formula (IVb) as obtained in Example 4 were collected. The following results were obtained $^1$H-NMR (CDCl$_3$, 300 mHz):

delta (ppm)=0.93-1.02 (m, 3 H), 1.26 (m, 3 H), 1.45 (m, 1 H), 2.06 (m, 2 H), 3.22 (m, 8H), 3.52-3.80 (m, 4 H), 4.11 (m, 1 H), 4.52 (d, J=16 Hz, 1 H), 4.64 (d, J=16 Hz, 1 H), 5.30 (s, DCM (MED)), 6.74-6.93 (m, 8 H), 7.09 (s, 2 H), 7.29-7.39 (m, 3 H), 7.67 (s, 1 H), 7.79 (s, 1 H), 8.14 (s, 1 H), 8.22 (b, 1.5; H), 9.53 (b, 0.5; H) rotamers.

$^{13}$C-NMR (CDCl$_3$, 75 mHz): delta (ppm) 10.9, 19.7, 21.5, 37.4, 38.8, 49.9, 50.6, 55.9, 67.2, 68.9, 70.7, 84.0, 104.6 (t), 111.4 (q), 115.0, 116.9, 118.3, 122.0, 125.4 (q), 128.5 (q), 130.5, 131.1, 144.5, 145.8, 148.8, 149.0, 151.0, 152.8, 156.4, 157.4 (t), 160.7 (q), 164.3, 164.5.

HPLC Method for determination of purity of the obtained compound of formula (IVb):
Column: Zorbax Eclipse XDE-C18, Rapid Res., 4.6×50 mm, 1.8 μm,
flow: 1.5 mL/min
wavelength: 210 nm
Auto sampler: 5° C.
oven temperature: 55° C.
Eluent A: 20 mM Phosphate buffer pH 6.5/acetonitrile 85/14 (v/v)
Eluent B: 20 mM Phosphate buffer pH 6.5/acetonitrile 25/75 (v/v)
Gradient: 0 min/29% B, 10 min/55% B, 12 min/100% B, 15 min/100% B, 15.1 min/29B, 17 min stop Samples Preparation:

The sample (7-10 mg) was dissolved in a 1/1 mixture of acetonitrile and water mixture, and in case of slow dilution ultra sonic bath was used to gain complete dilution.

Example 5

Synthesis of the compound of formula (Vb)

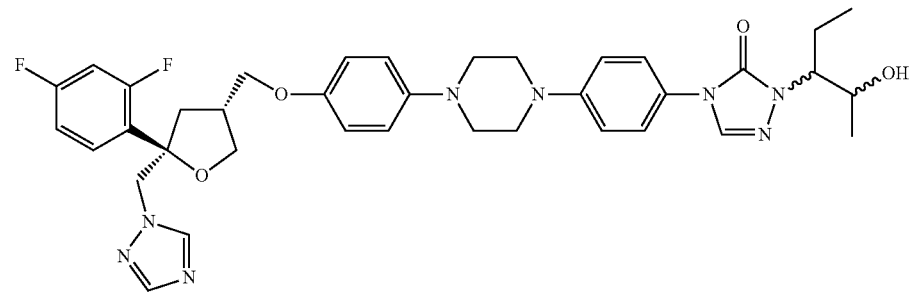 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

50.0 g of the compound of formula (IVb) as obtained according to Example 4 above (1 eq, 57.39 mmol) were dissolved in 1600 mL isopropylacetate. To the suspension, 18.66 g imidazole (5.8 eq in total with the imidazole contained in the starting material, 332.8 mmol) and 20.83 g BSA (1.78 eq, 102.4 mmol, 25.0 mL) were added and the mixture was stirred for 45 min until a clear solution occurred.

Afterwards 4.30 g of TMSI solution in DCM containing 2.56 g TMSI (0.22 eq, 12.78 mmol) were added, and the reaction mixture was heated to reflux (89° C.) and stirred at that temperature for 19 hours until complete conversion of the compound of formula (IVb) was observed.

The reaction mixture was added dropwise at a temperature between 50-60° C. to 500 mL 10% HCl. The aqueous phase was separated, and 750 mL DCM were added. Afterwards the pH of the mixture was adjusted to 1.02 by the addition of about 225 mL of 20% NaOH solution. The organic phase was separated and washed with 500 mL 0.1 M HCl followed by a washing with 330 mL 5% sodium bicarbonate solution. Afterwards the organic solvent was removed under reduced pressure (40° C., 600-20 mbar) leading to 50.71 g of compound of formula (Vb) as a white solid. The solid was dissolved in acetone and afterwards 325 mL water were added. To the solution 10 g charcoal (Ceca Eno) were added and the mixture was stirred for 30 min. Afterwards the charcoal was removed via filtration, the filter cake was washed with 300 mL of an acetone/water (5/1) mixture leading to a slightly yellow solution. The solution was warmed to 27° C. and 1000 mL water were added.

Subsequently 40 mg seeding crystals (obtained according to above-described process followed by purification by chromatography) were added and the mixture was stirred for 60 min leading to white slurry. Additional 500 mL water were added and the mixture was stirred at 30° C. for 30 min, cooled to 15° C. and stirred at that temperature for 120 min. Afterwards the white solid was separated via filtration (G3, d=12 cm) and the filter cake was washed with 375 mL of an acetone/water (1/2) mixture. The isolated solid was dried under vacuum (<45 mbar) at 40° C. for 16 hours leading to 32.57 g of the compound of formula (Vb) (46.48 mmol, 81.0%, contents 98.9%).

At least 99% of the molecules of the compound of formula (Vb) were obtained as isomer of formula (Vd)

under vacuum to give 8.6 g of white needles. Said product was suspended in a mixture of 160 ml of water and 40 ml of methanol. 0.9 g of seed crystals Form IV were added. Said seed crystals were prepared as described in WO 2010/000668 A1, example 2, on page 23, lines 16 to 25, this disclosure being incorporated herein by reference, as well as the patent document U.S. Pat. No. 6,958,337 cited therein. The suspension was heated to 40° C. and stirred until the conversion to polymorphic form IV was completed. The white suspension was then cooled down to about 10° C. and the solid was collected by filtration. After washing with 20 ml of water the product was dried at room temperature under vacuum to yield 9 g of the compound of formula (Vb), polymorphic form IV, as a white powder.

List of Cited Documents
WO 96/33178
WO 93/09114

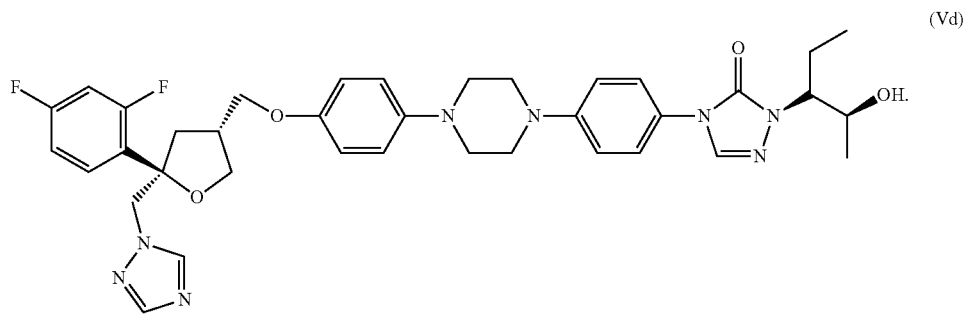

(Vd)

HPLC Method for determination of the ratio of Vd to Vb:
Column: Daicel CHIRALCEL OD, 250×4.6 mm
System: isocratic
Eluent:Hexane/Ethanol/Diethylamine=30/70/0.2 (v/v/v)
Flow rate: 1.0 mL/min
Oven temperature: 39° C.
Injection volume: 15 μL
Stop time: 20 min
Detection: λ (lambda)=260 nm (Agilent 1100 detector)
Autosampler: 39° C.
Solutions Prepared According to the Following Recipe:
Dissolve 24 to 27 mg of the substance to be tested, weighed accurately to 0.01 mg, in solvent in a 25-mL volumetric flask. Fill to the mark with solvent and shake well.

Example 6

Preparation of polymorph form IV of the compound of formula (Vb)

The product obtained in Example 5 was transformed to the polymorph form IV which is described in detail in WO 2010/000668.

10.0 g of the compound of formula (Vb) as obtained in Example 5 were added to 110 ml acetone, and the mixture was heated to reflux. 33 ml of water were added to the hot suspension and a clear solution was immediately obtained. The hot solution was filtered and allowed to cool to about 20° C. within 45 min. After standing in a refrigerator at about 5° C. for 17 hours the precipitated product was filtered and dried WO 95/17407
WO 2006/007540
Huang et al., Organic Letters 2004, 6 (25) 4795-4798
M. Hepperle et. al *Tetrahedron Lett.* 2002, 43, 3359-3363
U.S. Pat. No. 6,355,801 B1
EP 1 230 231 B1
U.S. Pat. No. 5,403,937
EP 0 736 030 A1
WO 2010/000668
Remington's Pharmaceutical Sciences, 15$^{th}$ Ed., Mack Publishing Co., New Jersey (1991)
WO 96/38443
WO 02/80678
WO 2005/117831
WO 99/18097
U.S. Pat. No. 5,972,381
U.S. Pat. No. 5,834,472
U.S. Pat. No. 4,957,730
Greene et al., "Protective Groups in Organic Synthesis", 3$^{rd}$ Ed., Wiley-Interscience (1999)
Brown et al., *J. Chem. Soc.* 2003, 125 (36), 10808-10809
U.S. Pat. No. 6,958,337

The invention claimed is:
1. An optionally crystalline chiral compound of formula (IVa)

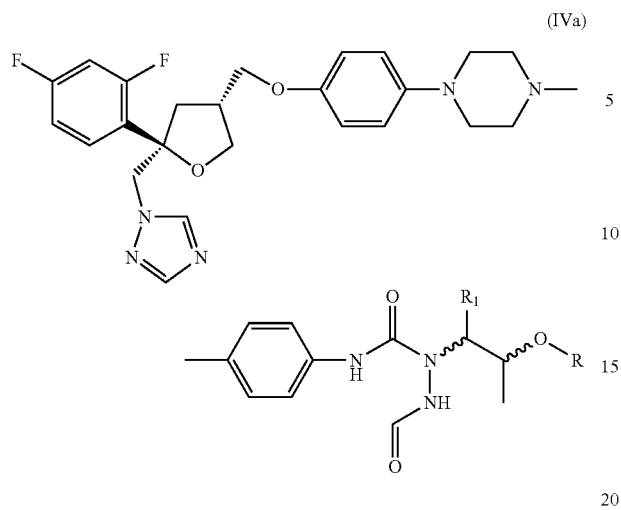

or a salt thereof,
wherein $R_1$ is an alkyl residue having from 1 to 6 carbon atoms and wherein —R is —H or the hydroxyl protecting group —$SiR_aR_bR_c$, where $R_a$, $R_b$ and $R_c$ are the same or different and selected from the group consisting of optionally suitably substituted alkyl and aryl residues.

2. The compound of claim 1, wherein at least 95% of the molecules of said compound are present as compound of formula (IVc)

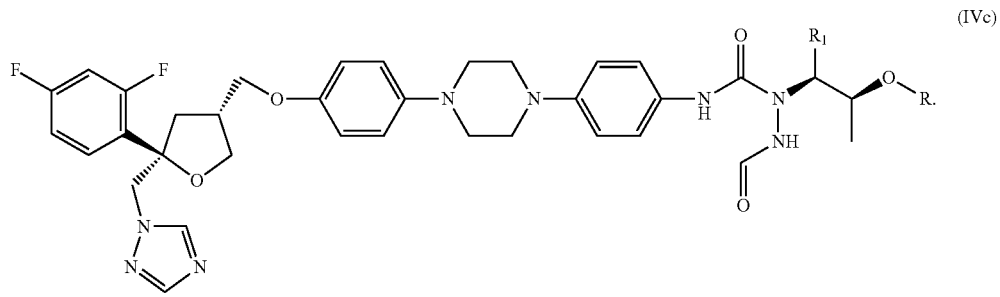

3. The compound of claim 1, wherein —R is —H or —Si$(CH_3)_3$.

4. The compound of claim 1, wherein the compound is a compound of formula (IVb)

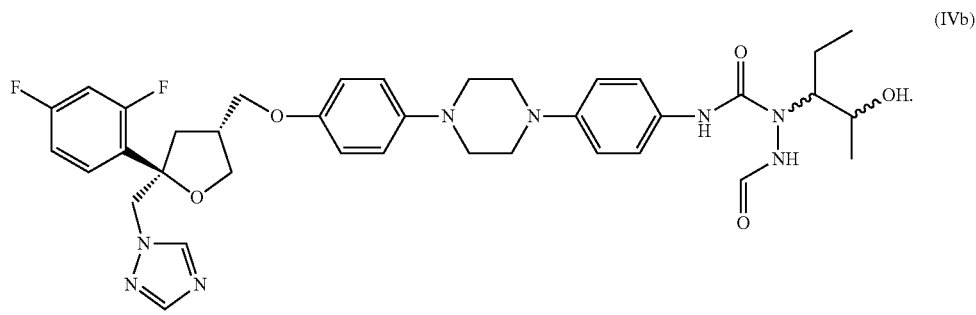 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

5. The compound of claim 2, wherein at least 97% of the molecules of said compound are present as compound of formula (IVc).

6. The compound of claim 2, wherein at least 99% of the molecules of said compound are present as compound of formula (IVc).

7. The compound of claim 1, wherein at least 95% of the molecules of said compound are present as compound of formula (IVd)

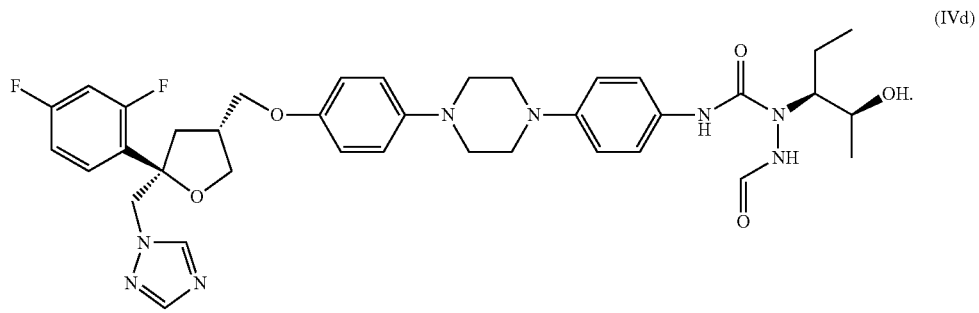 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

(IVd)

8. The compound of claim 7, wherein at least 97% of the molecules of said compound are present as compound of formula (IVd).

9. The compound of claim 7, wherein at least 99% of the molecules of said compound are present as compound of formula (IVd).

10. A process for the preparation of a chiral compound according to claim 1, comprising (1.1) providing a compound of formula (Ia)

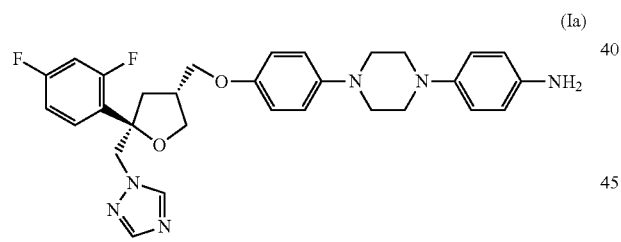

(Ia)

or a salt thereof,

{1.2) providing a phosgene derivative of formula (Ib)

(IIb)

wherein $Y_1N$— and $Y_2N$— are the same or different optionally substituted nitrogen heterocycle moieties, (1.3) providing a compound of formula (III)

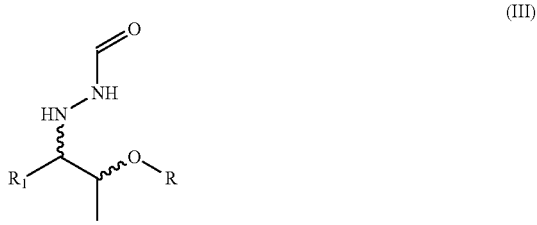

(III)

or a salt thereof;

(2) mixing and reacting the compounds of formulae (Ia), (IIb), and (III) in a solvent in any order to obtain a reaction mixture containing a chiral compound of formula (IVa) or formula (IVa) and formula (Va)

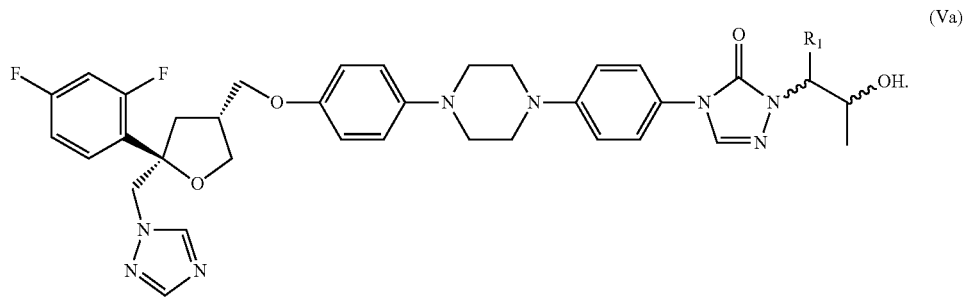

(Va)

11. The process of claim 10, wherein Y₁N— and Y₂N— are selected from the group consisting of imidazolyl and benzimidazolyl.

12. The process of claim 10, wherein in (2),
   (2.1) the compounds of formulae (Ia) and (IIb) are mixed and at least partially reacted in a solvent to obtain a reaction mixture;
   (2.2) adding the compound of formula (III) to the reaction mixture obtained from (2.1).

13. The process of claim 10, wherein reacting in (2) is carried out in the absence of a compound of formula Cl—C(=O)—O-Ph or in the absence of an ester of a halogenated formic acid.

14. The process of claim 10, wherein in (2), the solvent is a polar aprotic solvent or a mixture of two or more thereof.

15. The process of claim 14, wherein the solvent is selected from the group consisting of dichloromethane DCM, tetrahydrofurane (THF), methyl tetrahydrofurane (MeTHF), acetonitrile (AN), an ester wherein the ester is butylacetate (BuAc) or ethylacetate (EtAc), dimethylformamide (DMF) and a mixture of two or more thereof.

16. The process of claim 10, wherein reacting in (2) is carried out at a temperature in the range of from −20 to +40° C.

17. The process of claim 10, wherein reacting in (2) is carried out in the presence of an acid.

18. The process of claim 17, wherein the acid is trifluoroacetic acid (TFA).

19. The process of claim 10, wherein the compound of formula (IIb) is a carbonyldiimidazole (CU) of formula (IIc)

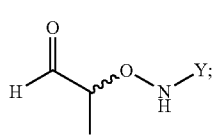

(IIc)

20. The process of claim 10, wherein in the compound of formula (III), R₁ is an alkyl residue having from 1 to 4 carbon atoms and wherein —R is —H or a hydroxyl protecting group selected from the group consisting of —Si(CH₃)₃ and benzyl.

21. The process of claim 10, wherein the compound of formula (III) is a crystalline compound

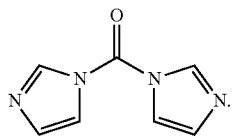

(IIIa)

22. The process of claim 21, wherein at least 95% of the molecules of said crystalline compound are present as

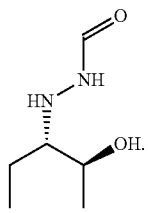

(IIIb)

23. The process of claim 10, wherein in (1.3), the compound of formula (III) is provided by a process comprising
   (a) providing a chiral compound of formula (i)

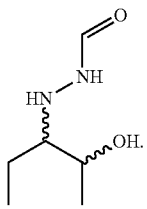

(i)

wherein Y is an optionally substituted aryl moiety, said providing in (a) comprising reacting propionaldehyde in a solvent with a compound of formula (j)

O=N—Y                                                          (j), in the presence of a catalyst system, said catalyst system optionally further comprising a promoter;
   (b) reacting the compound of formula (i) with H₂N—NH—CHO in a solvent, to obtain a compound according to formula (ii)

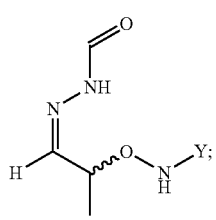

(ii)

(c) separating the compound of formula (ii) from the reaction mixture obtained from (b) by solvent extraction;
   (d) optionally reacting the compound of formula (ii) in a solvent with a silylating agent comprising the residue —SiR$_{aa}$R$_{bb}$R$_{cc}$ to obtain a compound of formula (iii)

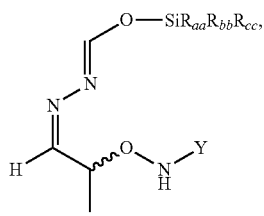

(iii)

wherein the residues R$_{aa}$, R$_{bb}$ and R$_{cc}$ may be the same or different and are alkyl or aryl residues;
   (e) reacting the compound of formula (ii) or reacting the compound of formula (iii) with a nucleophilic compound comprising a nucleophilic residue R₁ wherein R₁ is an alkyl residue having from 1 to 6 carbon atoms in a solvent, to obtain a compound of formula (iv)

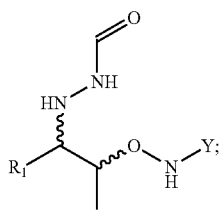
(iv)

(f) reducing the compound of formula (iv), to obtain a compound of formula (III) with R=H

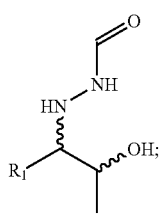

(g) optionally crystallizing the compound of formula (III) with R=H;
(h) optionally recrystallizing the compound of formula (III) with R=H, and
(i) optionally reacting the optionally crystallized compound of formula (III) with R=H in a solvent with a silylating agent comprising the residue —SiR$_a$R$_b$R$_c$ to obtain a compound of formula (III) with R=SiR$_a$R$_b$R$_c$

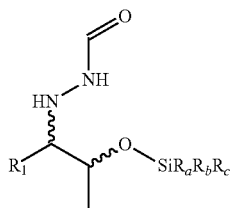

wherein the residues R$_a$, R$_b$ and R$_c$ may be the same or different and are alkyl or aryl residues.

24. The process of claim 23, wherein in (a) the catalyst system comprises at least one organocatalyst.

25. The process of claim 24, wherein the organocatalyst is D-Proline.

26. The process of claim 23, wherein in (a) the promoter is an urea derivative.

27. The process of claim 23, wherein prior to (c), a solvent exchange is carried out.

28. The process of claim 23, wherein the nucleophilic compound is a Grignard compound R$_1$MgX wherein X is selected from the group consisting of Cl, Br, and I.

29. The process of claim 23, wherein in (e), the solvent is selected from the group consisting of toluene, tetrahydrofurane (THF), MTBE, and a mixture of THF and MTBE.

30. The process of claim 23, wherein in (h) the compound of formula (III) with R=H is recrystallized from isopropyl acetate.

31. The process of claim 23, wherein at least 95% of the molecules of the chiral compound of formula (i) provided in (a) are present as

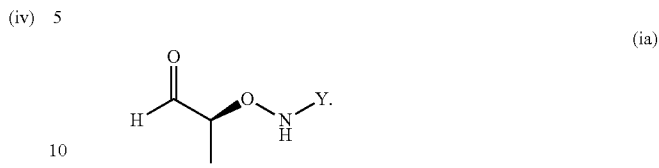
(ia)

32. The process of claim 10, wherein in (1.1), the compound of formula (I) is provided by a process comprising
(aa) reacting a compound of formula (A)

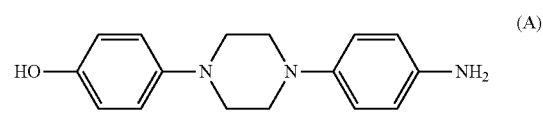
(A)

in a polar protic or a polar aprotic solvent,
and in the presence of a base with a compound of formula (B)

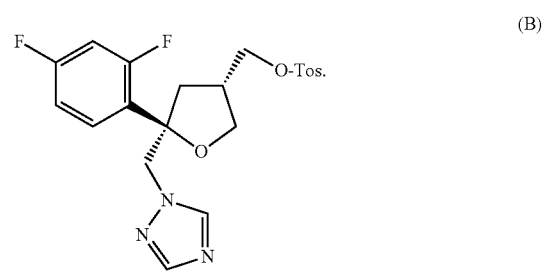
(B)

33. The process of claim 32, wherein the solvent is selected from the group consisting of dimethylsulfoxide (DMSO), dimethylformamide (DMF), N-methylpyrrolidone (NMP), sulfolane, methanol, ethanol, n-propanol, and isopropanol; and
the base is a carbonate, a hydroxide and/or a hydrogencarbonate.

34. The process of claim 33, wherein the solvent is ethanol or DMSO; and wherein the base is sodium hydroxide and potassium carbonate.

35. The process of claim 32, wherein the base is sodium hydroxide employed as aqueous solution with a concentration of at least 20 wt. % with respect to the base.

36. The process of claim 32, further comprising (bb) at least once re-crystallizing the compound of formula (I).

37. The process of claim 36, wherein the recrystallizing of (bb) is from acetonitrile and/or water.

38. The process of claim 10, comprising isolating the chiral compound of formula (IVa) from the reaction mixture obtained from (2).

39. The process of claim 38, wherein said isolating is carried out by crystallization.

40. The process of claim 10, further comprising
(3) either heating the mixture obtained from (2), optionally during and/or after solvent exchange, or heating a mixture obtained from mixing the isolated chiral compound of formula (IVa) with a solvent, to a temperature in the range of from 40 to 150° C. to obtain a compound according to formula (Va)

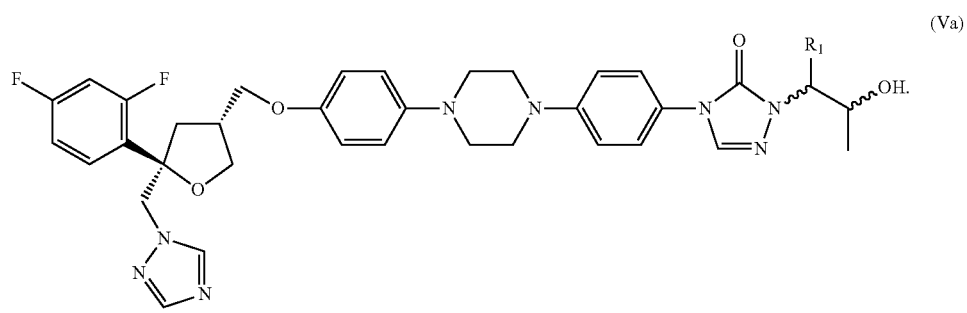

(Va)

41. The process of claim 40, wherein either the mixture obtained from (2) or the mixture obtained from mixing the isolated chiral compound of formula (IVa) with a solvent is heated to a temperature in the range of from 60 to 140° C.

42. The process of claim 40, wherein prior to heating, either the mixture obtained from (2), optionally after solvent exchange, or the mixture obtained from mixing the isolated chiral compound of formula (IVa) with a solvent, is admixed with a silylating agent.

43. The process of claim 42, wherein the silylating agent is trimethylsilylchloride (TMSCI), trimethylsilyl iodide (TMSI) or bis-trimethylsilylacetamide (BSA) or a combination thereof.

44. The process of claim 42, wherein prior to admixing with the silylating agent, imidazole is admixed in amount so that the molar ratio of imidazole relative to the compound of formula (IVa) is in the range of 2:1 to 10:1.

45. The process of claim 40, wherein the mixture obtained from (2) contains a solvent selected from the group consisting of dichloromethane (DCM), tetrahydrofurane (THF), methyl tetrahydrofurane (MeTHF), acetonitrile (AN), an ester, butylacetate (BuAc) or ethylacetate (EtAc) and dimethylformamide (DMF), and a mixture of two or more thereof, and prior to heating the mixture obtained from (2), said solvent is exchanged by a different solvent suitable to allow the temperature conditions according to claim 40, said different solvent being selected from the group consisting of toluene, benzene, an ester of a saturated carboxylic acid, dimethylformamide (DMF), acetonitrile (AN), methyltetrahydrofurane (Me-THF), methylisobutylketone (MIBK), dioxane, hexamethyldisilazane (HMDS), and a mixture of two or more thereof.

46. The process of claim 40, further comprising (4) extracting the compound of formula (Va).

47. The process of claim 41, wherein the extracting is carried out by using an aqueous acid, as extracting agent.

48. The process of claim 46, further comprising
(5) crystallizing the compound of formula (Va) in a solvent, and
(6) optionally separating the crystallized compound from the solvent.

49. The process of claim 48, wherein crystallizing in (5) is carried out in a solvent which is selected from the group consisting of alcohols, ethers acetone, acetonitrile, and a mixture of two or more thereof.

50. The process of claim 49, wherein the alcohol is selected from methanol, ethanol, n-propanol, iso-propanol and the ethers is THF.

51. The process of claim 49, wherein the solvent is admixed with water.

52. The process of claim 10, for the preparation of posaconazole, comprising (1.1) providing a compound of formula (Ia)

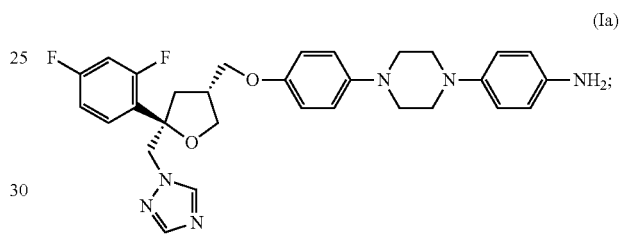

(Ia)

(1.2) providing a compound of formula (IIc)

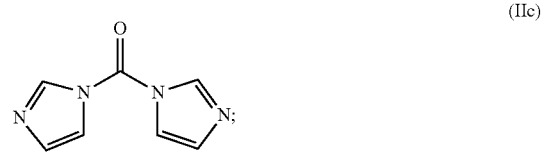 [SMILES: O=C(n1ccnc1)n1ccnc1]

(IIc)

(1.3) providing a compound of formula (IIIa)

(IIIa)

wherein at least 99% of the molecules of said compound are present as compound of formula (IIIb)

(IIIb)
(2) mixing and reacting the compounds of formulae (Ia), (IIc), and (IIIa) in a solvent in any order to obtain a reaction mixture containing a chiral compound of formula (IVb)
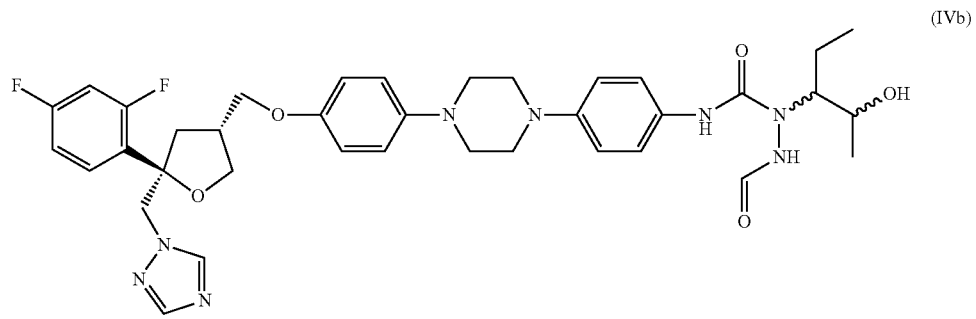 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVb)
wherein at least 99% of the molecules of said compound are present as compound of formula (IVd)
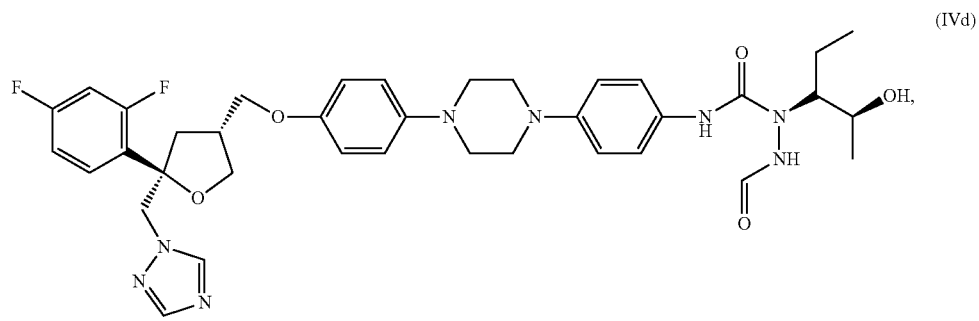
(IVd)
or of formula (IVb) and of formula (Vb)
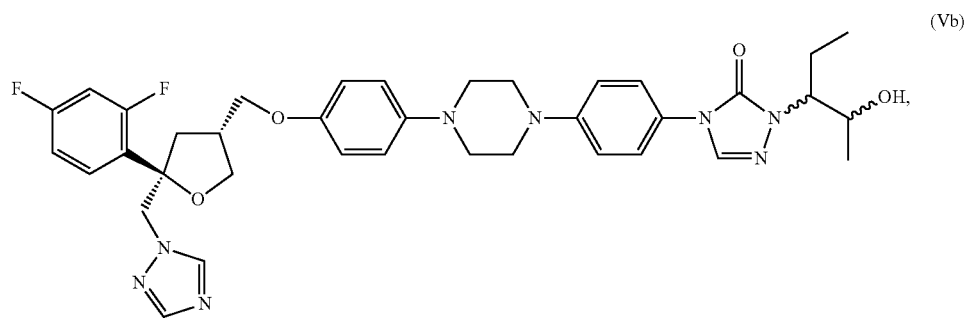 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vb)

wherein at least 99% of the molecules of said compound are present as compound of formula (Vd)

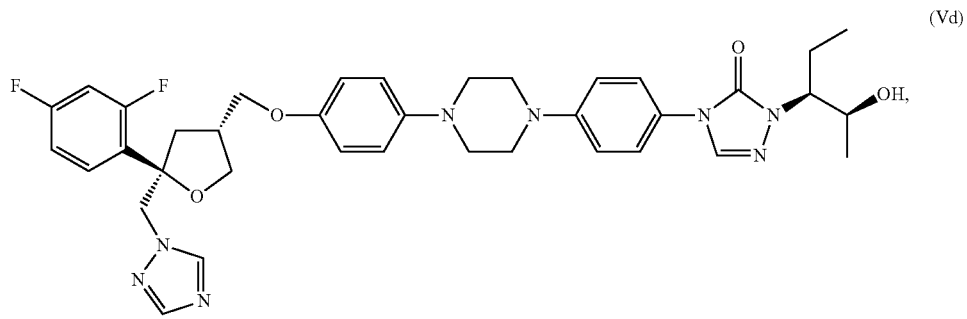 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vd)

wherein in (2),
(2.1) the compounds of formulae (Ia) and (IIc) are mixed and at least partially reacted in a solvent to obtain a reaction mixture;
(2.2) and the compound of formula (IIIa) is added to the reaction mixture obtained from (2.1);
(3) either heating the mixture obtained from (2), optionally during and/or after solvent exchange, or heating a mixture obtained from mixing the isolated chiral compound of formula (IVb) with a solvent, to a temperature in the range of from 40 to 150° C. to obtain a compound according to formula (Vb);
(4) extracting the compound of formula (Vb), using aqueous hydrochloric acid, as extracting agent;
(5) crystallizing the compound of formula (Vb) in a solvent; and
(6) optionally separating the crystallized compound of formula (Vb) from the solvent.

53. The process of claim 50, wherein the crystallized compound obtained from (5) or (6) is not subjected to a subsequent chromatography purification stage or a subsequent purification stage.

54. The process of claim 50, wherein the crystallized compound obtained from (5) or (6), in particular the compound of formula (Vb)

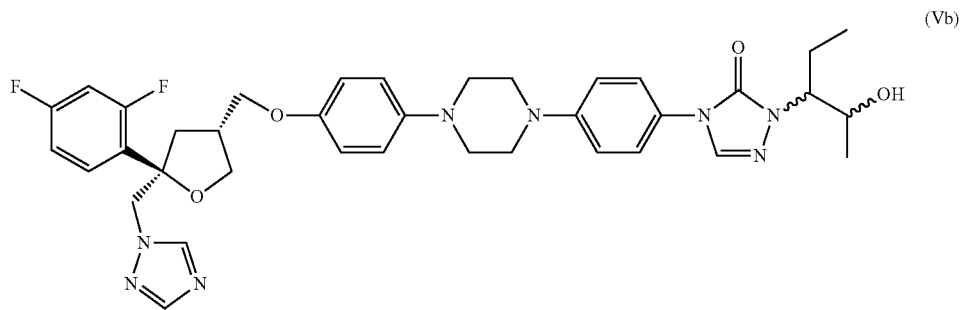 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vb)

is re-crystallized.

55. The process of claim 54, wherein compound (Vb) is recrystallized from a mixture of acetone and water or from methanol, and is subsequently stirred in a mixture of water and methanol.

56. The process of claim 54, wherein at least 95% of the molecules of said crystalline compound are present as isomer of formula (Vd)

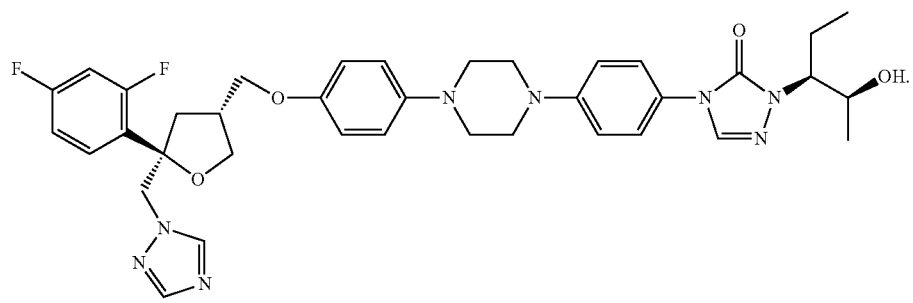 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

57. The process of claim 54, wherein at least 97% of the molecules of said crystalline compound are present as isomer of formula (Vd)

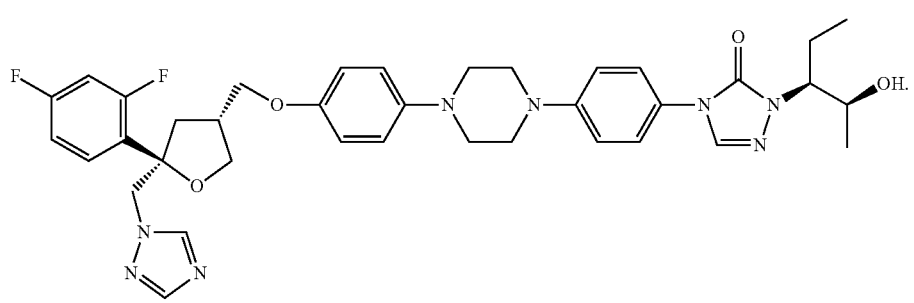

(Vd)

58. The process of claim 54, wherein at least 99% of the molecules of said crystalline compound are present as isomer of formula (Vd)

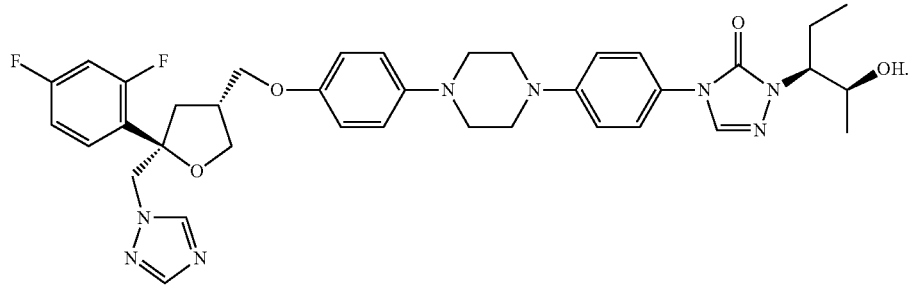

(Vd)

59. The process of claim 54, wherein the re crystallization is carried out in the presence of seed crystals, said seed crystals comprising the crystalline compound of formula (Vd) in the form of polymorph IV.

\* \* \* \* \*